(12) United States Patent
Kenderian et al.

(10) Patent No.: US 12,264,189 B2
(45) Date of Patent: Apr. 1, 2025

(54) METHODS AND MATERIALS FOR TREATING CANCER

(71) Applicant: Mayo Foundation for Medical Education and Research, Rochester, MN (US)

(72) Inventors: Saad J. Kenderian, Rochester, MN (US); Stephen James Russell, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 913 days.

(21) Appl. No.: 17/287,164

(22) PCT Filed: Oct. 31, 2019

(86) PCT No.: PCT/US2019/059260
§ 371 (c)(1),
(2) Date: Apr. 21, 2021

(87) PCT Pub. No.: WO2020/092839
PCT Pub. Date: May 7, 2020

(65) Prior Publication Data
US 2021/0355190 A1  Nov. 18, 2021

Related U.S. Application Data

(60) Provisional application No. 62/753,732, filed on Oct. 31, 2018.

(51) Int. Cl.
*C07K 14/705* (2006.01)
*A61K 39/00* (2006.01)
*A61P 35/00* (2006.01)
*C07K 16/28* (2006.01)
*C12N 7/00* (2006.01)
*A61K 38/00* (2006.01)

(52) U.S. Cl.
CPC .... *C07K 14/70503* (2013.01); *A61K 39/4611* (2023.05); *A61K 39/4631* (2023.05); *A61K 39/464412* (2023.05); *A61P 35/00* (2018.01); *C07K 16/2809* (2013.01); *C12N 7/00* (2013.01); *A61K 38/00* (2013.01); *A61K 2239/48* (2023.05)

(58) Field of Classification Search
CPC .......... C07K 14/70503; C07K 16/2809; A61P 35/00; A61K 35/17; A61K 38/00; C12N 7/00
See application file for complete search history.

(56) References Cited

U.S. PATENT DOCUMENTS

| | | |
|---|---|---|
| 3,687,808 A | 8/1972 | Merigan, Jr. et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |
| 4,769,330 A | 9/1988 | Paoletti et al. |
| 4,816,567 A | 3/1989 | Cabilly et al. |
| 4,861,627 A | 8/1989 | Mathiowitz et al. |
| 4,861,719 A | 8/1989 | Miller |
| 4,925,673 A | 5/1990 | Steiner et al. |
| 4,935,496 A | 6/1990 | Kudo |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |
| 5,225,336 A | 7/1993 | Paoletti |
| 5,225,538 A | 7/1993 | Capon et al. |
| 5,235,033 A | 8/1993 | Summerton et al. |
| 5,240,846 A | 8/1993 | Collins et al. |

(Continued)

FOREIGN PATENT DOCUMENTS

| | | |
|---|---|---|
| CN | 103641917 | 3/2014 |
| CN | 105814074 | 7/2016 |

(Continued)

OTHER PUBLICATIONS

Boyiadzis et al., "The emerging roles of tumor-derived exosomes in hematological malignancies," Leukemia, Mar. 21, 2017, 31(6):1259-1268.

(Continued)

*Primary Examiner* — Janet L Epps-Smith
*Assistant Examiner* — Estella M. Gustilo
(74) *Attorney, Agent, or Firm* — Fish & Richardson P.C.

(57) ABSTRACT

This document provides methods and materials for generating T cells expressing a selected antigen receptor (e.g., a chimeric antigen receptor) in vivo. For example, viral particles containing nucleic acid encoding a selected antigen receptor, cells capable of producing such viral particles, and methods for administering such viral particles and/or cells to a mammal to generate T cells expressing that selected antigen receptor within the mammal are provided.

10 Claims, 10 Drawing Sheets
Specification includes a Sequence Listing.

(56) References Cited

U.S. PATENT DOCUMENTS

| | | |
|---|---|---|
| 5,254,678 A | 10/1993 | Haseloff et al. |
| 5,278,056 A | 1/1994 | Bank et al. |
| 5,284,656 A | 2/1994 | Platz et al. |
| 5,296,347 A | 3/1994 | LaMotte, III |
| 5,391,682 A | 2/1995 | Ogawa et al. |
| 5,451,569 A | 9/1995 | Wong et al. |
| 5,502,167 A | 3/1996 | Waldmann et al. |
| 5,521,288 A | 5/1996 | Linsley et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,584 A | 10/1996 | Sledziewski et al. |
| 5,585,089 A | 12/1996 | Queen et al. |
| 5,596,086 A | 1/1997 | Matteucci et al. |
| 5,639,641 A | 6/1997 | Pedersen et al. |
| 5,674,704 A | 10/1997 | Goodwin et al. |
| 5,675,848 A | 10/1997 | Kappel |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,714,147 A | 2/1998 | Capon et al. |
| 5,733,743 A | 3/1998 | Johnson et al. |
| 5,750,078 A | 5/1998 | Shitara et al. |
| 5,750,375 A | 5/1998 | Sledziewski et al. |
| 5,750,666 A | 5/1998 | Caruthers et al. |
| 5,770,403 A | 6/1998 | Dalie et al. |
| 5,843,725 A | 12/1998 | Sledziewski et al. |
| 5,861,310 A | 1/1999 | Freeman et al. |
| 5,874,240 A | 2/1999 | Ni et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aruffo et al. |
| 6,291,212 B1 | 9/2001 | Sledziewski et al. |
| 6,291,646 B1 | 9/2001 | Sledziewski |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,891,030 B2 | 5/2005 | Chen |
| 6,919,193 B2 | 7/2005 | Tang et al. |
| 6,943,150 B1 | 9/2005 | Altieri |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle |
| 7,432,351 B1 | 10/2008 | Chen |
| 7,449,300 B2 | 11/2008 | Chen et al. |
| 7,560,540 B2 | 7/2009 | Pardoll et al. |
| 7,563,869 B2 | 7/2009 | Honjo et al. |
| 7,582,439 B2 | 9/2009 | Cory et al. |
| 7,595,048 B2 | 9/2009 | Honjo et al. |
| 7,651,686 B2 | 1/2010 | Chen et al. |
| 7,709,214 B2 | 5/2010 | Freeman et al. |
| 7,723,479 B2 | 5/2010 | Mikesell et al. |
| 7,794,710 B2 | 9/2010 | Chen et al. |
| 7,892,540 B2 | 2/2011 | Chen et al. |
| 8,008,449 B2 | 8/2011 | Korman et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,163,550 B2 | 4/2012 | Chen et al. |
| 8,268,635 B2 | 9/2012 | Ferrante et al. |
| 8,273,861 B2 | 9/2012 | Chen |
| 8,383,405 B2 | 2/2013 | Orme |
| 8,460,927 B2 | 6/2013 | Chen |
| 8,518,409 B2 | 8/2013 | Orme |
| 8,772,026 B2 | 7/2014 | Chen et al. |
| 8,901,120 B2 | 12/2014 | Bearss et al. |
| 8,981,063 B2 | 3/2015 | Chen |
| 9,302,005 B2 | 4/2016 | Dong et al. |
| 9,534,058 B2 | 1/2017 | Stull et al. |
| 9,598,491 B2 | 3/2017 | Ahmed et al. |
| 9,730,988 B2 | 8/2017 | Ince et al. |
| 11,246,890 B2 | 2/2022 | Lin et al. |
| 11,419,898 B2 | 8/2022 | Lu et al. |
| 2002/0076409 A1 | 6/2002 | March et al. |
| 2002/0091246 A1 | 7/2002 | Pardoll et al. |
| 2002/0095024 A1 | 7/2002 | Mikesell et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0119121 A1 | 8/2002 | Vitiello et al. |
| 2002/0160395 A1 | 10/2002 | Altieri et al. |
| 2002/0160973 A1 | 10/2002 | Pero et al. |
| 2002/0164600 A1 | 11/2002 | Freeman et al. |
| 2002/0168719 A1 | 11/2002 | Kwon |
| 2002/0177551 A1 | 11/2002 | Terman |
| 2003/0039653 A1 | 2/2003 | Chen et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0223989 A1 | 12/2003 | Pluenneke |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0180047 A1 | 9/2004 | Chen |
| 2004/0247563 A1 | 12/2004 | Lynch et al. |
| 2005/0013811 A1 | 1/2005 | Chen et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0068386 A1 | 3/2006 | Slesarev et al. |
| 2006/0084794 A1 | 4/2006 | Rosen et al. |
| 2006/0110383 A1 | 5/2006 | Honjo et al. |
| 2006/0159685 A1 | 7/2006 | Mikesell et al. |
| 2006/0223088 A1 | 10/2006 | Rosen et al. |
| 2006/0276422 A1 | 12/2006 | Usman et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0012292 A1 | 2/2009 | Chen |
| 2009/0068193 A1 | 3/2009 | Chen et al. |
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0304711 A1 | 12/2009 | Pardoll et al. |
| 2010/0015642 A1 | 1/2010 | Kwon et al. |
| 2010/0092470 A1 | 4/2010 | Bhatt et al. |
| 2010/0285039 A1 | 11/2010 | Chen |
| 2011/0020325 A1 | 1/2011 | Kwon et al. |
| 2011/0010409 A1 | 5/2011 | Strome et al. |
| 2012/0065374 A1 | 3/2012 | Pardoll et al. |
| 2012/0065385 A1 | 3/2012 | Pardoll et al. |
| 2012/0225043 A1 | 9/2012 | Chen et al. |
| 2013/0058936 A1 | 3/2013 | Bruenker et al. |
| 2013/0123566 A1 | 5/2013 | Lupold et al. |

(56) References Cited

U.S. PATENT DOCUMENTS

| | | |
|---|---|---|
| 2013/0251736 A1 | 9/2013 | Kwon et al. |
| 2013/0273656 A1 | 10/2013 | Hendrickson |
| 2014/0031260 A1 | 1/2014 | O'Donnell et al. |
| 2014/0242080 A1 | 8/2014 | Roche |
| 2014/0271674 A1 | 9/2014 | Dong |
| 2014/0329248 A1 | 11/2014 | Kwon et al. |
| 2014/0335541 A1 | 11/2014 | Kwon et al. |
| 2015/0111232 A1 | 4/2015 | Kwon et al. |
| 2015/0203580 A1 | 7/2015 | Papadopoulos et al. |
| 2015/0273033 A1 | 10/2015 | Bosch et al. |
| 2015/0337048 A1 | 11/2015 | Stull et al. |
| 2016/0045581 A1 | 2/2016 | Ince et al. |
| 2016/0051651 A1 | 2/2016 | Brogdon et al. |
| 2016/0068601 A1 | 3/2016 | Brogdon et al. |
| 2016/0153996 A1 | 6/2016 | Kwon et al. |
| 2016/0154000 A1 | 6/2016 | Kwon |
| 2016/0176967 A1 | 6/2016 | Dong et al. |
| 2016/0237407 A1 | 8/2016 | Wagner et al. |
| 2016/0251437 A1 | 9/2016 | Dong et al. |
| 2017/0089918 A1 | 3/2017 | Dong |
| 2017/0121416 A1 | 5/2017 | Stull et al. |
| 2017/0173030 A1 | 6/2017 | Dong |
| 2017/0274095 A1 | 9/2017 | Meyer et al. |
| 2017/0275375 A1 | 9/2017 | Rossi et al. |
| 2017/0327590 A1 | 11/2017 | Lowy et al. |
| 2017/0363634 A1 | 12/2017 | Kwon |
| 2018/0139940 A1 | 5/2018 | Macdonald et al. |
| 2018/0154183 A1 | 6/2018 | Sahadevan |
| 2019/0038671 A1 | 2/2019 | Fan et al. |
| 2019/0292539 A1 | 9/2019 | Fulga et al. |
| 2019/0298774 A1 | 10/2019 | Lin et al. |
| 2019/0315869 A1 | 10/2019 | Dong |
| 2019/0361033 A1 | 11/2019 | Dong |
| 2020/0054673 A1 | 2/2020 | Ports et al. |
| 2020/0061077 A1 | 2/2020 | Dong |
| 2020/0147117 A1 | 5/2020 | Ben Yakar et al. |
| 2020/0190196 A1 | 6/2020 | Dong |
| 2020/0270355 A1 | 8/2020 | Faustman |
| 2020/0271656 A1 | 8/2020 | Cumba-Garcia et al. |
| 2020/0338112 A1 | 10/2020 | Lou et al. |
| 2021/0003556 A1 | 1/2021 | Dong |
| 2021/0145830 A1 | 5/2021 | Kenderian et al. |
| 2021/0145881 A1 | 5/2021 | Kenderian et al. |
| 2021/0401886 A1 | 12/2021 | Kenderian et al. |
| 2022/0041686 A1 | 2/2022 | Mackall et al. |
| 2022/0401488 A1 | 12/2022 | Kenderian et al. |
| 2023/0045174 A1 | 2/2023 | Rezvani et al. |

FOREIGN PATENT DOCUMENTS

| | | |
|---|---|---|
| CN | 107406517 | 11/2017 |
| CN | 107849112 | 3/2018 |
| EP | 1074617 | 2/2001 |
| EP | 1537878 | 6/2005 |
| EP | 2997141 | 3/2016 |
| EP | 3130350 | 2/2017 |
| EP | 2968415 | 7/2019 |
| EP | 3964265 | 3/2022 |
| WO | WO 1990/007861 | 7/1990 |
| WO | WO 1991/010741 | 7/1991 |
| WO | WO 1991/011465 | 8/1991 |
| WO | WO 1991/017271 | 11/1991 |
| WO | WO 1992/000092 | 1/1992 |
| WO | WO 1992/001047 | 1/1992 |
| WO | WO 1992/020791 | 11/1992 |
| WO | WO 1993/001222 | 1/1993 |
| WO | WO 1995/005464 | 2/1995 |
| WO | WO 1995/007707 | 3/1995 |
| WO | WO 1996/029348 | 9/1996 |
| WO | WO 1997/017613 | 5/1997 |
| WO | WO 1997/017614 | 5/1997 |
| WO | WO 1997/024447 | 7/1997 |
| WO | WO 1998/016249 | 4/1998 |
| WO | WO 1998/023635 | 6/1998 |
| WO | WO 1998/033914 | 8/1998 |
| WO | WO 1998/036096 | 8/1998 |
| WO | WO 1999/036093 | 7/1999 |
| WO | WO 1999/064597 | 12/1999 |
| WO | WO 2000/026342 | 5/2000 |
| WO | WO 2000/029445 | 5/2000 |
| WO | WO 2000/029582 | 5/2000 |
| WO | WO 2000/041508 | 7/2000 |
| WO | WO 2000/055375 | 9/2000 |
| WO | WO 2000/061612 | 10/2000 |
| WO | WO 2001/034629 | 5/2001 |
| WO | WO 2001/062905 | 8/2001 |
| WO | WO 2001/070979 | 9/2001 |
| WO | WO 2001/083750 | 11/2001 |
| WO | WO 2001/094413 | 12/2001 |
| WO | WO 2002/000692 | 1/2002 |
| WO | WO 2002/000730 | 1/2002 |
| WO | WO 2002/002587 | 1/2002 |
| WO | WO 2002/002891 | 1/2002 |
| WO | WO 2002/008279 | 1/2002 |
| WO | WO 2002/078731 | 1/2002 |
| WO | WO 2002/024891 | 3/2002 |
| WO | WO 2002/046449 | 6/2002 |
| WO | WO 2002/057453 | 7/2002 |
| WO | WO 2002/079474 | 10/2002 |
| WO | WO 2002/081731 | 10/2002 |
| WO | WO 2002/086083 | 10/2002 |
| WO | WO 2003/006632 | 1/2003 |
| WO | WO 2003/008583 | 1/2003 |
| WO | WO 2003/049755 | 6/2003 |
| WO | WO 2004/085418 | 10/2004 |
| WO | WO 2006/042237 | 4/2006 |
| WO | WO 2006/050172 | 5/2006 |
| WO | WO 2006/133396 | 12/2006 |
| WO | WO 2008/037080 | 4/2008 |
| WO | WO 2008/083174 | 7/2008 |
| WO | WO 2009/023566 | 2/2009 |
| WO | WO 2009/029342 | 3/2009 |
| WO | WO 2009/114110 | 9/2009 |
| WO | WO 2010/027423 | 3/2010 |
| WO | WO 2010/027827 | 3/2010 |
| WO | WO 2010/027828 | 3/2010 |
| WO | WO 2010/098788 | 9/2010 |
| WO | WO 2011/066342 | 6/2011 |
| WO | WO 2011/066389 | 6/2011 |
| WO | WO 2011/072246 | 6/2011 |
| WO | WO 2013/003112 | 2/2013 |
| WO | WO 2013/019906 | 2/2013 |
| WO | WO 2013/090552 | 6/2013 |
| WO | WO 2013/132044 | 9/2013 |
| WO | WO 2014/110045 | 7/2014 |
| WO | WO 2014/144666 | 9/2014 |
| WO | WO 2014/163684 | 10/2014 |
| WO | WO 2014/184143 | 11/2014 |
| WO | WO 2015/049280 | 4/2015 |
| WO | WO 2015/050663 | 4/2015 |
| WO | WO 2015/061668 | 4/2015 |
| WO | WO 2015/066262 | 5/2015 |
| WO | WO 2015/142314 | 9/2015 |
| WO | WO 2015/157252 | 10/2015 |
| WO | WO 2015/179654 | 11/2015 |
| WO | WO 2016/014148 | 1/2016 |
| WO | WO 2016/014576 | 1/2016 |
| WO | WO 2016/018920 | 2/2016 |
| WO | WO 2016/120219 | 8/2016 |
| WO | WO 2016/164731 | 10/2016 |
| WO | WO 2016/201394 | 12/2016 |
| WO | WO 2017/023803 | 2/2017 |
| WO | WO 2017/066561 | 4/2017 |
| WO | WO 2017/075389 | 5/2017 |
| WO | WO 2017/091546 | 6/2017 |
| WO | WO 2017/100587 | 6/2017 |
| WO | WO 2017/143094 | 8/2017 |
| WO | WO 2017/172981 | 10/2017 |
| WO | WO 2017/173360 | 10/2017 |
| WO | WO 2017/177179 | 10/2017 |
| WO | WO 2017/220704 | 12/2017 |
| WO | WO 2017/222593 | 12/2017 |
| WO | WO 2018/005712 | 1/2018 |
| WO | WO 2018/045069 | 3/2018 |

(56) References Cited

FOREIGN PATENT DOCUMENTS

| | | |
|---|---|---|
| WO | WO 2018/073391 | 4/2018 |
| WO | WO 2018/195339 | 10/2018 |
| WO | WO 2019/036724 | 2/2019 |
| WO | WO 2019/108756 | 6/2019 |
| WO | WO 2019/133793 | 7/2019 |
| WO | WO 2019/178334 | 9/2019 |
| WO | WO 2019/195142 | 10/2019 |
| WO | WO 2019/217423 | 11/2019 |
| WO | WO 2019/232370 | 12/2019 |
| WO | WO 2020/018620 | 2/2020 |
| WO | WO 2021/092577 | 5/2021 |
| WO | WO 2022/236049 | 11/2022 |
| WO | WO 2022/236142 | 11/2022 |
| WO | WO 2022/266396 | 12/2022 |

OTHER PUBLICATIONS

Corcoran et al., "Docetaxel-Resistance in Prostate Cancer: Evaluating Associated Phenotypic Changes and Potential for Resistance Transfer via Exosomes," PLoS One, Dec. 10, 2012, 7(12):e50999, 12 pages.

Liu, "Differential Expression of Cell Surface Molecules in Prostate Cancer Cells," Cancer Research, July 1, 200, 60:3429-3434.

Oksvold et al., "Expression of B-Cell Surface Antigens in Subpopulations of Exosomes Released From B-Cell Lymphoma Cells," Clin. Therapeutics, Jun. 18, 2014, 36(6):847-862.e1.

Baek et al., "In vitro migration capacity of human adipose tissue-derived mesenchymal stem cells reflects their expression of receptors for chemokines and growth factors," Exp. Mol. Medicine, Oct. 2011, 43(10):596-603.

Barbarino et al., "Functional role of Bruton's tyrosine kinase inhibitor therapy in the tumor microenvironment of B-cell malignancies," Oncol Res Treat, Oct. 2019, 42(suppl 4):220-221, 5 pages (Abstract Only).

Beyersdorf et al., "CD28 co-stimulation in T-cell homeostasis: a recent perspective," Immunotargets Therapy, May 4, 2015:111-122.

Boardman et al., "Expression of a Chimeric Antigen Receptor Specific for Donor HLA Class I Enhances the Potency of Human Regulatory T Cells in Preventing Human Skin Transplant Rejection," Am. J. Transplantation, Feb. 2017, 17(4):931-943.

Boroughs et al., "Chimeric antigen receptor costimulation domains modulate human regulatory T cell function," JCI Insight, Mar. 2019, 5(8):e126194, 19 pages.

Charvet et al., "Vav1 promotes T cell cycle progression by linking TCR/CD28 costimulation to FOXO1 and p27kip1 expression," J. Immunology, Oct. 2006, 177(8):5024-5031.

Cheng et al., "The influence of fibroblast growth factor 2 on the senescence of human adipose-derived mesenchymal stem cells during long-term culture," Stem Cells Transl. Medicine, Dec. 2019, 9(4):518-530.

Cox et al., "GM-CSF disruption in CART cells modulates T cell activation and enhances CART cell anti-tumor activity," Leukemia, 36:1635-1645, Apr. 19, 2022.

Cox et al., "Leukemic extracellular vesicles induce chimeric antigen receptor T cell dysfunction in chronic lymphocytic leukemia," Mol. Therapy, Jan. 2021, 29(4):1529-1540.

Dmitrieva et al., "Bone marrow- and subcutaneous adipose tissue-derived mesenchymal stem cells: differences and similarities," Cell Cycle, Jan. 2012, 11(2):377-383.

Dominici et al., "Minimal criteria for defining multipotent mesenchymal stromal cells. The International Society for Cellular Therapy position statement," Cytotherapy, Feb. 2006, 8(4):315-317.

Dorronsoro et al., "Human mesenchymal stromal cells modulate T-cell responses through TNF-α-mediated activation of NF-κB," Eur. J. Immunology, Dec. 2013, 44(2):480-488.

Dorronsoro et al., "Intracellular role of IL-6 in mesenchymal stromal cell immunosuppression and proliferation," Sci. Reports, Dec. 2020, 10(1):21853, 12 pages.

English et al., "IFN-γ and TNF-α differentially regulate immunomodulation by murine mesenchymal stem cells," Immunol. Letters, Apr. 2007, 110(2):91-100.

Estrada-Capetillo et al., "CD28 is expressed by macrophages with anti-inflammatory potential and limits their T-cell activating capacity," Eur. J. Immunology, Nov. 2020, 51(4):824-834.

Extended European Search Report in European Appln. No. 19780974.2, dated Nov. 30, 2021, 13 pages.

Extended European Search Report in European Appln. No. 19784411.1, dated Dec. 20, 2021, 11 pages.

Extended European Search Report in European Appln. No. 19880748.9, dated Jun. 29, 2022, 9 pages.

Fan et al., "Mesenchymal stem cells alleviate experimental autoimmune cholangitis through immunosuppression and cytoprotective function mediated by galectin-9," Stem Cell Res. Therapy, Sep. 2018, 9(1):237, 12 pages.

Fraietta et al., "Ibrutinib enhances chimeric antigen receptor T-cell engraftment and efficacy in leukemia," Blood, Mar. 2016, 127(9):1117-1127.

Gao et al., "Mesenchymal stem cells and immunomodulation: current status and future prospects," Cell Death Disease, Jan. 2016, 7:e2062, 11 pages.

GenBank Accession No. AB032738.1, "Homo sapiens gene for chemokine receptor CXCR3, partial cds," dated Jul. 26, 2016, 2 pages.

GenBank Accession No. AC003959.1, "Homo sapiens chromosome 5, P1 clone 1029A7 (LBNL H15), complete sequence," dated Jul. 24, 2016, 23 pages.

GenBank Accession No. AC011377.6, "Homo sapiens chromosome 5 clone CTB-120L21, complete sequence," dated Aug. 15, 2001, 13 pages.

GenBank Accession No. AF363458.1, "Homo sapiens programmed cell death 1 (PDCD1) gene, exons 1 through 5 and complete cds," dated Mar. 18, 2003, 4 pages.

GenBank Accession No. AL136985.11, "Human DNA sequence from clone RP11-63G10 on chromosome 1p32.1-32.3, complete sequence," dated Jan. 24, 2013, 33 pages.

GenBank Accession No. CH471059.2, "Homo sapiens 211000035844098 genomic scaffold, whole genome shotgun sequence," dated Mar. 23, 2015, 7 pages.

GenBank Accession No. CH471062.2, "Homo sapiens 211000035832302 genomic scaffold, whole genome shotgun sequence," dated Mar. 23, 2015, 6 pages.

GenBank Accession No. CQ834184.1, "Sequence 55 from Patent WO2004058805," dated Jul. 29, 2004, 2 pages.

GenBank Accession No. DQ789232.1, "Homo sapiens interferon regulatory factor-1 (IRF1) gene, promoter region and complete cds," dated Jul. 11, 2007, 3 pages.

GenBank Accession No. EF064716.1, "Homo sapiens programmed cell death 1 (PDCD1) gene, complete cds," dated Nov. 13, 2006, 7 pages.

GenBank Accession No. NM_000572.2, "Homo sapiens interleukin 10 (IL10), mRNA," dated Oct. 6, 2016, 3 pages.

GenBank Accession No. NM 000594.3, "Homo sapiens tumor necrosis factor (TNF), mRNA," dated Oct. 6, 2016, 4 pages.

GenBank Accession No. NM_000758.3, "Homo sapiens colony stimulating factor 2 (CSF2), mRNA," dated Jan. 16, 2016, 3 pages.

GenBank Accession No. NM_000759.3, "Homo sapiens colony stimulating factor 3 (CSF3), transcript variant 1, mRNA," dated Oct. 6, 2016, 4 pages.

GenBank Accession No. NM_001008540.2, "Homo sapiens C-X-C motif chemokine receptor 4 (CXCR4), transcript variant 1, mRNA," dated Apr. 8, 2017, 4 pages.

GenBank Accession No. NM_001142797.1, "Homo sapiens C-X-C motif chemokine receptor 3 (CXCR3), transcript variant 2, mRNA," dated Oct. 6, 2016, 4 pages.

GenBank Accession No. NM_001165412.1, "Homo sapiens nuclear factor kappa B subunit 1 (NFKB1), transcript variant 2, mRNA," dated May 18, 2016, 7 pages.

GenBank Accession No. NM_001319226.1, "Homo sapiens nuclear factor kappa B subunit 1 (NFKB1), transcript variant 3, mRNA," dated May 18, 2016, 7 pages.

(56) References Cited

OTHER PUBLICATIONS

GenBank Accession No. NM_001330163.1, "*Homo sapiens* galectin 9 (LGALS9), transcript variant 4, mRNA," dated Sep. 11, 2016, 3 pages.
GenBank Accession No. NM_001348056.1, "*Homo sapiens* C-X-C motif chemokine receptor 4 (CXCR4), transcript variant 3, mRNA," dated Apr. 8, 2017, 4 pages.
GenBank Accession No. NM_001348059.1, "*Homo sapiens* C-X-C motif chemokine receptor 4 (CXCR4), transcript variant 4, mRNA," dated Apr. 8, 2017, 4 pages.
GenBank Accession No. NM_001354924.1, "*Homo sapiens* interferon regulatory factor 1 (IRF1), transcript variant 2, mRNA," dated Aug. 29, 2017, 4 pages.
GenBank Accession No. NM_001354925.1, "*Homo sapiens* interferon regulatory factor 1 (IRF1), transcript variant 3, mRNA," dated Aug. 29, 2017, 4 pages.
GenBank Accession No. NM_001361665.1, "*Homo sapiens* fibroblast growth factor 2 (FGF2), mRNA," dated Mar. 28, 2018, 5 pages.
GenBank Accession No. NM_001382624.1, "*Homo sapiens* interleukin 10 (IL10), transcript variant 2, mRNA," dated May 18, 2020, 3 pages.
GenBank Accession No. NM_001382625.1, "*Homo sapiens* nuclear factor kappa B subunit 1 (NFKB1), transcript variant 4, mRNA," dated May 18, 2020, 8 pages.
GenBank Accession No. NM_001411087.1, "*Homo sapiens* RELB proto-oncogene, NF-kB subunit (RELB), transcript variant 2, mRNA," dated Aug. 22, 2022, 5 pages.
GenBank Accession No. NM_001504.1, "*Homo sapiens* C-X-C motif chemokine receptor 3 (CXCR3), transcript variant 1, mRNA," dated Oct. 6, 2016, 5 pages.
GenBank Accession No. NM_002006.4, "*Homo sapiens* fibroblast growth factor 2 (FGF2), mRNA," dated Oct. 6, 2016, 6 pages.
GenBank Accession No. NM_002198.2, "*Homo sapiens* interferon regulatory factor 1 (IRF1), mRNA," dated Aug. 12, 2016, 4 pages.
GenBank Accession No. NM_002228.3, "*Homo sapiens* Jun proto-oncogene, AP-1 transcription factor subunit (JUN), mRNA," dated Jan. 4, 2017, 6 pages.
GenBank Accession No. NM_002308.3, "*Homo sapiens* galectin 9 (LGALS9), transcript variant 2, mRNA," dated Sep. 10, 2016, 4 pages.
GenBank Accession No. NM_002986.2, "*Homo sapiens* C—C motif chemokine ligand 11 (CCL11), mRNA," dated Mar. 3, 2016, 4 pages.
GenBank Accession No. NM_005018.2, "*Homo sapiens* programmed cell death 1 (PDCD1), mRNA," dated Sep. 15, 2016, 4 pages.
GenBank Accession No. NM_006509.3, "*Homo sapiens* RELB proto-oncogene, NF-kB subunit (RELB), mRNA," dated May 1, 2016, 4 pages.
GenBank Accession No. NM_009587.2, "*Homo sapiens* galectin 9 (LGALS9), transcript variant 1, mRNA," dated Sep. 10, 2016, 4 pages.
GenBank Accession No. NM_032782.4, "*Homo sapiens* hepatitis A virus cellular receptor 2 (HAVCR2), mRNA," dated Sep. 1, 2016, 4 pages.
GenBank Accession No. NM_172219.2, "*Homo sapiens* colony stimulating factor 3 (CSF3), transcript variant 2, mRNA," dated Oct. 6, 2016, 4 pages.
Golovina et al., "CD28 costimulation is essential for human T regulatory expansion and function," J. Immunology, Aug. 2008, 181(4):2855-2868.
Guess et al., "Safety Profile of Good Manufacturing Practice Manufactured Interferon gamma—Primed Mesenchymal Stem/Stromal Cells for Clinical Trials," Stem Cells Transl. Medicine, Sep. 2017, 6(10):1868-1879.
Guo et al., "Interleukin-1β induces CXCR3-mediated chemotaxis to promote umbilical cord mesenchymal stem cell transendothelial migration," Stem Cell Res. Therapy, Oct. 2018, 9(1):281, 15 pages.
Guo et al., "NF-KappaB Pathway Is Involved in Bone Marrow Stromal Cell-Produced Pain Relief," Front. Integr. Neuroscience, Oct. 12, 2018:49, 10 pages.
Gyorgy et al., "Membrane vesicles, current state-of-the-art: emerging role of extracellular vesicles," Cell. Mol. Life Sciences, May 2011, 68(16):2667-2688.
Hacein-Bey et al., "A serious adverse event after successful gene therapy for X-linked severe combined immunodeficiency," N. Engl. J. Medicine, Jan. 2003, 348(3):255-266.
Haring et al., "Interfering With Inflammation: Heterogeneous Effects of Interferons in Graft-Versus-Host Disease of the Gastrointestinal Tract and Inflammatory Bowel Disease," Front. Immunology, Jun. 12, 2021:705342, 16 pages.
Harrell et al., "Mesenchymal Stem Cell-Derived Exosomes and Other Extracellular Vesicles as New Remedies in the Therapy of Inflammatory Diseases," Cells, Dec. 2019, 8(12):1605, 22 pages.
Hefazi et al., "Regulatory T Cell Therapy of Graft-versus-Host Disease: Advances and Challenges," Int. J. Mol. Sciences, Sep. 2021, 22(18):9676, 27 pages.
Howe et al., "Insertional mutagenesis combined with acquired somatic mutations causes leukemogenesis following gene therapy of SCID-XI patients," J. Clin. Investigation, Sep. 2008, 118(9):3143-3150.
Jutz et al., "Assessment of costimulation and coinhibition in a triple parameter T cell reporter line: Simultaneous measurement of NF-kappaB, NFAT and AP-1," J. Immunol. Methods, Jan. 2016, 430:10-20.
Kalimuthu et al., "In Vivo Tracking of Chemokine Receptor CXCR4-Engineered Mesenchymal Stem Cell Migration by Optical Molecular Imaging," Stem Cells International, Jun. 2017, 2017:8085637, 10 pages.
Kaltschmidt et al., "The Transcription Factor NF-kappaB in Stem Cells and Development," Cells, Aug. 2021, 10(8):2042, 17 pages.
Kanai et al., "Interferon-gamma enhances the therapeutic effect of mesenchymal stem cells on experimental renal fibrosis," Sci. Reports, Jan. 2021, 11(1):850, 14 pages.
Kim et al., "Enhanced Immunosuppressive Properties of Human Mesenchymal Stem Cells Primed by Interferon-gamma," EBioMedicine, Jan. 28, 2018:261-273.
Kim et al., "Galectin-9 is Involved in Immunosuppression Mediated by Human Bone Marrow-derived Clonal Mesenchymal Stem Cells," Immune Network, Oct. 2015, 15(5):241-251.
Kim et al., "MicroRNAs miR-125a and miR-125b constitutively activate the NF-κB pathway by targeting the tumor necrosis factor alpha-induced protein 3 (TNFAIP3, A20)," Proc. Natl. Acad. Sci. USA, May 2012, 109(20):7865-7870.
Lai et al., "Fibroblast growth factor 2 (Fgf2) inhibits differentiation of mesenchymal stem cells by inducing Twist2 and Spry4, blocking extracellular regulated kinase activation, and altering Fgf receptor expression levels," Stem Cells, Jul. 2011, 29(7):1102-1111.
Lamb et al., "Gut-Selective Integrin-Targeted Therapies for Inflammatory Bowel Disease," J. Crohns Colitis, Aug. 2018, 12(S2):S653-S668.
Lin et al., "Efficient lentiviral transduction of human mesenchymal stem cells that preserves proliferation and differentiation capabilities," Stem Cells Transl. Medicine, Nov. 2012, 1(12):886-897.
Lin et al., "Preconditioning of murine mesenchymal stem cells synergistically enhanced immunomodulation and osteogenesis," Stem Cell Res. Therapy, Dec. 8, 2017:277, 9 pages.
Lio et al., "CD28 facilitates the generation of Foxp3(-) cytokine responsive regulatory T cell precursors," J. Immunology, Apr. 2010, 184(11):6007-6013.
Liotta et al., "Toll-like receptors 3 and 4 are expressed by human bone marrow-derived mesenchymal stem cells and can inhibit their T-cell modulatory activity by impairing Notch signaling," Stem Cells, Oct. 2007, 26(1):279-289.
Liu et al., "Immunosuppressive Property of MSCs Mediated by Cell Surface Receptors," Front. Immunology, Jul. 11, 2020:1076, 15 pages.
Luz-Crawford et al., "Mesenchymal stem cells generate a CD4+ CD25+Foxp3+ regulatory T cell population during the differentiation process of Th1 and Th17 cells," Stem Cell Res. Therapy, Jun. 2013, 4(3):65, 12 pages.

(56) References Cited

OTHER PUBLICATIONS

Makita et al, "Clinical development of anti-CD19 chimeric antigen receptor T-cell therapy for B-cell non-Hodgkin lymphoma," Cancer Science, Jun. 2017, 108(6):1109-1118.
Melief et al., "Multipotent stromal cells induce human regulatory T cells through a novel pathway involving skewing of monocytes toward anti-inflammatory macrophages," Stem Cells, Sep. 2013, 31(9):1980-1991.
Molinero et al., "High TCR stimuli prevent induced regulatory T cell differentiation in a NF-kappaB-dependent manner," J. Immunology, Mar. 2011, 186(8):4609-4617.
Murata et al., "Off-the-shelf bone marrow-derived mesenchymal stem cell treatment for acute graft-versus-host disease: real-world evidence," Bone Marrow Transplantation, May 2021, 56(10):2355-2366.
Naji et al., "Biological functions of mesenchymal stem cells and clinical implications," Cell. Mol. Life Sciences, May 2019, 76(17):3323-3348.
Niu et al., "TLR-4/microRNA-125a/NF-κB signaling modulates the immune response to *Mycobacterium tuberculosis* infection," Cell Cycle, Sep. 2018, 17(15):1931-1945.
Noronha et al., "Priming approaches to improve the efficacy of mesenchymal stromal cell-based therapies," Stem Cell Res. Therapy, May 10, 2019:131, 21 pages.
Noyan et al., "Prevention of Allograft Rejection by Use of Regulatory T Cells With an MHC-Specific Chimeric Antigen Receptor," Am. J. Transplantation, Feb. 2017, 17(4):917-930.
Office Action in European Appln. No. 19780974.2, dated Jul. 11, 2023, 14 pages.
Orabona et al., "CD28 induces immunostimulatory signals in dendritic cells via CD80 and CD86," Nat. Immunology, Oct. 2004, 5(11):1134-1142.
Ouyang et al., "Novel Foxo1-dependent transcriptional programs control T(reg) cell function," Nature, Nov. 2012, 491(7425):554-559, 8 pages.
Patsoukis et al., "Revisiting the PD-1 pathway," Sci. Advances, Sep. 2020, 6(38):eabd2712, 14 pages.
PCT International Preliminary Report on Patentability in International Appln. No. PCT/US2019/026108, mailed on Oct. 15, 2020, 7 pages.
PCT International Preliminary Report on Patentability in International Appln. No. PCT/US2019/026544, mailed on Oct. 22, 2020, 7 pages.
PCT International Preliminary Report on Patentability in International Appln. No. PCT/US2019/059113, mailed on May 14, 2021, 9 pages.
PCT International Preliminary Report on Patentability in International Appln. No. PCT/US2020/059720, mailed on May 19, 2022, 11 pages.
PCT International Search Report and Written Opinion in International Appln. No. PCT/US2019/026108, mailed on Jun. 11, 2019, 13 pages.
PCT International Search Report and Written Opinion in International Appln. No. PCT/US2019/026544, mailed on Jun. 27, 2019, 10 pages.
PCT International Search Report and Written Opinion in International Appln. No. PCT/US2019/059113, mailed on Jan. 31, 2020, 18 pages.
PCT International Search Report and Written Opinion in International Appln. No. PCT/US2020/059720, mailed on Mar. 12, 2021, 15 pages.
PCT International Search Report and Written Opinion in International Appln. No. PCT/US2022/028139, mailed on Aug. 30, 2022, 14 pages.
Phinney et al., "MSCs: science and trials," Nat. Medicine, Jul. 2013, 19(7):812.
Ping et al., "Activation of NF-κB driven inflammatory programs in mesenchymal elements attenuates hematopoiesis in low-risk myelodysplastic syndromes," Leukemia, Oct. 2018, 33(2):536-541.
Pittenger et al., "Multilineage potential of adult human mesenchymal stem cells," Science, Apr. 1999, 284(5411):143-147.
Ponten et al., "The Human Protein Atlas—a tool for pathology," J Pathol, Sep. 2008, 216(4):387-393.
Potenza et al., "Molecular mechanisms governing microRNA-125a expression in human hepatocellular carcinoma cells," Sci. Reports, Sep. 7, 2017:10712, 9 pages.
Prasanna et al., "Pro-Inflammatory Cytokines, IFNc and TNFa, Influence Immune Properties of Human Bone Marrow and Wharton Jelly Mesenchymal Stem Cells Differentially," PLoS One, Feb. 2010, 5(2):e9016, 16 pages.
Puissant et al., "Immunomodulatory effect of human adipose tissue-derived adult stem cells: comparison with bone marrow mesenchymal stem cells," Br. J. Haematology, Apr. 2005, 129(1):118-129.
Riches et al., "T cells from CLL patients exhibit features of T-cell exhaustion but retain capacity for cytokine production," Blood, Feb. 2013, 121(9):1612-1621.
Sakemura et al., "Development of a Clinically Relevant Reporter for Chimeric Antigen Receptor T-cell Expansion, Trafficking, and Toxicity," Cancer Immunol. Research, Jul. 2021, 9(9):1035-1046.
Sakemura et al., "Resistance to CART cell therapy: lessons learned from the treatment of hematological malignancies," Leuk. Lymphoma, Mar. 2021, 62(9):2052-2063.
Sarkar et al., "Engineered cell homing," Blood, Oct. 2011, 118(25):e184-e191.
Schmitz et al., "Controlling NF-κB activation in T cells by costimulatory receptors," Cell Death Differentiation, Jan. 13, 2006:834-842.
Scholler et al., "Decade-long safety and function of retroviral-modified chimeric antigen receptor T cells," Sci. Transl. Medicine, May 2012, 4(132):1-7, 43 pages.
Shi et al., "Immunoregulatory mechanisms of mesenchymal stem and stromal cells in inflammatory diseases," Nat. Rev. Nephrology, Aug. 2018, 14(8):493-507.
Sirpilla et al., "Chimeric Antigen Receptor Engineering of Mesenchymal Stromal Cells (CAR-MSC) Enhance Immunosuppression and Outcomes in Graft Versus Host Disease (GvHD) Preclinical Models," Blood, Nov. 2022, 140(S1):1579-1580, 7 pages.
Smith et al., "miR-29ab1 deficiency identifies a negative feedback loop controlling Th1 bias that is dysregulated in multiple sclerosis," J. Immunology, Aug. 2012, 189(4):1567-1576.
Steiner et al., "MicroRNA-29 regulates T-box transcription factors and interferon-γ production in helper T cells," Immunity, Aug. 2011, 35(2):169-181.
Strauss et al., "Targeted deletion of PD-1 in myeloid cells induces antitumor immunity," Sci. Immunology, Jan. 2020, 5(43):1-14.
Teshima et al., "Acute Graft-versus-Host Disease: Novel Biological Insights," Biol. Blood Marrow Transplantation, Oct. 2015, 22(1):11-16.
Thaker et al., "TCR and CD28 activate the transcription factor NF-kappaB in T-cells via distinct adaptor signaling complexes," Immunol. Letters, Oct. 2014, 163(1):113-119.
Thiele et al., "miR-9 enhances IL-2 production in activated human CD4(+) T cells by repressing Blimp-1," Eur. J. Immunology, Aug. 2012, 42(8):2100-2108.
Uccelli et al., "Mesenchymal stem cells in health and disease," Nat. Rev. Immunology, Sep. 2008, 8(9):726-736.
Wang et al., "NF-kB-YY1-miR-29 Regulatory Circuitry in Skeletal Myogenesis and Rhabdomyosarcoma," Cancer Cell, Nov. 2008, 14(5):369-381.
Wu et al., "MicroRNA Roles in the Nuclear Factor Kappa B Signaling Pathway in Cancer," Front. Immunology, Mar. 2018, 9:546, 9 pages.
Yañez et al., "Improved efficacy of mesenchymal stromal cells stably expressing CXCR4 and IL-10 in a xenogeneic graft versus host disease mouse model," Front Immunol., Feb. 14, 2023:1-15.
Zeng et al., "miR-9 enhances the transactivation of nuclear factor of activated T cells by targeting KPNB1 and DYRK1B," Am. J. Physiol. Cell Physiology, May 2015, 308(9):C720-C728.
Zhao et al., "Galectin-9 Mediates the Therapeutic Effect of Mesenchymal Stem Cells on Experimental Endotoxemia," Front. Cell Dev. Biology, Feb. 2022, 10:700702, 17 pages.

(56) References Cited

OTHER PUBLICATIONS

Zheng et al., "MIR-125b regulates proliferation and apoptosis of nasopharyngeal carcinoma by targeting A20/NF-κB signaling pathway," Cell Death Disease, Jun. 2017, 8(6):e2855, 13 pages.

Academic Press Dictionary of Science and Technology (definition for the term "polyclonal"; Oxford: Elsevier Science & Technology (1996); retrieved Oct. 22, 2008, from http://www.credoreference.com/entry/3144515/.

Acsadi et al., "Direct gene transfer and expression into rat heart in vivo," New Biol., 3(1):71-81, Jan. 1991.

Adachi et al., "Enhanced and accelerated lymphoproliferation in Fas-null micc.," Proc Natl Acad Sci USA., 93(5):2131-2136, Mar. 5, 1996.

Adachi et al., "Aberrant transcription caused by the insertion of an early transposable element in an intron of the Fas antigen gene of lpr mice," Proc Natl Acad Sci USA., 90(5):1756-1760, Mar. 1, 1993.

Adada et al., "906: Favorable Modulation of Chimeric Antigen Receptor T Cells Safety and Efficacy By the Non-Covalent BTK Inhibitor Vecabrutinib," Abstract, Presented at Proceedings of the American Society of Hematology Annual Meeting & Exposition, Dec. 11-14, 2021, Atlanta, GA, USA, 3 pages.

Afonina et al., "Cytotoxic and non-cytotoxic roles of the CTL/NK protease granzyme B," Immunol Rev., 235(1):105-116, May 2010.

Agata et al., "Expression of the PD-I antigen on the surface of stimulated mouse T and B lymphocytes," Int Immunol., 8(5):765-772, May 1996.

Ahmadzadeh et al., "Tumor antigen-specific CD8 T cells infiltrating the tumor express high levels of PD-1 and are functionally impaired," Blood, 114(8):1537-1544, May 7, 2009.

Ahonen et al., "Combined TLR and CD40 triggering induces potent CD8+ T cell expansion with variable dependence on type I IFN," J Exp Med., 199(6):775-784, Mar. 8, 2004.

Alderson et al., "Molecular and biological characterization of human 4-1BB and its ligand," Eur J Immunol., 24(9):2219-2227, Sep. 1994.

Aldovini et al., "Humoral and cell-mediated immune responses to live recombinant BCG-HIV vaccines," Nature, 351(6326):479-482, Jun. 6, 1991.

Alizadeh et al., "Chemotherapeutic targeting of cancer-induced immunosuppressive cells," Cancer Res., 74(10):2663-2668, May 15, 2014.

Allie et al., "Programmed death 1 regulates development of central memory CD8 T cells after acute viral infection," J Immunol., 186(11):6280-6286, Apr. 27, 2011.

Altin et al.. "The role of CD45 and CD45-associated molecules in T cell activation," Immunol. Cell Biology, 75(5):430-445, Oct. 1997.

Ambrosini et al., "A novel anti-apoptosis gene, survivin, expressed in cancer and lymphoma," Nat Med., 3(8):917-921, Aug. 1997.

Anders et al., "HTSeq—a Python framework to work with high-throughput sequencing data," Bioinformatics, 31(2):166-169, Jan. 15, 2015.

Anderson, "Human gene therapy," Science, 256(5058):808-813, May 8, 1992.

Andorsky et al., "Programmed death ligand 1 is expressed by non-hodgkin lymphomas and inhibits the activity of tumor-associated T cells," Clin Cancer Res., 17(13):4232-4244, May 3, 2011.

Anikeeva et al., "Distinct role of lymphocyte function-associated antigen-1 in mediating effective cytolytic activity by cytotoxic T lymphocytes," Proc Natl Acad Sci USA., 102(18):6437-6442, Apr. 25, 2005.

Ansari et al., "The programmed death-1 (PD-1) pathway regulates autoimmune diabetes in nonobese diabetic (NOD) mice," J Exp Med., 198(1):63-69, Jul. 7, 2003.

Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," Microbes Infect., 8(6):1450-1454, Mar. 29, 2006.

Attwood et al., "Genomics. The Babel of bioinformatics," Science, 290(5491):471-473, Oct. 20, 2000.

Azuma et al., "B7—H1 is a ubiquitous antiapoptotic receptor on cancer cells," Blood., 111(7):3635-3643, Jan. 25, 2008.

Baitsch et al., "Exhaustion of tumor-specific CD8+ T cells in metastases from melanoma patients," J Clin Invest., 121(6):2350-2360, May 9, 2011.

Bajorath et al., "Molecular modeling of CD28 and three-dimensional analysis of residue conservation in the CD28/CD152 family," J Mol Graph Model., 15(2):135-139, 108-111, Apr. 1997.

Baldrick, "Pharmaceutical excipient development: the need for preclinical guidance," Regul Toxicol Pharmacol., 32(2):210-218, Oct. 2000.

Banáth et al., "Residual gammaH2AX foci as an indication of lethal DNA lesions," BMC Cancer., 10:4, Jan. 5, 2010.

Barber et al., "Restoring function in exhausted CD8 T cells during chronic viral infection," Nature, 439(7077):682-687, Dec. 28, 2005.

Barlic et al., "IL-15 and IL-2 oppositely regulate expression of the chemokine receptor CX3CR1," Blood, 102(10):3494-3503, Nov. 15, 2003.

BD PharmingenTM Technical Data Sheet, "Purified Rat Anti-Mouse Ly-6G (Gr-1) Monoclonal Antibody for Immunohistochemistry (IHC)" 1 page, 2003.

Benita et al., "Characterization of drug-loaded poly(d,l-lactide) microspheres," J Pharm Sci., 73(12):1721-1724, Dec. 1984.

Benlalam et al., "Comprehensive analysis of the frequency of recognition of melanoma-associated antigen (MAA) by CD8 melanoma infiltrating lymphocytes (TIL) implications for immunotherapy," Eur J Immunol., 31(7):2007-2015, Jul. 31, 2001.

Bennardo et al., "Alternative-NHEJ is a mechanistically distinct pathway of mammalian chromosome break repair," PLoS Genet., 4(6):e1000110, Jun. 27, 2008.

Berman et al., "The Protein Data Bank," Nucleic Acids Res., 28(1):235-242, Jan. 1, 2000.

Berrien-Elliott et al., "Durable adoptive immunotherapy for leukemia produced by manipulation of multiple regulatory pathways of CD8+ T-cell tolerance," Cancer Res., 73(2):605-616, Jan. 15, 2013.

Berthon et al., "In acute myeloid leukemia, B7-H1 (PD-L1) protection of blasts from cytotoxic T cells is induced by TLR ligands and interferon-gamma and can be reversed using MEK inhibitors," Cancer Immunol Immunother., 59(12):1839-1849, Sep. 4, 2010.

Betts et al., "Sensitive and viable identification of antigen-specific CD8+ T cells by a flow cytometric assay for degranulation," J Immunol Methods, 281(1-2):65-78, Oct. 1, 2003.

Bezu et al., "Combinatorial strategies for the induction of immunogenic cell death," Front Immunol., 6:187, Apr. 24, 2015, 11 pages.

Bibikova et al., "Enhancing gene targeting with designed zinc finger nucleases," Science, May 2, 2003, 300(5620):764.

Bird et al., "Single-chain antigen-binding proteins," Science, 242(4877):423-426, Oct. 21, 1988.

Bitinaite et al., "FokI dimerization is required for DNA cleavage," Proc. Natl. Acad. Sci. USA, Sep. 1, 1998, 95(18):10570-10575.

Black et al., "Activation of the PD-1/PD-L1 immune checkpoint confers tumor cell chemoresistance associated with increased metastasis," Oncotarget, 7(9):10557-10567, Mar. 2016.

Blank et al., "Blockade of PD-L1 (B7—H1) augments human tumor-specific T cell responses in vitro," Int J Cancer, 119(2):317-327, Jul. 15, 2006.

Blank et al., "Interaction of PD-L1 on tumor cells with PD-1 on tumor-specific T cells as a mechanism of immune evasion: implications for tumor immunotherapy," Cancer Immunol Immunother., 54(4):307-314, Dec. 15, 2004.

Blank et al., "PD-L1/B7H-1 inhibits the effector phase of tumor rejection by T cell receptor (TCR) transgenic CD8+ T cells," Cancer Res., 64(3):1140-1145, Feb. 1, 2004.

Blazar et al., "Infusion of anti-B7.1 (CD80) and anti-B7.2 (CD86) monoclonal antibodies inhibits murine graft-versus-host disease lethality in part via direct effects on CD4+ and CD8+ T cells, " J Immunol., 157(8):3250-3259, Oct. 15, 1996.

(56) References Cited

OTHER PUBLICATIONS

Block, "Medicated Applications," Remington's Pharmaceutical Sciences, 18th edition, Mack Publishing Company, Easton, PA, Chpt 87, pp. 1596-1614, 1990.
Bodine, "mTOR signaling and the molecular adaptation to resistance exercise," Med Sci Sports Exerc., 38(11):1950-1957, Nov. 2006.
Boggio et al., "Interleukin 12-mediated prevention of spontaneous mammary adenocarcinomas in two lines of Her-2/neu transgenic mice," J Exp Med., 188(3):589-596, Aug. 3, 1998.
Boise et al., "CD28 costimulation can promote T cell survival by enhancing the expression of Bcl-XL," Immunity, 3(1):87-98, Jul. 1995.
Boletta et al., "High efficient non-viral gene delivery to the rat kidney by novel polycationic vectors," J Am Soc Nephrol., 7(9):1728, abstr A2409, Sep. 1, 1996.
Bolger et al., "Trimmomatic: a flexible trimmer for Illumina sequence data," Bioinformatics, 30(15):2114-2120, Aug. 1, 2014.
Bona et al., "Immune response: Idiotype anti-idiotype network," CRC Crit Rev Immunol., 33-81, Mar. 1981.
Bonfoco et al., "Inducible nonlymphoid expression of Fas ligand is responsible for superantigen-induced peripheral deletion of T cells," Immunity, 9(5):711-720, Nov. 1998.
Bonifaz et al., "Efficient targeting of protein antigen to the dendritic cell receptor DEC-205 in the steady state leads to antigen presentation on major histocompatibility complex class 1 products and peripheral CD8+ T cell tolerance, " J Exp Med., 196(12):1627-1638, Dec. 16, 2002.
Bonifaz et al., "In vivo targeting of antigens to maturing dendritic cells via the DEC-205 receptor improves T cell vaccination," J Exp Med., 199(6):815-824, Mar. 15, 2004.
Bonni et al., "Cell survival promoted by the Ras-MAPK signaling pathway by transcription-dependent and -independent mechanisms," Science, 286(5443):1358-1362, Nov. 12, 1999.
Boon et al., "Human T cell responses against melanoma," Annu Rev Immunol., 24:175-208, 2006.
Borson et al., "Brain-infiltrating cytolytic T lymphocytes specific for Theiler's virus recognize H2Db molecules complexed with a viral VP2 peptide lacking a consensus anchor residue," J Virol., 71(7):5244-5250, Jul. 1997.
Bottcher et al., "Functional classification of memory CD8(+) T cells by CX3CR1 expression," Nat Commun., 6:8306, Sep. 25, 2015.
Bouillet and O'Reilly, "CD95, BIM and T cell homeostasis," Nat Rev Immunol., 9(7):514-519, Jul. 2009.
Bowie et al., "Deciphering the message in protein sequences: tolerance to amino acid substitutions," Science, 247(4948):1306-1310, Mar. 16, 1990.
Boysen et al., "Dynamics of microvesicle generation in B-cell chronic lymphocytic leukemia: implication in disease progression," Leukemia, 31(2):350-360, Aug. 2, 2016.
Brahmer et al., "Safety and activity of anti-PD-LI antibody in patients with advanced cancer," N Engl J Med., 366(26):2455-2465, Jun. 2, 2012.
Brand et al., "Collagen-induced arthritis," Nat. Protoc., 2(5):1269-1275, May 17, 2007.
Braquet et al., "Effect of endothelin-1 on blood pressure and bronchopulmonary system of the guinea pig," J Cardiovasc Pharmacol., 13(Suppl 5):S143-146, discussion S150, 1989.
Brinkmann et al., "FTY720: altered lymphocyte traffic results in allograft protection," Transplantation., 72(5):764-769, Sep. 15, 2001.
Britton et al., "Leprosy," Lancet, 363(9416):1209-1219, Apr. 10, 2004.
Brooks, "Translational genomics: the challenge of developing cancer biomarkers," Genome Res., 22(2):183-187, Feb. 2012.
Brown et al., "A mass spectrometry-based assay for improved quantitative measurements of efflux pump inhibition," PLoS One, 10(5):e0124814, May 11, 2015, 12 pages.
Brown et al., "Blockade of programmed death-1 ligands on dendritic cells enhances T cell activation and cytokine production.," J Immunol., 170(3):1257-1266, Feb. 1, 2003.

Brown et al., "CAR T cell therapy: inroads to response and resistance," Nat. Rev. Immunology, 19(2):73-74, Jan. 10, 2019.
Brozovic et al., "Activation of mitogen-activated protein kinases by cisplatin and their role in cisplatin-resistance," Cancer Lett., 251(1):1-16, Nov. 27, 2006.
Bu et al., "Learning from PD-1 Resistance: New Combination Strategies," Trends Mol Med., 22(6):448-451, Jun. 2016.
Bubenik, "Genetically engineered dendritic cell-based cancer vaccines (Review)," Int J Oncol., 18(3):475-478, Mar. 2001.
Burmer et al, "Frequency and spectrum of c-Ki-ras mutations in human sporadic colon carcinoma, carcinomas arising in ulcerative colitis, and pancreatic adenocarcinoma," Environ Health Perspect., 93:27-31, Jun. 1991.
businesswire.com [online], "Incyte Reports Third Quarter 2011 Financial Results and Provides Update on Key Clinical Programs," Oct. 27, 2011, retrieved on Mar. 24, 2021, retrieved from URL<https://www.businesswire.com/news/home/20111027005220/en/Incyte-Reports-Third-Quarter-2011-Financial-Results-and-Provides-Update-on-Key-Clinical-Programs>, 4 pages.
Buskens et al, "Adenocarcinomas of the gastro-esophageal junction: A comparative study of the gastric cardia and the esophagus with respect to cyclooxygenase-2 expression," Digestive Disease Week Abstracts and Itinerary Planner, abstract No. 850, 2003.
Butte et al., "Interaction of human PD-L1 and B7-1," Mol Immunol., 45(13):3567-3572, Jun. 27, 2008.
Butte et al., "PD-L1 interacts specifically with B7-1 to inhibit T cell proliferation," Immunity., 27:111-122, 2007.
Cairns et al., "Immortalization of multipotent growth-factor dependent hemopoietic progenitors from mice transgenic for GATA-I driven SV40 tsA58 gene," EMBO J., 13(19):4577-4586, Oct. 3, 1994.
Cannons et al., "4-1BB ligand induces cell division, sustains survival, and enhances effector function of CD4 and CD8 T cells with similar efficacy," J Immunol., 167(3):1313-1324, Aug. 1, 2001.
Cao et al., "B7—H1 overexpression regulates epithelial-mesenchymal transition and accelerates carcinogenesis in skin," Cancer Res., 71(4):1235-1243, Dec. 15, 2010.
Carreno et al., "The B7 family of ligands and its receptors: new pathways for costimulation and inhibition of immune responses," Annu Rev Immunol., 20:29-53, Oct. 4, 2001.
Carter et al., "PD-1:PD-L inhibitory pathway affects both CD4(+) and CD8(+) T cells and is overcome by IL-2," Eur J Immunol., 32(3):634-643, Mar. 2002.
Carter et al., "Humanization of an anti-p185HER2 antibody for human cancer therapy," Proc Natl Acad Sci USA., 89(10):4285-4289, May 15, 1992.
Catalano et al., "Inhibiting extracellular vesicles formation and release: a review of EV inhibitors," J. Extracell. Vesicles, 9(1):1703244, Dec. 19, 2019, 22 pages.
Chakrabarti et al., "Vaccinia virus expression vector: coexpression of beta-galactosidase provides visual screening of recombinant virus plaques," Mol Cell Biol., 5(12):3403-3409, Dec. 1985.
Chambers et al., "Co-stimulation in T cell responses," Curr Opin Immunol., 9(3):396-404, Jun. 1997.
Champiat et al., "Hyperprogressive Disease Is a New Pattern of Progression in Cancer Patients Treated by Anti-PD-1/PD-L1," Clin Cancer Res., 23(8):1920-1928, Apr. 15, 2017.
Chan et al., "Arthritis and Tenosynovitis Associated With the Anti-PD1 Antibody Pembrolizumab in Metastatic Melanoma," J. Immunother., 38(1):37-39, Jan. 2015.
Chan et al., "Autophosphorylation of the DNA-dependent protein kinase catalytic subunit is required for rejoining of DNA double-strand breaks," Genes Dev., 16(18):2333-2338, Sep. 15, 2002.
Chapoval et al., "B7—H3: A costimulatory molecule for T cell activation and IFN-y production," Nat Immunol., 2(3):269-274, Mar. 2001.
Charman, "Lipids, lipophilic drugs, and oral drug delivery-some emerging concepts," J. Pharm. Sci., 89(8):967-978, Aug. 2000.
Chaurand et al., "Peptide and Protein Identification by Matrix-Assisted Laser Desorption Ionization (MALDI) and MALDI-Post-Source Decay Time-of-Flight Mass Spectrometry," J Am Soc Mass Spectrom., 10(2):91-103, Feb. 1999.

(56) References Cited

OTHER PUBLICATIONS

Chen et al., "Anti-PD-1/PD-L1 therapy of human cancer: past, present, and future," J. Clin. Investigation, 125(9):3384-3391, Sep. 2015.
Chen et al., "CD44-deficient mice exhibit enhanced hepatitis after concanavalin A injection: evidence for involvement of CD44 in activation-induced cell death," J Immunol., 166(10):5889-5897, May 1, 2001.
Chen et al., "Costimulation of antitumor immunity by the B7 counterreceptor of the T lymphocyte molecules CD28 and CTLA-4," Cell, 71(7):1093-1102, Dec. 24, 1992.
Chen et al., "Development of a sandwich ELISA for evaluating soluble PD-L1 (CD274) in human sera of different ages as well as supernatants of PD-L1+ cell lines," Cytokine, 56(2):231-238, Nov. 2011.
Chen et al., "Molecular Pathways: Next-Generation Immunotherapy—Inhibiting Programmed Death-Ligand 1 and Programmed Death-1," Clin. Cancer Research, 18(24):6580-6587, Oct. 19, 2012.
Chen et al., "PD-L1 Expression Promotes Epithelial to Mesenchymal Transition in Human Esophageal Cancer," Cell Physiol. Biochemistry, 42(6):2267-2280, Aug. 17, 2017.
Chen et al., "Tumor immunogenicity determines the effect of co-stimulation by B7 on T-cell mediated tumor immunity," J Exp Med., 179(2):523-532, Feb. 1, 1994.
Chen et al., "Upregulation of PD-L1 by EGFR Activation Mediates the Immune Escape in EGFR- Driven NSCLC: Implication for Optional Immune Targeted Therapy for NSCLC Patients with EGFR Mutation," J. Thorac. Oncology, 10(6):910-923, Jun. 2015.
Chen, "Co-inhibitory molecules of the B7-CD28 family in the control of T-cell immunity," Nat Rev Immunol., 4(5):336-347, May 2004.
Cheville et al., "Comparisons of outcome and prognostic features among histologic subtypes of renal cell carcinoma," Am J Surg Pathol., 27(5):612-624, May 2003.
Cho et al., "Targeted genome engineering in human cells with the Cas9 RNA-guided endonuclease," Nat. Biotechnology, 31(3):230-232, Jan. 29, 2013.
Choi et al., "Genomic Organization and expression Analysis of B7—H4, an Immune Inhibitory Molecule of the B7 Family," J Immunol., 171(9):4650-4654, Nov. 1, 2003.
Chowdhury et al., "Programmed death-ligand 1 overexpression is a prognostic marker for aggressive papillary thyroid cancer and its variants," Oncotarget, 7(22):32318-32328, May 31, 2016.
Chung et al., "Seeding Open Innovation Drug Discovery and Translational Collaborations to Leverage Government Funding: A Case Study of Strategic Partnership between Sanford-Burnham and Mayo Clinic," Collaborative Innovation in Drug Discovery: Strategies for Public and Private Partnerships, 27:451-486, Apr. 2014.
ClinicalTrials.gov [online], "Safety, PK, PD, and Antitumor Activity of Vecabrutinib (SNS-062) in B Lymphoid Cancers," NCT03037645, last updated Oct. 19, 2020, retrieved on Jan. 5, 2022, retrieved from URL<https://clinicaltrials.gov/ct2/show/NCT03037645>, 21 pages.
Cocuzza et al., "[Importance and evaluation of red cell indices obtained with semi-automatic cell counters during the screening of heterozygote beta-thalassemia]," Minerva Med, 74(18):1017-1020, Apr. 28, 1983 (with Machine English Abstract).
Cogoni et al., "Gene silencing in Neurospora crassa requires a protein homologous to RNA-dependent RNA polymerase, " Nature, 399(6732):166-169, May 13, 1999.
Cogoni et al., "Transgene silencing of the al-1 gene in vegetative cells of Neurospora is mediated by a cytoplasmic effector and does not depend on DNA-DNA interactions or DNA methylation ," EMBO J., 15(12):3153-3163, Jun. 17, 1996.
Cohen et al., "Lpr and gld: Single Gene Models of Systemic Autoimmunity and Lymphoproliferative Disease," Annu Rev Immunol., 9:243-269, 1991.
Colado et al., "Effect of the BTK inhibitor ibrutinib on macrophage- and gammadelta T cell-mediated response against *Mycobacterium tuberculosism*" Blood Cancer Journal, Nov. 5, 2018, 8(11):100, 6 pages.

Cole et al., "The EBV-hybridoma technique and its application to human lung cancer," Monoclonal Antibodies and Cancer Therapy, 27:77-96, Jan./Feb. 1985.
Collins et al., "The B7 family of immune-regulatory ligands," Genome Biol., 6(6):223, May 31, 2005, 7 pages.
Collis et al., "The life and death of DNA-PK," Oncogene., 24(6):949-961, Feb. 3, 2005.
Conacci-Sorrell et al., "Autoregulation of E-cadherin expression by cadherin-cadherin interactions: the roles of beta-catenin signaling, Slug, and MAPK," J Cell Biol., 163(4):847-857, Nov. 17, 2003.
Cone et al., "High-efficiency gene transfer into mammalian cells: generation of helper-free recombinant retrovirus with broad mammalian host range," Proc Natl Acad Sci USA., 81(20):6349-6353, Oct. 1984.
Cong et al., "Multiplex genome engineering using CRISPR/Cas systems," Science, 339(6121):819-823, Jan. 3, 2013.
Connolly, "Analytical molecular surface calculation," J Appl Crystallogr., 16(5):548-558, Oct. 1, 1983.
Cooley et al., "Trans-presentation of IL-15 modulates STAT5 activation and Bcl-6 expression in TH1 cells," Sci Rep, 5:15722, Oct. 26, 2015, 9 pages.
Corpet, "Multiple sequence alignment with hierarchical clustering," Nucleic Acids Res., 16(22):10881-10890, Nov. 25, 1988.
Cote et al., "Generation of human monoclonal antibodies reactive with cellular antigens," Proc Natl Acad Sci USA., 80(7):2026-2030, Apr. 1983.
Coumans et al., "Methodological Guidelines to Study Extracellular Vesicles," Circ. Research, 120(10):1632-1648, May 12, 2017.
Coyle et al., "The expanding B7 superfamily: increasing complexity in costimulatory signals regulating T cell function," Nat Immunol., 2(3):203-209, Mar. 2001.
Crispe et al., "The liver as a site of T-cell apoptosis: graveyard, or killing field?" Immunol Rev., 174:47-62, Apr. 2000.
Crispe, "Hepatic T cells and liver tolerance," Nat Rev Immunol., 3(1):51-62, Jan. 2003.
Cristiano et al., "Molecular conjugates: a targeted gene delivery vector for molecular medicine," J Mol Med (Berl)., 73(10):479-486, Oct. 1995.
Cruz-Guilloty et al., "Runx3 and T-box proteins cooperate to establish the transcriptional program of effector CTLs," J. Exp. Med., 206(1):51-59, Jan. 16, 2009.
Crystal, "Gene therapy strategies for pulmonary disease" Am J Med., 92(suppl 6A):44S-52S, Jun. 22, 1992.
Curiel et al., "Blockade of B7—H1 improves myeloid dendritic cell-mediated antitumor immunity," Nat Med., 9(5):562-567, Apr. 21, 2003.
Daly et al., "Clinical Trials Integrating Immunotherapy and Radiation for Non-Small-Cell Lung Cancer," J. Thorac. Oncology, 10(12):1685-1693, Dec. 1, 2015.
Daniele et al., "A role for Rab7 in the movement of secretory granules in cytotoxic T lymphocytes," Traffic, 12(7):902-911, Jul. 2011.
Dao et al., "Involvement of CD1 in peripheral deletion of T lymphocytes is independent of NK T cells," J Immunol., 166(5):3090-3097, Mar. 1, 2001.
Database EM-MUS [Online]EMBL; Accession No. AF142780.1 (version 1), Jun. 1, 1999, 2 pages.
Datta et al., "Akt phosphorylation of BAD couples survival signals to the cell-intrinsic death machinery," Cell., 91(2):231-241, Oct. 17, 1997.
Daud et al., "Tumor immune profiling predicts response to anti-PD-1 therapy in human melanoma," J. Clin. Invest., 126(9):3447-3452, Sep. 1, 2016.
Davidson et al., "Phenotypic, functional, and molecular genetic comparisons of the abnormal lymphoid cells of C3H-lpr/lpr and C3H-gld/gld mice," J Immunol., 136(11):4075-4084, Jun. 1, 1986.
Davidson et al., "Small Molecules, Inhibitors of DNA-PK, Targeting DNA Repair, and Beyond," Front Pharmacol., 4(5):1-7, Jan. 31, 2013.
Davis et al., "Proline 326 in the C terminus of murine CX3CR1 prevents G-protein and phosphatidylinositol 3-kinase-dependent

(56) References Cited

OTHER PUBLICATIONS stimulation of Akt and extracellular signal-regulated kinase in Chinese hamster ovary cells," J. Pharmacol. Exp. Ther., 316(1):356-363, Jan. 2006.
De StGroth et al., "Production of monoclonal antibodies: strategy and tactics," J Immunol Methods., 35(1-2):1-21, 1980.
Debs et al., "Lung-specific delivery of cytokines induces sustained pulmonary and systemic immunomodulation in rats," J Immunol., 140(10):3482-3488, May 15, 1988.
Del Peso et al., "Interleukin-3-induced phosphorylation of BAD through the protein kinase Akt," Science, 278(5338):687-689, Oct. 24, 1997.
Dezutter-Dambuyan et al., "A novel regulation of PD-1 ligands on mesenchymal stromal cells through MMP-mediated proteolytic cleavage," OncoImmunology, 5(3):e1091146, Mar. 2016, 24 pages.
Dheda et al., "Lung remodeling in tuberculosis," J Infect Dis., 192(7):1201-1209, Aug. 29, 2005.
Dicarlo et al., "Genome engineering in *Saccharomyces cerevisiae* using CRISPR-Cas systems," Nucleic Acids Research, 41(7):4226-4343, Mar. 4, 2013.
Diehl et al., "In vivo triggering through 4-1BB enables Th-independent priming of CTL in the presence of an intact CD28 costimulatory pathway," J Immunol., 168(8):3755-3762, Apr. 15, 2002.
Ding et al., "Release of reactive nitrogen intermediates and reactive oxygen intermediates from mouse peritoneal macrophages. Comparison of activating cytokines and evidence for independent production," J Immunol., 141(7):2407-2412, Oct. 1, 1988.
Dini, "Recognizing death: liver phagocytosis of apoptotic cells," Eur J Histochem., 44(3):217-227, 2000.
Dobin et al., "STAR: ultrafast universal RNA-seq aligner," Bioinformatics, 29(1):15-21, Jan. 2013.
Doering et al., "Network analysis reveals centrally connected genes and pathways involved in CD8+ T cell exhaustion versus memory," Immunity, 37(6):1130-1144, Nov. 15, 2012.
Dong et al., "A novel method for identifying downstream signals in tumor-reactive T cells following PD-1 engagement and monitoring endogenous tumor immunity and immunotherapy," Journal of Clinical Oncology, 32(15):Abstract3049-3049, 2014.
Dong et al., "B7—H1 determines accumulation and deletion of intrahepatic CD8(+) T lymphocytes," Immunity., 20(3):327-336, Mar. 2004.
Dong et al., "B7—H1 pathway and its role in the evasion of tumor immunity" J Mol Med (Berl)., 81(5):281-287, Apr. 30, 2003.
Dong et al., "B7—H1, a third member of the B7 family, co-stimulates T-cell proliferation and interleukin-10 secretion," Nat Med., 5(12):1365-1369, Dec. 1999.
Dong et al., "Immune regulation by novel costimulatory molecules," Immunol Res., 28(1):39-48, 2003.
Dong et al., "Immunoregulatory role of B7—H1 in chronicity of inflammatory responses," Cell Mol Immunol., 3(3):179-187, Jun. 2006.
Dong et al., "Tumor-associated B7—H1 promotes T-cell apoptosis: A potential mechanism of immune evasion," Nat. Med., 8(8):793-800, Jun. 2002.
Dragoi et al., "DNA-PKcs, but not TLR9, is required for activation of Akt by CpG-DNA," EMBO J., 24(4):779-789, Jan. 27, 2005.
Dronca et al., "BCL-2-interacting mediator of cell death (Bim) is a novel biomarker for response to anti-PD-1 therapy in patients with advanced melanoma," Immunotherapy., 8(12)1351-1353, Dec. 1, 2016.
Dronca et al., "Bim and soluble PD-L1 (sPD-L1) as predictive biomarkers of response to anti-PD-1 therapy in patients with melanoma and lung carcinoma," J Clin Oncol., 35(15suppl):11534, May 30, 2017.
Dronca et al., "Soluble PD-L1 (sPD-L1) is associated with decreased survival in metastatic melanoma," Abstract, Presented at Proceedings of Society for Melanoma Research 2015 Congress, San Francisco, CA, Nov. 18-21, 2015, 2 pages.
Dronca et al., "T cell Bim levels reflect responses to anti-PD-1 cancer therapy," JCI Insight., 1(6):e86014, May 5, 2016, 14 pages.
Dudler et al., "Gene transfer of programmed death Ligand-1.lg prolongs cardiac allograft survival," Transplantation, 82(12):1733-1737, Dec. 27, 2006.
Dunussi-Joannopoulos et al., "Gene therapy with B7.1 and GM-CSF vaccines in a murine AML model," J Pediatr Hematol Oncol., 19(6):536-540, Nov./Dec. 1997.
Durai et al., "Zinc finger nucleases: custom-designed molecular scissors for genome engineering of plant and mammalian cells," Nucleic Acids Research, Oct. 26, 2005, 33(18):5978-5990.
Duraiswamy et al., "Phenotype, function, and gene expression profiles of programmed death-1(hi) CD8 T cells in healthy human adults," J Immunol., 186(7):4200-4212, Apr. 1, 2011.
Duraiswamy et al., "Replenish the source within Rescuing tumor-infiltrating lymphocytes by double checkpoint blockade," Oncol., 2(10):e25912, Oct. 2013, 3 pages.
Ehl et al., "Different susceptibility of cytotoxic T cells to CD95 (Fas/Apo-1) ligand-mediated cell death after activation in vitro versus in vivo," J Immunol., 156(7):2357-2360, Apr. 1, 1996.
Elliott et al., "Mitoxantrone in combination with an inhibitor of DNA-dependent protein kinase: a potential therapy for high risk B-cell chronic lymphocytic leukaemia," Br J Haematol., 152(1):61-71, Nov. 18, 2010.
EMBL-EBI Accession No. AF 142780.2 "Mus musculus butyrophilin-like protein (Btdc) mRNA, complete cds," created Jun. 1, 1999, 2 pages.
EMBL-EBI Accession No. Q9WUL5, "Programmed cell death 1 ligand 2," Nov. 1, 1999, 5 pages.
Engh et al., "Accurate bond and angle parameters for X-ray protein structure refinement," Acta Cryst., A47(4):392-400, Jul. 1, 1991.
Ennis et al., "Effect of Novel Limited Spectrum MMP Inhibitor XL784 in Abdominal Aortic Aneurysms," J. Cardiovasc. Pharmacol. Ther., 17(4):417-426, Dec. 2012.
Escudier et al., "Treatment Beyond Progression in Patients with Advanced Renal Cell Carcinoma Treated with Nivolumab in CheckMate 025," Eur Urol., 72(3):368-376, Apr. 12, 2017.
Falkner et al., "pUV I: a new vaccinia virus insertion and expression vector," Nucleic Acids Res., 15(17):7192, Sep. 11, 1987.
Fan et al., "HNS, a nuclear-cytoplasmic shuttling sequence in HuR," Proc. Natl. Acad. Sci. USA, 95(26):15293-15298, Dec. 1998.
Farley et al., "p38 mitogen-activated protein kinase mediates the Fas-induced mitochondrial death pathway in CD8+ T cells," Mol Cell Biol., 26(6):2118-2129, Mar. 2006.
Favre et al., "DOK4 and DOK5: new dok-related genes expressed in human T cells," Genes Immunity, Jan. 16, 2003, 4(1):40-45.
Fechteler et al., "Prediction of protein three-dimensional structures in insertion and deletion regions: a procedure for searching data bases of representative protein fragments using geometric scoring criteria," J Mol Biol., 253(1):114-131, Oct. 13, 1995.
Feng et al., "Identification of a PKB/Akt hydrophobic motif Ser-473 kinase as DNA-dependent protein kinase," J Biol Chem., 279(39):41189-41196, Jul. 15, 2004.
Ferrari et al., "Flow cytometric analysis of circulating dendritic cell subsets and intracellular cytokine production in advanced breast cancer patients," Oncol Rep., 14(1):113-120, Jul. 2005.
Figlin et al., "Treatment of metastatic renal cell carcinoma with nephrectomy, interleukin-2 and cytokine-primed or CD8(+) selected tumor infiltrating lymphocytes from primary tumor," J Urol., 158(3 Pt 1):740-745, Sep. 1997.
Finck et al., "Treatment of Murine Lupus with CTLA4Ig," Science, 265(5176):1225-1227, Aug. 26, 1994.
Fire et al., "Potent and specific genetic interference by double-stranded RNA in Caenorhabditis elegans," Nature, 391(6669):806-811, Feb. 19, 1998.
Flaherty et al., "Phase III trial of carboplatin and paclitaxel with or without sorafenib in metastatic melanoma," J Clin Oncol., 31(3):373-379, Jan. 20, 2013.
Fleming et al., Selective expression of Ly-6G on myeloid lineage cells in mouse bone marrow. RB6-8C5 mAb to granulocyte-differentiation antigen (Gr-1) detects members of the Ly-6 family, J Immunol., 151(5):2399-2408, Sep. 1, 1993.

(56) References Cited

OTHER PUBLICATIONS

Foell et al., "CD137 costimulatory T cell receptor engagement reverses acute disease in lupus-prone NZB x NZW F1 mice," J Clin Invest., 111(10):1505-1518, May 2003.

Foell et al., "CD137-Mediated T Cell Co-Stimulation Terminates Existing Autoimmune Disease in SLE-Prone NZB/NZW F1 Mice," Ann N Y Acad Sci., 987:230-235, Apr. 2003.

Fortugno et al., "Survivin exists in immunochemically distinct subcellular pools and is involved in spindle microtubule function," J Cell Sci., 115(Pt 3):575-585, Feb. 1, 2002.

Fraietta et al., "Author Correction: Determinants of response and resistance to CD19 chimeric antigen receptor (CAR) T cell therapy of chronic lymphocytic leukemia," Nat. Medicine, 27(3):561, Feb. 5, 2021.

Fraietta et al., "Determinants of response and resistance to CD19 chimeric antigen receptor (CAR) T cell therapy of chronic lymphocytic leukemia," Nat. Medicine, 24(5):563-571, Apr. 30, 2018.

Fraietta et al., "Disruption of TET2 promotes the therapeutic efficacy of CD19-targeted T cells," Nature, 558(7709):307-312, May 30, 2018.

Franciszkiewicz et al., "Role of chemokines and chemokine receptors in shaping the effector phase of the anti tumor immune response," Cancer Res., 72(24):6325-6332, Dec. 15, 2012.

Frank et al., "An outcome prediction model for patients with clear cell renal cell carcinoma treated with radical nephrectomy based on tumor stage, size, grade and necrosis: the SSIGN score," J Urol., 168(6):2395-2400, Dec. 2002.

Freeman et al., "B7, a new member of the Ig superfamily with unique expression on activated and neoplastic B cells," J Immunol., 143(8):2714-2722, Oct. 15, 1989.

Freeman et al., "Cloning of B7-2: a CTLA-4 counter-receptor that co stimulates human T cell proliferation," Science, 262(5135):909-911, Nov. 5, 1993.

Freeman et al., "Engagement of the PD-1 ImmunoInhibitory receptor by a novel B7 family member leads to negative regulation of lymphocyte activation," J Exp Med., 192(7):1027-1034, Oct. 2, 2000.

Freeman et al., "Structure, expression, and T cell proliferation costimulatory activity of the murine homologue of the human B lymphocyte activation antigen B7," J Exp Med., 174(3):625-631, Sep. 1, 1991.

Friedlander et al., "miRDeep2 accurately identifies known and hundreds of novel microRNA genes in seven animal clades," Nucleic Acids Research, 40(1):37-52, Jan. 1, 2012.

Friedman et al., "Clinical Benefit of INCB7839, a Potent and Selective Inhibitor of ADAM10 and ADAM17, in Combination with Trastuzumab in Metastatic HER2 Positive Breast Cancer Patients," Cancer Res., 69(24 Suppl):Abstract5056, Dec. 2009.

Friedmann et al., "Interaction of the epidermal growth factor receptor and the DNA-dependent protein kinase pathway following gefitinib treatment," Mol Cancer Ther., 5(2):209-218, Feb. 2006.

Frigola et al., "Identification of a soluble form of B7—H1 that retains immunosuppressive activity and is associated with aggressive renal cell carcinoma," Clin Cancer Res., 17(7):1915-1923, Apr. 2011.

Frigola et al., "Soluble B7—H1: Differences in production between dendritic cells and T cells," Immunol Lett., 142(1-2):78-82, Feb. 29, 2012.

Fuerst et al., "Transfer of the inducible lac repressor/operator system from *Escherichia coli* to a vaccinia expression vector," Proc Natl Acad Sci USA., 86(8):2549-2553, Apr. 1989.

Fyfe et al., "Results of treatment of 255 patients with metastatic renal cell carcinoma who received high-dose recombinant interleukin-2 therapy," J Clin Oncol., 13(3):688-696, Mar. 1995.

Gai et al., "Extracellular vesicles in onco-nephrology," Exp. Mol. Medicine, 51:1-8, Mar. 15, 2019.

Gao et al., "CYSLTR1 promotes adenoid hypertrophy by activating ERK1/2," Exp. Ther. Medicine, Aug. 2018. 16(2):966-970.

Garon et al., "Pembrolizumab for the Treatment of Non-Small-Cell Lung Cancer," N Engl J Med., 372(21):2018-2028, May 21, 2015.

Gauthier et al., "Efficacy and Toxicity of CD19-Specific Chimeric Antigen Receptor T Cells Alone or in Combination with Ibrutinib for Relapsed and/or Refractory CLL," Biol. Blood Marrow Transplantation, 25(3S):S9-S10, Mar. 2019.

Geller et al., "Combination therapy with IL-15 superagonist (ALT-803) and PD-1 blockade enhances human NK cell immunotherapy against ovarian cancer," Gynecologic Oncology, 145(S1):19, Jun. 1, 2017.

GenBank Accession No. AAC51660 "apoptosis inhibitor survivin [*Homo sapiens*]," Sep. 2, 2004, 2 pages.

GenBank Accession No. AAP37283, "immune costimulatory protein B7—H4 [*Homo sapiens*], " Jun. 1, 2003, 1 page.

GenBank Accession No. AK001872.1,"*Homo sapiens*cDNA FLJ11010 fis, clone PLACE1003145," Feb. 22, 2000, 2 pages.

GenBank Accession No. AL162253, "Human DNA sequence from clone RP11-574F11 on chromosome 9 contains the gene for B7—H1 protein (PD-L1), the gene for programmed death ligand 2 (PDL2) (PDCD1L2) and a novel gene, complete sequence" Feb. 24, 2008, 35 pages.

GenBank Accession No. AY280972, "*Homo sapiens*immune costimulatory protein B7—H4 mRNA, complete cds," Jun. 1, 2003, 1 page.

GenBank Accession No. NM_005191.3 (GI No. 113722122), "*Homo sapiens*CD80 molecule (CD80), mRNA," Jun. 15, 2013, 5 pages.

GenBank Accession No. NP_000052.1, "tyrosine-protein kinase BTK isoform 1 [*Homo sapiens*]," dated Nov. 1, 2020, 4 pages.

GenBank Accession No. NP_005182.1 (GI No. 4885123), "T-lymphocyte activation antigen CD80 precursor [*Homo sapiens*]," Jun. 15, 2013, 3 pages.

GenBank Accession No. U75285 "*Homo sapiens*apoptosis inhibitor survivin gene, complete cds," Sep. 2, 2004, 5 pages.

GenBank® Accession No. AAF25807 (GI No. 6708119), "B7—H1 [*Homo sapiens*]," Jan. 18, 2000, 2 pages.

GenBank® Accession No. AAH74740.1, GI No. 49902307, "Programmed cell death 1 [*Homo sapiens*]," Jul. 15, 2006, 2 pages.

GenBank® Accession No. AAX29153.1, GI No. 60652917, "integrin alpha L, partial [synthetic construct]," Mar. 29, 2005, 2 pages.

GenBank® Accession No. AF177937 (GI No. 6708118), "*Homo sapiens*B7—H1 mRNA, complete cds," Jan. 18, 2000, 1 page.

GenBank® Accession No. BC008777.2, GI No. 33870544, "*Homo sapiens*integrin, alpha L (antigen CD11A (p180), lymphocyte function-associated antigen 1; alpha polypeptide), mRNA (cDNA clone MGC:1714 Image:3142951), complete cds," Jul. 28, 2005, 4 pages.

GenBank® Accession No. BC074740.2, GI No. 50960296, "*Homo sapiens*programmed cell death 1, mRNA (cDNA clone MGC:103817 Image:30915198), complete cds," Jul. 15, 2006, 3 pages.

GenPept Accession No. Q9NZQ7.1, RecName: Full-Programmed cell death 1 ligand 1; Short=PD-L1; Short=PDCD1 ligand 1; Short=Programmed death ligand 1; AltName: Full=B7 homolog 1; Short=B7—H1; AltName: CD antigen=CD274; Flags: Precursor, Nov. 30, 2016, 5 pages.

Gérard et al., "Dok-4 is a novel negative regulator of T cell activation," J. Immunology, Jun. 2009, 182(12):7681-7689.

Gerdes et al. "Cell cycle analysis of a cell proliferation-associated human nuclear antigen defined by the monoclonal antibody Ki-67," J Immunol., 133(4):1710-1715, Oct. 1984.

Gerlach et al., "The Chemokine Receptor CX3CR1 Defines Three Antigen-Experienced CD8 T Cell Subsets with Distinct Roles in Immune Surveillance and Homeostasis," Immunity, 45(6):1270-1284, Dec. 20, 2016.

Gerstmayer et al., "Costimulation of T cell proliferation by a chimeric B7-2 antibody fusion protein specifically targeted to cells expressing the erbB2 proto-oncogene," J Immunol., 158(10):4584-4590, May 15, 1997.

Gerstmayer et al., "Costimulation of T-cell proliferation by a chimeric B7 antibody fusion protein," Cancer Immunol Immunother., 45(3-4):156-158, Nov./Dec. 1997.

Gevaert et al., "Protein identification based on matrix assisted laser desorption/ionization-post source decay-mass spectrometry," Electrophoresis, 22(9):1645-1651, May 2001.

Ghebeh et al., "Doxorubicin downregulates cell surface B7—H1 expression and upregulates its nuclear expression in breast cancer cells: role of B7—H1 as an anti-apoptotic molecule," Breast Cancer Res., 12(4):R48, Jul. 13, 2010.

(56) References Cited

OTHER PUBLICATIONS

Ghebeh et al., "The B7—H1 (PD-L1) T lymphocyte-inhibitory molecule is expressed in breast cancer patients with infiltrating ductal carcinoma: correlation with important high risk prognostic factors," Neoplasia, 8(3):190-198, Mar. 2006.

Ghiringhelli et al., "Metronomic cyclophosphamide regimen selectively depletes CD4+CD25+ regulatory T cells and restores T and NK effector functions in end stage cancer patients," Cancer Immunol Immunother., 56(5):641-648, May 2007.

Gibbons et al., "B7—H1 limits the entry of effector CD8(+) T cells to the memory pool by upregulating Bim," Oncoimmunology, 1(7):1061-1073, Oct. 1, 2012.

Gibbons Johnson et al., "Functional Expression of Programmed Death-Ligand 1 (B7—H1) by Immune Cells and Tumor Cells," Front Immunol, 8:961, Aug. 10, 2017, 9 pages.

Gilbert et al., "RNA Immunoprecipitation for Determining RNA-Protein Associations In Vivo," Curr. Protoc. Mol. Biology, Chapter 27, Unit 27.4, Aug. 2006, 11 pages.

Gillings et al., "Apoptosis and autophagy: BIM as a mediator of tumour cell death in response to oncogene-targeted therapeutics," FEBS J., 276(21):6050-6062, Sep. 29, 2009.

Gimmi et al., "B-cell surface antigen B7 provides a costimulatory signal that induces T cells to proliferate and secrete interleukin 2," Proc Natl Acad Sci USA., 88(9):3671-3675, May 1, 1991.

Gomes et al., "Analytical Considerations in Nanoscale Flow Cytometry of Extracellular Vesicles to Achieve Data Linearity," Thromb. Haemost., 118(9):1612-1624, Sep. 2018.

Gomes-Silva et al., "Tonic 4-1BB Costimulation in Chimeric Antigen Receptors Impedes T Cell Survival and Is Vector-Dependent," Cell Reports, 21(1):17-26, Oct. 3, 2017.

Goodwin et al., "Molecular cloning and expression of the type 1 and type 2 murine receptors for tumor necrosis factor," Mol Cell Biol., 11(6):3020-3026, Jun. 1991.

Goodwin et al., "Molecular cloning of a ligand for the inducible T cell gene 4-1BB: a member of an emerging family of cytokines with homology to tumor necrosis factor," Eur J Immunol., 23(10):2631-2641, Oct. 1993.

Gottesman et al., "Multidrug resistance in cancer; role of ATP-dependent transporters," Nat Rev Cancer, 2(1):48-58, Jan. 2002.

Grayson et al., "Cutting edge: increased expression of Bcl-2 in antigen-specific memory CD8+ T cells," J Immunol., 164(8):3950-3954, Apr. 15, 2000.

Green et al., "Activation-induced cell death in T cells," Immunol Rev., 193:70-81, Jun. 2003.

Green et al., "Antigen-specific human monoclonal antibodies from mice engineered with human Ig heavy and light chain YACs," Nat Genet., 7(1):13-21, May 1994.

Greenwald et al., "The B7 family revisited," Annu Rev Immunol., 23:515-548, 2005.

Griffiths-Jones et al., "miRBase: microRNA sequences, targets and gene nomenclature," Nucleic Acids Research, 34(suppl_1):D140-D144, Jan. 1, 2006.

Griffiths-Jones et al., "miRBase: tools for microRNA genomics," Nucleic Acids Research, 36(suppl_1):D154-D158, Jan. 1, 2008.

Griffiths-Jones, "The microRNA Registry," Nucleic Acids Research, 32(suppl_1):D109-D111, Jan. 1, 2004.

Grivennikov et al. "Immunity, inflammation, and cancer," Cell., 140(6):883-899, Mar. 19, 2010.

Gros et al., "PD-1 identifies the patient-specific CD8(+) tumor-reactive repertoire infiltrating human tumors," J Clin Invest., 124(5):2246-2259, May 2014.

Gros et al., "Prospective identification of neoantigen-specific lymphocytes in the peripheral blood of melanoma patients," Nat Med., 22(4):433-438, Apr. 2016.

Grupp et al., "Chimeric antigen receptor-modified T cells for acute lymphoid leukemia," N. Engl. J. Medicine, 368(16):1509-1518, Apr. 18, 2013.

Gu et al., "R gene expression induced by a type-III effector triggers disease resistance in rice," Nature, 435(7045):1122-1125, Jun. 23, 2005.

Guatelli et al., "Isothermal, in vitro amplification of nucleic acids by a multi enzyme reaction modeled after retroviral replication," Proc Natl Acad Sci USA., 87(5):1874-1878, Mar. 1990.

Guinn et al., "4-1BBL cooperates with B7-1 and B7-2 in converting a B cell lymphoma cell line into a long-lasting antitumor vaccine," J Immunol., 162(8):5003-5010, Apr. 15, 1999.

Gunn et al., "Correct end use during end joining of multiple chromosomal double strand breaks is influenced by repair protein RAD50, DNA-dependent protein kinase DNA-PKcs, and transcription context," J Biol Chem., 286(49):42470-42482, Oct. 24, 2011.

Guo et al., "A novel fusion protein of IP1 O-seFv retains antibody specificity and chemokine function," Biochem Biophys Res Commun., 320(2):506-513, Jul. 23, 2004.

Guo et al., "Directed evolution of an enhanced and highly efficient FokI cleavage domain for zinc finger nucleases," J Mol. Biology, Jul. 2, 2010, 400(1):96-107.

Haendeler et al., "Nitric Oxide and Apoptosis," Vitam Horm., 57:49-77, 1999.

Hamanishi et al., "PD-1/PD-L1 blockade in cancer treatment: perspectives and issues," Int. J. Clin. Oncology, 21(3):462-473, Jun. 2016.

Hamid et al., "Safety and Tumor Responses with Lambrolizumab (Anti-PD-1) in Melanoma," N Engl J Med., 369(2):134-144, Jul. 11, 2013.

Hansen et al., "Monoclonal antibodies identifying a novel T-cell antigen and Ia antigens of human lymphocytes," Immunogenetics, 10(1-4):247-260, Feb. 1, 1980.

Hardenberg et al., "A Yin and Yang in Epithelial Immunology: The Roles of the αE(CD103)β7 Integrin in T Cells," J. Invest. Dermatology, Jan. 2018, 138(1):23-31.

Harlow and Lane., "Antibodies: A Laboratory Manual," Cold Spring Harbor Laboratory Press, Cold Spring Harbor, NY, pp. 553, 555-582, 584-589, 591-612, 1988.

Harrington et al., "Differentiating between memory and effector CD8 T cells by altered expression of cell surface O-glycans," J Exp Med., 191(7):1241-1246, Apr. 3, 2000.

Hatzoglou et al., "Hepatic gene transfer in animals using retroviruses containing the promoter from the gene for phosphoenolpyruvate carboxykinase" J Biol Chem., 265(28):17285-17293, Oct. 5, 1990.

Haugland et al. "Unit 16.5 antibody conjugates for cell biology," Current Protocols in Cell Biology, 6:16.5:16.5-16.5.22, May 1, 2001.

Hawiger et al., "Dendritic cells induce peripheral T cell unresponsiveness under steady state conditions in vivo," J Exp Med., 194(6):769-779, Sep. 17, 2001.

Hayakawa et al., "Inhibition of BAD phosphorylation either at serine 112 via extracellular signal-regulated protein kinase cascade or at serine 136 via Akt cascade sensitizes human ovarian cancer cells to cisplatin," Cancer Res., 60(21):5988-5994, Nov. 1, 2000.

He et al., "Development of PD-1/PD-L1 Pathway in Tumor Immune Microenvironment and Treatment for Non-Small Cell Lung Cancer," Sci. Reports, 5:13110, Aug. 17, 2015, 9 pages.

He et al., "Identification of a novel splice variant of human PD-L1 mRNA encoding an isoform-lacking Igv-like domain," Acta. Pharmacol. Sin., 26(4):462-468, Apr. 2005.

Heinz et al., "Simple Combinations of Lineage-Determining Transcription Factors Prime cis-Regulatory Elements Required for Macrophage and B Cell Identities," Mol. Cell, 38(4):576-589, May 28, 2010.

Hellstrom et al., "T cell immunity to tumor antigens," Crit Rev Immunol., 18(1-2):Jan. 6, 1998.

Henry et al., "Cloning, structural analysis, and mapping of the B30 and B7 multigenic families to the major histocompatibility complex (MHC) and other chromosomal regions," Immunogenetics, 46(5):383-395, 1997.

Henry et al., "Structure and evolution of the extended B7 family," Immunol Today, 20(6):285-288, Jun. 1999.

Hentikoff, "Amino acid substitution matrices from protein blocks," Proc Natl Acad Sci USA., 89(22):10915-10919, Nov. 15, 1992.

Her et al., "Increased expression of soluble inducible costimulator ligand (ICOSL) in patients with systemic lupus erythematosus," Lupus, 18(6):501-507, May 2009.

(56) References Cited

OTHER PUBLICATIONS

Herold et al., "Impact of conditional deletion of the pro-apoptotic BCL-2 family member BIM in mice," Cell Death Dis., 5(10):e1446, Oct. 9, 2014, 7 pages.
Hestdal et al., "Characterization and regulation of RB6-8C5 antigen expression on murine bone marrow cells," J Immunol., 147(1):22-28, Jul. 1, 1991.
Hidalgo et al., "The transcriptome of human cytotoxic T cells: similarities and disparities among allostimulated CD4( +) CTL, CD8( +) CTL and NK cells," Am J Transplant., 8(3):627-636, Mar. 2008.
Hildeman et al., "Activated T cell death in vivo mediated by proapoptotic bcl-2 family member bim," Immunity, 16(6):759-767, Jun. 2002.
Hirano et al., "Blockade of B7—H1 and PD-1 by monoclonal antibodies potentiates cancer therapeutic immunity," Cancer Res., 65(3):1089-1096, Feb. 1, 2005.
Hiroishi et al., "Interferon-alpha gene therapy in combination with CDS0 transduction reduces tumorigenicity and growth of established tumor in poorly immunogenic tumor models," Gene Ther., 6(12):1988-1994, Dec. 1999.
Hochman et al., "An active antibody fragment (Fv) composed of the variable portions of heavy and light chains," Biochemistry, 12(6):1130-1135, Mar. 13, 1973.
Hock et al., "Retrovirus-mediated transfer and expression of drug resistance genes in human haematopoietic progenitor cells," Nature, 320:275-277, 1986.
Hodi et al., "Evaluation of Immune-Related Response Criteria and RECIST v1.1 in Patients With Advanced Melanoma Treated With Pembrolizumab," J Clin Oncol., 34(13):1510-1517, May 1, 2016.
Hoeijmakers, "Genome maintenance mechanisms for preventing cancer," Nature, 411(6835):366-374, May 17, 2011.
Hoffman, "T Cells in the Pathogenesis of Systemic Lupus Erythematosus," Front Biosci., 6:D1369-D1378, Oct. 1, 2001.
Hoiseth et al., "Aromatic-dependent *Salmonella typhimurium* are non-virulent and effective as live vaccines," Nature, 291(5812):238-239, May 21, 1981.
Hollinger et al., "Diabodies": small bivalent and bispecific antibody fragments, Proc Natl Acad Sci USA., 90(14):6444-6448, Jul. 15, 1993.
Holt et al., "Domain antibodies: proteins for therapy," Trends Biotechnol., 21(11):484-490, Nov. 2003.
Hoos et al., "CCR 20th Anniversary Commentary: Immune-Related Response Criteria—Capturing Clinical Activity in Immuno-Oncology," Clin Cancer Res., 21(22):4989-4991, Nov. 2015.
Hori et al., "B7—H1-induced apoptosis as a mechanism of immune privilege of corneal allografts," J Immunol., 177(9):5928-5935, Nov. 1, 2006.
Hou et al., "Correlation between infiltration of FOXP3+ regulatory T cells and expression of B7—H1 in the tumor tissues of gastric cancer," Exp. Mot. Pathol., 96(3):284-291, Jun. 2014.
Houseley et al., "The many pathways of RNA degradation," Cell, 136(4):763-776, Feb. 20, 2009.
Hua et al., "B7—H1 expression is associated with expansion of regulatory T cells in colorectal carcinoma," World J. Gastroenterol., 18(9):971-978, Mar. 2012.
Huai et al., "Inducible gene expression with the Tet-on system in CD4+ T cells and thymocytes of mice," Genesis, 45(7):427-431, Jul. 2007.
Huang et al., "CDK2-Dependent Phosphorylation of FOXO1 as an Apoptotic Response to DNA Damage," Science, 314(5797):294-297, Oct. 13, 2006.
Huang et al., "Fragile Histidine Triad (FHIT) Suppresses Proliferation and Promotes Apoptosis in Cholangiocarcinoma Cells by Blocking PI3K-Akt Pathway," Scientific World Journal, Mar. 16, 2014, 2014:179698, 8 pages.
Huang et al., "T-cell invigoration to tumour burden ratio associated with anti-PD-1 response," Nature, 545(7652):60-65, Apr. 10, 2017.

Huang et al., "The liver eliminates T cells undergoing antigen-triggered apoptosis in vivo," Immunity, 1(9):741-749, Dec. 31, 1994.
Huang, "Structural chemistry and therapeutic intervention of protein-protein interactions in immune response, human immunodeficiency virus entry, and apoptosis," Pharmacol Ther., 86(3):201-215, Jun. 2000.
Hubbard et al., "Anti-neutrophil-elastase defenses of the lower respiratory tract in alpha 1-antitrypsin deficiency directly augmented with an aerosol of alpha I-antitrypsin," Ann Intern Med., 111(3):206-212, Aug. 1, 1989.
Hui et al., "T cell costimulatory receptor CD28 is a primary target for PD-1-mediated inhibition," Science, 355(6332):1428-1433, Mar. 9, 2017.
Hunter, "Diabetes in pregnancy," Effective Care in Pregnancy and Childbirth, Chalmers et al. (eds.), Oxford University Press, 1:578-593, 1989.
Huse et al., "Generation of a large combinatorial library of the immunoglobulin repertoire in phage lambda," Science, 246(4935):1275-1281, Dec. 8, 1989.
Huston et al., "Protein engineering of antibody binding sites: recovery of specific activity in an anti-digoxin single-chain Fv analogue produced in *Escherichia coli*," Proc Natl Acad Sci USA., 85(16):5879-5883, Aug. 1988.
Hutloff et al., "ICOS is an inducible T-cell co-stimulator structurally and functionally related to CD28," Nature, 397(6716):263-266, Jan. 21, 1999.
Hwang et al., "Efficient genome editing in zebrafish using a CRISPR-Cas system," Nat. Biotechnology, 31(3):227-229, Jan. 29, 2013.
Hyrup et al., "Peptide nucleic acids (PNA): synthesis, properties and potential applications," Bioorg Med Chem., 4(1):5-23, Jan. 31, 1996.
Ice et al., "AB0143: Immunomodulation followed by quantitative transcriptional profiling to characterize the functional role of the sjÖgren's-associated ncrna ac092580.4," Ann Rheum Dis., 76(S2):1096, Jun. 15, 2017.
Ichikawa and Chen, "Role of B7—H1 and B7—H4 molecules in down-regulating effector phase of T-cell immunity: novel cancer escaping mechanisms," Front Biosci., 10:2856-2860, Sep. 1, 2005.
Ikemizu et al., "Structure and dimerization of a soluble form of B7-1," Immunity, 12(1):51-60, Jan. 2000.
Ikonomidis, "Delivery of a viral antigen to the class I processing and presentation pathway by Listeria monocytogenes," J Exp Med., 180(6):2209-2218, Dec. 1, 1994.
Imai et al., "Identification and molecular characterization of fractalkine receptor CX3CR1, which mediates both leukocyte migration and adhesion," Cell, 91(4):521-530, Nov. 14, 1997.
Infante et al., "A multicenter phase Ib study of the safety, pharmacokinetics, biological activity and clinical efficacy of INCB7839, a potent and selective inhibitor of ADAM10 and ADAM17," Breast Cancer Res. Treat., 106(1):S269, 6064, Dec. 2007.
Inman et al. "PD-L1 (B7—H1) expression hy urothelial carcinoma of the bladder and BCG-induced granulomata: associations with localized stage progression," Cancer, 109(8):1499-1505, Apr. 15, 2007.
Inman et al., "Questionable relevance of gamma delta T lymphocytes in renal cell carcinoma," J Immunol., 180(5):3578-3584, Mar. 1, 2008.
Ishida et al., "Differential expression of PD-L1 and PD-L2, ligands for an inhibitory receptor PD-1, in the cells of lymphohematopoietic tissues," Immunol Lett., 84(1):57-62, Oct. 21, 2002.
Ishida et al., "Induced expression of PD-1, a novel member of the immunoglobulin gene superfamily, upon programmed cell death," EMBO J., 11(11):3887-3895, Nov. 1992.
Iwai et al., "Involvement of PD-L1 on tumor cells in the escape from host immune system and tumor immunotherapy by PD-L1 blockade," Proc Natl Acad Sci USA., 99(19):12293-12297, Sep. 6, 2002.
Iwai et al., "PD-1 inhibits antiviral immunity at the effector phase in the liver," J Exp Med., 198(1):39-50, Jul. 7, 2003.
Jacinto et al., "SIN1/MIPI maintains rictor-mTOR complex integrity and regulates Akt phosphorylation and substrate specificity," Cell, 127(1):125-137, Sep. 7, 2006.

(56) References Cited

OTHER PUBLICATIONS

Jacobs et al., "Regulatory T cells in melanoma: the final hurdle towards effective immunotherapy?," Lancet Oncol., 13(1):e32-42, Jan. 2012.
Jacobson et al., "Unique site of IgG2a and rheumatoid factor production in MRL/lpr mice," Immunol Rev., 156:103-110, Apr. 1997.
Jacquelot et al., "Predictors of responses to immune checkpoint blockade in advanced melanoma," Nat. Commun., 8(1):592, Sep. 19, 2017.
Jamaly et al., "Impact of preanalytical conditions on plasma concentration and size distribution of extracellular vesicles using Nanoparticle Tracking Analysis," Sci. Reports, 8:17216, Nov. 21, 2018, 11 pages.
Janeway et al. "Immunobiology: the Immune System in Health and Disease," Elsevier Science., 4:36, 1999.
Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosamine (H2-CMX-Ros) and MitoTracker Red 580 (MTR580)," J Immunol Methods., 306(1-2):68-79, Sep. 29, 2005.
Jeannin et al., "Soluble CD86 is a costimulatory molecule for human T lymphocytes," Immunity, 13(3):303-312, Sep. 2000.
Jemal et al., "Cancer Statistics, 2005," CA Cancer J Clin, 55(1):10-30, Jan./Feb. 2005.
Jerne, "Towards a network theory of the immune system," Ann Immunol (Paris)., 125C(1-2):373-389, Jan. 1974.
Jiang et al., "Genome-wide association study for biomarker identification of Rapamycin and Everolimus using a lymphoblastoid cell line system," Front Genet., 4:166, Aug. 30, 2013.
Jiang et al., "RNA-guided editing of bacterial genomes using CRISPR-Cas systems," Nat. Biotechnology, 31(3):233-239, Jan. 29, 2013.
Jinek et al., "A programmable dual-RNA-guided DNA endonuclease in adaptive bacterial immunity," Science, 337(6096):816-821, Jun. 28, 2012.
Johnsen et al., "What is the blood concentration of extracellular vesicles? Implications for the use of extracellular vesicles as blood-borne biomarkers of cancer," Biochim. Biophys. Acta. Rev. Cancer, 1871(1):109-116, Jan. 2019.
Johnson et al., "Combinatorial therapy with an IL-15 superagonist (ALT-803) and anti-PD-L1 mAb augment T cell mediated antitumor immunity in mice," J. Immunother. Cancer, 2(Suppl. 3):p. 234, Nov. 6, 2014.
Johnson et al., "Fulminant Myocarditis with Combination Immune Checkpoint Blockade," N. Engl. J. Med., 375(18):1749-1755, Nov. 2016.
Johnston et al., "Biolistic transformation of animal tissue," In Vitro Cell Dev Biol Anim., 27P:Nov. 14, 1991.
Jones et al., "Replacing the complementarity-determining regions in a human antibody with those from a mouse," Nature, 321(6069):522-525, May 29-Jun. 4, 1986.
June et al., "CAR T cell immunotherapy for human cancer," Science, 359(6382):1361-1365, Mar. 23, 2018.
June et al., "Chimeric Antigen Receptor Therapy," N. Engl. J. Medicine, 379(1):64-73, Jul. 5, 2018.
Juvet et al., "Phosphodiesterase 3b Inhibition Expands Stable Regulatory T Cells for Cell Therapy in Transplantation," J. Heart Lung Transplantation, Apr. 2015, 34(4):S147.
Kabat et al., "Sequences of Proteins of Immunological Interest, Fifth Edition," U.S. Department of Health and Human Services, NIH Publication No. 91-3242, Table of Contents, 20 pages, 1991.
Kaech et al., "Transcriptional control of effector and memory CD8+ T cell differentiation," Nat Rev Immunol., 12(11):749-761, Nov. 2012.
Kalafatovic et al., "Cell-Penetrating Peptides: Design Strategies beyond Primary Structure and Amphipathicity," Molecules, 22(11):1929, Nov. 8, 2017, 38 pages.
Kaleko et al., "Persistent gene expression after retroviral gene transfer into liver cells in vivo," Hum Gene Ther., 2(1):27-32, 1991.
Kaliyaperumal et al., "Antigen-specific therapy of murine lupus nephritis using nucleosomal peptides: tolerance spreading impairs pathogenic function of autoimmune T and B cells," J Immunol., 162(10):5775-5783, May 15, 1999.
Kalled et al., "Anti-CD40 ligand antibody treatment of SNF1 mice with established nephritis: preservation of kidney function," J Immunol., 160(5):2158-2165, Mar. 1, 1998.
Kalos et al., "T cells with chimeric antigen receptors have potent antitumor effects and can establish memory in patients with advanced leukemia," Sci. Transl. Medicine, 3(95):95ra73, Aug. 10, 2011, 11 pages.
Kamphorst et al., "Proliferation of PD-1+ CD8 T cells in peripheral blood after PD-1-targeted therapy in lung cancer patients," Proc Natl Acad Sci USA., 114(19):4993-4998, May 9, 2017.
Kamphorst et al., "Rescue of exhausted CD8 T cells by PD-1-targeted therapies is CD28-dependent," Science, 355(6332):1423-1427, Mar. 31, 2017.
Kanai et al., "Blockade of B7—H1 suppresses the development of chronic intestinal inflammation," J Immunol., 171(8):4156-4163, Oct. 15, 2003.
Kaneko et al., "Augmentation of Va14 NKT cell-mediated cytotoxicity by interleukin 4 in an autocrine mechanism resulting in the development of concanavalin A-induced hepatitis," J Exp Med., 191(1):105-114, Jan. 3, 2000.
Kang et al., "Current clinical trials testing the combination of immunotherapy with radiotherapy," J. Immunother. Cancer, 4:51, Sep. 20, 2016, 20 pages.
Karakhanova et al., "ERK/p38 MAP-kinases and PI3K are involved in the differential regulation of B7—H1 expression in DC subsets," Eur J Immunol., 40(1):254-266, Jan. 2010.
Kataoka et al., "Flow cytometric analysis of phosphorylated histone H2AX following exposure to ionizing radiation in human microvascular endothelial cells," J Radiat Res., 47(3-4):245-257, Sep. 2006.
Katou et al., "Differing phenotypes between intraepithelial and stromal lymphocytes in early-stage tongue cancer," Cancer Res., 67(23):11195-11201, Dec. 1, 2007.
Kaufman et al., "A phase I trial of intra lesional RV-B7.1 vaccine in the treatment of malignant melanoma," Hum Gene Ther., 11(7):1065-1082, May 1, 2000.
Kawabe et al., "Programmed cell death and extrathymic reduction of VB8+ CD4+ T cells in mice tolerant to Staphylococcus aureus enterotoxin B," Nature, 349(6306):245-248, Jan. 17, 1991.
Kawalekar et al., "Distinct Signaling of Coreceptors Regulates Specific Metabolism Pathways and Impacts Memory Development in CAR T Cells," Immunity, 44(2):380-390, Feb. 16, 2016.
Kay et al., "A bacterial effector acts as a plant transcription factor and induces a cell size regulator," Science, 318(5850):648-651, Oct. 26, 2007.
Kee et al., "Antitumor immune activity by chemokine CX3CL1 in an orthotopic implantation of lung cancer model in vivo," Mol Clin Oncol., 1(1):35-40, Jan. 2013.
Keir et al., "PD-1 and its ligands in tolerance and immunity," Annu Rev Immunol., 26:677-704, 2008.
Kelley et al., "Cytokines in the Pathogenesis of Systemic Lupus Erythematosus," Semin Nephrol., 19(1):57-66, Jan. 1999.
Kenderian et al., "Chimeric antigen receptor T-cell therapy to target hematologic malignancies," Cancer Research, 74(22):6383-6389, Nov. 4, 2014.
Kenderian et al., "Identification of PD1 and TIM3 As Checkpoints That Limit Chimeric Antigen Receptor T Cell Efficacy in Leukemia," Blood, Dec. 3, 2015, 126(23):852.
Kenderian et al., "Leukemia Stem Cells Are Characterized By CLEC12A Expression and Chemotherapy Refractoriness That Can be Overcome By Targeting with Chimeric Antigen Receptor T Cells," Blood, Dec. 2, 2016, 128(22):766.
Kenderian et al., "Ruxolitinib Prevents Cytokine Release Syndrome after CART Cell Therapy without Impairing the Anti-Tumor Effect in a Xenograft Model," Blood, Dec. 2, 2016, 128(22):652.
Kennerdell et al., "Use of dsRNA-mediated genetic interference to demonstrate that frizzled and frizzled 2 act in the wingless pathway," Cell, 95(7):1017-1026, Dec. 23, 1998.

(56) References Cited

OTHER PUBLICATIONS

Kharbanda et al., "Translocation of SAPK/JNK to mitochondria and interaction with Bcl-x(L) in response to DNA damage," J Biol Chem., 275(1):322-327, Jan. 7, 2000.
Kiessling et al., "High-throughput mutation profiling of CTCL samples reveals KRAS and NRAS mutations sensitizing tumors toward inhibition of the RAS/RAF/MEK signaling cascade," Blood, 117(8):2433-2440, Jan. 5, 2011.
Kim et al., "Fas ligand-positive membranous vesicles isolated from sera of patients with oral cancer induce apoptosis of activated T lymphocytes," Clin. Cancer Research, 11(3):1010-1020, Feb. 1, 2005.
Kim et al., "Features of responding T cells in cancer and chronic infection," Curr Opin Immunol., 22(2):223-230, Mar. 6, 2010.
Kim et al., "Hybrid restriction enzymes: zinc finger fusions to Fok I cleavage domain," Proc. Natl. Acad Sci. USA, 93(3):1156-1160, Feb. 6, 1996.
Kim et al., "Therapeutic potential of 4-1BB (CD137) as a regulator for effector CD8(+) T cells," J Hematother Stem Cell Res., 10(4):441-449, Aug. 2001.
Kim et al., "TNFR2-deficient memory CD8 T cells provide superior protection against tumor cell growth," J. Immunology, Nov. 15, 2009, 183(10):6051-6057.
Kim et al., "TopHat2: accurate alignment of transcriptomes in the presence of insertions, deletions and gene fusions," Genome Biology, 14:R36, Apr. 25, 2013, 13 pages.
Klimka et al., "Human anti-CD30 recombinant antibodies by guided phage antibody selection using cell panning," Brit. J. Can., 83(2):252-260, Jul. 2000.
Köhler et al., "Continuous cultures of fused cells secreting antibody of predefined specificity," Nature, 256(5517):495-497, Aug. 7, 1975.
Kohn et al. "Gene therapy for genetic diseases," Cancer Invest., 7(2):179-192, 1989.
Konem et al., "IL-12 secreting tumor-targeted chimeric antigen receptor T cells eradicate ovarian tumors in vivo," Oncoimmunology, Jan. 23, 2015, 4(3):e994446, 11 pages.
Konieczny et al., "The combination of IgM subunits and proteolytic IgG fragment by controlled formation of interchain disulphides," Haematologia (Budap)., 14(1):95-99, 1981.
Korkola et al, "Gene expression-based classification of nonseminomatous male germ cell tumors," Oncogene, 24(32):5101-5107, Jul. 28, 2005.
Kosari et al, "Clear cell renal cell carcinoma: gene expression analyses identify a potential signature for tumor aggressiveness," Clin Cancer Res., 11(14):5128-5139, Jul. 15, 2005.
Kozbor et al. "The production of monoclonal antibodies from human lymphocytes," Immunology Today, 4(3):72-79, Mar. 1, 1983.
Kozomara et al., "miRBase; annotating high confidence microRNAs using deep sequencing data," Nucleic Acids Research, 42(D1):D68-D73, Jan. 1, 2014.
Kozomara et al., "miRBase: from microRNA sequences to function," Nucleic Acids Research, 47(D1):D155-D162, Jan. 8, 2019.
Kozomara et al., "miRBase: integrating microRNA annotation and deepsequencing data," Nucleic Acids Research, 39(suppl_1):D152-D157, Jan. 1, 2011.
Krämer et al., "Causal analysis approaches in Ingenuity Pathway Analysis," Bioinformatics, 30(4):523-530, Feb. 15, 2014.
Krempski et al., "Tumor-infiltrating programmed death receptor-1+ dendritic cells mediate immune suppression in ovarian cancer," J Immunol., 186(12):6905-6913, May 6, 2011.
Krieg et al., "High-dimensional single-cell analysis predicts response to anti-PD-1 immunotherapy," Nat Med., 24:144-153, Jan. 8, 2018.
Kruege et al., "The role of CD95 in the regulation of peripheral T-cell apoptosis," Immunol Rev., 193:58-69, Jun. 2003.
Krummel et al., "CTLA-4 engagement inhibits IL-2 accumulation and cell cycle progression upon activation of resting T cells," J Exp Med., 183(6):2533-2540, Jun. 1, 1996.

Kuiper et al., "B7.1 and Cytokines: Synergy in cancer gene therapy," Adv Exp Med Biol., 465:381-390, 2000.
Kulakovskiy et al., "HOCOMOCO: a comprehensive collection of human transcription factor binding sites models," Nucl. Acids Research, 41(Database issue):D195-D202, Jan. 2013.
Kurtulus et al., "Bcl-2 allows effector and memory CD8+ T cells to tolerate higher expression of Bim," J Immunol., 186(10):5729-5737, May 15, 2011.
Kusmartsev et al., "Gr-1+ myeloid cells derived from tumor-bearing mice inhibit primary T cell activation induced through CD3/CD28 costimulation," J Immunol., 165(2):779-785, Jul. 15, 2000.
Kwon et al., "4-1BB: Still in the Midst of Darkness," Mol Cells., 10(2):119-126, Apr. 30, 2000.
LaBaer, "So, you want to look for biomarkers (introduction to the special biomarkers issue)," J Proteome Res., 4(4):1053-1059, Jul./Aug. 2005.
Langer et al., "Carboplatin and pemetrexed with or without pembrolizumab for advanced, non-squamous non-small-cell lung cancer: a randomised, phase 2 cohort of the open-label KEYNOTE-021 study," Lancet Oncol., 17(11):1497-1508, Nov. 2016.
Larkin et al., "Combined Nivolumab and Ipilimumab or Monotherapy in Untreated Melanoma," N Engl J Med., 373(1):23-34, Jul. 2, 2015.
Larrubia et al., "Bim-mediated apoptosis and PD-1/PD-L1 pathway impair reactivity of PD1(+)/CD127(−) HCV-specific CD8(+) cells targeting the virus in chronic hepatitis C virus infection," Cell Immunol., 269(2):104-114, Mar. 17, 2011.
Latchman et al., "PD-L2 is a second ligand for PD-1 and inhibits T cell activation," Nat Immunol., 2(3):261-268, Mar. 2001.
Lau et al., "Exacerbation of myasthenia gravis in a patient with melanoma treated with pembrolizumab," Muscle Nerve, 54(1):157-161, Jun. 2016.
Lawson et al., "Treatment of murine lupus with cDNA encoding IFN-gammaR/Fc," J Clin Invest., 106(2):207-215, Jul. 2000.
Lazarevic and Glimcher, "T-bet in disease," Nat Immunol., 12(7):597-606, Jun. 20, 2011.
Lee et al., "Survivin expression and its clinical significance in pancreatic cancer," BMC Cancer, 5:127, Oct. 4, 2005.
Lee et al., "Increased vaccine-specific T cell frequency after peptide-based vaccination correlates with increased susceptibility to in vitro stimulation but does not lead to tumor regression," J Immunol., 163(11):6292-6300, Dec. 1, 1999.
Leggett et al., "Sequencing quality assessment tools to enable data-driven informatics for high throughput genomics," Front. Genetics, 4:288, Dec. 2013, 5 pages.
Leibovich et al., "Prediction of progression after radical nephrectomy for patients with clear cell renal cell carcinoma: a stratification tool for prospective clinical trials," Cancer, 97(7):1663-1671, Apr. 1, 2003.
Lenardo et al., "Mature T lymphocyte apoptosis—immune regulation in a dynamic and unpredictable antigenic environment," Annu Rev Immunol., 17:221-253, 1999.
Lenschow et al., "CD28/B7 system of T cell costimulation," Annu Rev Immunol., 14:233-258, 1996.
Levitt, "Accurate modeling of protein conformation by automatic segment matching," J Mol Biol., 226(2):507-533, Jul. 20, 1992.
Lewinski et al., "Retroviral DNA integration: viral and cellular determinants of target-site selection," PLoS Pathog., 2(6):e60, Jun. 23, 2006.
Lewis et al., "Conserved seed pairing, often flanked by adenosines, indicates that thousands of human genes are microRNA targets," Cell, 120(1):15-20, Jan. 14, 2005.
Lewis et al., "Surrogate tumor antigen vaccination induces tumor-specific immunity and the rejection of spontaneous metastases," Cancer Res., 65(7):2938-2946, Apr. 1, 2005.
Lewis, "PCR's Competitors Are Alive and Well and Moving Rapidly Towards Commercialization," Genetic Engineering News, vol. 12, 3 pages, 1992.
Ley et al., "Regulatory phosphorylation of Bim: sorting out the ERK from the JNK," Cell Death Differ., 12(8):1008-1014, Aug. 2005.
Li et al., "Anti-programmed death-1 synergizes with granulocyte macrophage colony-stimulating factor—secreting tumor cell immunotherapy providing therapeutic benefit to mice with established tumors," Clin Cancer Res., 15(5):1623-1634, Feb. 10, 2009.

(56) References Cited

OTHER PUBLICATIONS

Li et al., "Gemcitabine and arabinosylcytosin pharmacogenomics: genome-wide association and drug response biomarkers," PLoS One., 4(11):e7765, Nov. 9, 2009.
Li et al., "The emerging roles and therapeutic potential of exosomes in epithelial ovarian cancer," Mol. Cancer, 16:92, May 15, 2017, 10 pages.
Liang et al., "Autoantibody responses and pathology regulated by B7-1 and B7-2 costimulation in MRL/lpr lupus," J Immunol., 165(6):3436-3443, Sep. 15, 2000.
Liao et al., "featureCounts; an efficient general purpose program for assigning sequence reads to genomic features," Bioinformatics, 30(7):923-930, Apr. 2014.
Lim et al., "The Principles of Engineering Immune Cells to Treat Cancer," Cell, 168, 168(4):724-740, Feb. 9, 2017.
Lin et al., "The PD-1/PD-L1 complex resembles the antigen-binding Fv domains of antibodies and T cell receptors," Proc Natl Acad Sci USA., 105(8):3011-3016, Feb. 26, 2008.
Linsley et al., "Binding of the B cell activation antigen B7 to CD28 costimulates T cell proliferation and interleukin 2 mRNA accumulation" J Exp Med., 173(3):721-730, Mar. 1, 1991.
Linsley et al., "Extending the B7 (CD80) gene family," Protein Sci., 3(8):1341-1343, Aug. 1994.
Linsley et al., "T-cell antigen CD28 mediates adhesion with B cells by interacting with activation antigen 87188-1," Proc Natl Acad Sci USA., 87(13):5031-5035, Jul. 1990.
Liu et al., "B7DC/PDL2 promotes tumor immunity by a PD-1-independent mechanism," J Exp Med., 197(12):1721-1730, Jun. 16, 2003.
Liu et al., "B7—H3 silencing increases paclitaxel sensitivity by abrogating Jak2/Stat3 phosphorylation," Mol Cancer Ther., 10(6):960-971, Apr. 25, 2011.
Liu et al., "CRISPR-Cas9-mediated multiplex gene editing in CAR-T cells," Cell Research, Jan. 2017, 27(1):154-157.
Liu et al., CTL- vs Treg lymphocyte-attracting chemokines, CCL4 and CCL20, are strong reciprocal predictive markers for survival of patients with oesophageal squamous cell carcinoma. Br J Cancer, 113(5):747-755, Sep. 1, 2015.
Liu et al., "Endogenous tumor-reactive CD8+ T cells are differentiated effector cells expressing high levels of CD11a and PD-1 but are unable to control tumor growth," Oncoimmunology., 2(6):e23972, Jun. 6, 2013.
Liu et al., "Fas-mediated apoptosis causes elimination of virus-specific cytotoxic T cells in the virus-infected liver," J Immunol., 166(5):3035-3041, Mar. 1, 2001.
Liu et al., "Interferon gamma plays a critical role in induced cell death of effector T cell: a possible third mechanism of self-tolerance," J Exp Med., 172(6):1735-1739, Dec. 1, 1990.
Liu et al., "Plasma cells from multiple myeloma patients express B7—H1 (PD-L1) and increase expression after stimulation with IFN-{gamma} and TLR ligands via a MyD88- , TRAF6- , and MEK-dependent pathway," Blood, 110(1):296-304, Mar. 15, 2007.
Locke et al., "Long-term safety and activity of axicabtagene ciloleucel in refractory large B-cell lymphoma (ZUMA-1): a single-arm, multicentre, phase 1-2 trial," Lancet Oncology, 20(1):31-42, Jan. 2019.
Lonberg et al., "Antigen-specific human antibodies from mice comprising four distinct genetic modifications," Nature, 368(6474):856-859, Apr. 28, 1994.
Long et al., "4-1BB costimulation ameliorates T cell exhaustion induced by tonic signaling of chimeric antigen receptors," Nat. Medicine, 21(6):581-590, May 4, 2015.
Losman et al., "Baboon anti-idiotype antibodies mimic a carcinoembryonic antigen epitope," Int J Cancer., 46(2):310-314, Aug. 15, 1990.
Love et al., "Moderated estimation of fold change and dispersion for RNA-seq data with DESeq2," Genome Biology, 15:550, Dec. 5, 2014, 21 pages.
Lu et al., "EGF-IL-18 fusion protein as a potential anti-tumor reagent by induction of immune response and apoptosis in cancer cells," Cancer Lett., 260(1-2):187-197, 2008.
Luciano et al., "Phosphorylation of Bim-EL by Erk½ on serine 69 promotes its degradation via the proteasome pathway and regulates its proapoptotic function," Oncogene., 22(43):6785-6793, Oct. 2, 2003.
Ludwinski et al., "Critical roles of Bim in T cell activation and T cell-mediated autoimmune inflammation in mice," J Clin Invest., 119(6):1706-1713, Jun. 2009.
Luettig et al., "Naive and memory T lymphocytes migrate in comparable numbers through normal rat liver: activated T cells accumulate in the periportal field," J Immunol., 163(8):4300-4307, Oct. 15, 1999.
Luke et al., "Targeted agents and immunotherapies: optimizing outcomes in melanoma," Nat Rev Clin Oncol., 14(8):463-482, Aug. 2017.
Lunsford et al., "Targeting LFA-1 and cd154 suppresses the in vivo activation and development of cytolytic (cd4-Independent) CD8+ T cells," J Immunol., 175(12):7855-7866, Dec. 15, 2005.
Luo et al., "Bim inhibits autophagy by recruiting Beclin 1 to microtubules," Mol Cell, 47(3):359-370, Aug. 10, 2012.
Lynn et al., "c-Jun overexpression in CAR T cells induces exhaustion resistance," Nature, 576(7786):293-300, Dec. 4, 2019.
Ma et al., "The DNA-dependent protein kinase catalytic subunit phosphorylation sites in human Artemis," J Biol Chem., 280(40):33839-33846, Aug. 10, 2005.
Ma et al., "The Role of PD-1 Ligand in Immune Evasion by Breast Cancer," Dana-Farber Cancer Institute Annual Summary Report—May 1, 2002-Apr. 30, 2005, pp. 5-6, 9, 11, report date: May 2005.
Maacha et al., "Extracellular vesicles-mediated intercellular communication: roles in the tumor microenvironment and anti-cancer drug resistance," Mol. Cancer, 18(1):55, Mar. 30, 2019, 16 pages.
Machanick et al., "MEME-ChIP: motif analysis of large DNA datasets," Bioinformatics, 27(12):1696-1697, Jun. 15, 2011.
Mah et al., "gammaH2AX: a sensitive molecular marker of DNA damage and repair," Leukemia, 24(4):679-686, Feb. 4, 2010.
Mahotka et al., "Distinct in vivo expression patterns of survivin splice variants in renal cell carcinomas," Int J Cancer, 100(1):30-36, Jul. 1, 2002.
Majzner et al., "Clinical lessons learned from the first leg of the CAR T cell journey," Nat. Medicine, 25(9):1341-1355, Sep. 9, 2019.
Makarova et al., "Evolution and classification of the CRISPR-Cas systems," Nat. Rev. Microbiology, 9(6):467-477, May 9, 2011.
Mali et al., "RNA-guided human genome engineering via Cas9," Science, 339(6121):823-826, Feb. 15, 2013.
Mandell et al., "Zinc Finger Tools: custom DNA-binding domains for transcription factors and nucleases," Nucleic Acids Research, Jul. 1, 2006, 34(suppl_2):W516-W523.
Mann et al., "Construction of a retrovirus packaging mutant and its use to produce helper-free defective retrovirus" Cell, 33(1):153-159, May 1983.
Martin et al. "Combination gene therapy with CD86 and the MHC Class II transactivator in the control of lung tumor growth," J Immunol., 162(11):6663-6670, Jun. 1, 1999.
Martin, "Cutadapt removes adapter sequences from high-throughput sequencing reads," EMBnet. Journal, 17(1):10-12, Aug. 2, 2011.
Matejcek et al., "Pharmaco-EEG and Psychometric study of the effect of single doses of temazepam and nitrazepam," Neuropsychobiology, 9(1):52-65, 1983.
Mathiowitz et al., "Morphology of poly anhydride microsphere delivery systems," Scanning Microsc., 4(2):329-340, Jun. 1990.
Mathiowitz et al., "Polyanhydride microspheres as drug carriers. I. Hot-melt microencapsulation," J. Controlled Release, 5(1):13-22, Jun. 1, 1987.
Mathiowitz et al., "Polyanhydride microspheres. IV. Morphology and characterization of systems made by spray drying," J. Annl. Polymer Sci. 45(1): 125-134, May 5, 1992.
Mathiowitz, Novel microcapsules for delivery systems, Reactive Polymers, 6(2):275-283, Oct. 31, 1987.

(56) References Cited

OTHER PUBLICATIONS

Mathiowitz, "Polyanhydride microspheres as drug carriers, II. Microencapsulation by solvent removal," J. Appl. Polymer Sci., 35(3): 755-774, Feb. 20, 1988.
Matsumoto et al., "CIS, a cytokine inducible SH2 protein, is a target of the JAK-STAT5 pathway and modulates STAT5 activation," Blood, 89(9):3148-3154, May 1, 1997.
Maude et al., "Tisagenlecleucel in Children and Young Adults with B-Cell Lymphoblastic Leukemia," N. Engl. J. Medicine, 378(5):439-448, Feb. 1, 2018.
Mayo Clinic, "Mayo Clinic Discovers Potential Marker For Aggressive Kidney Cancer," Science Daily, Retrieved from the Internet: <URL: https://www.sciencedaily.com/releases/2004/11/041130200858.htm>, Dec. 9, 2004, 2 pages.
Mayo.edu [online] "Center for Clinical and Translational Science (CCaTS): Study Design," Available on or before Oct. 12, 2012, via Internet Archive: Wayback Machine URL<https://web.archive.org/web/20121012161818/http://www.mayo.edu/ctsa/education/professional-development/online-courses/study-design>, retrieved on Mar. 23, 2021, retrieved from URL<https://web.archive.org/web/20170816080726/http://www.mayo.edu/ctsa/education/professional-development/online-courses/study-design>, 2 pages.
McCubrey et al., "Roles of the Raf/MEK/ERK pathway in cell growth, malignant transformation and drug resistance," Biochim Biophys Acta., 1773(8):1263-1284, Oct. 7, 2006.
McDermott et al., "PD-1 as a potential target in cancer therapy," Cancer Med., 2(5):662-673. Jul. 21, 2013.
McLachlin et al., "Retroviral-mediated gene transfer," Prog Nucleic Acid Res Mol Biol., 38:91-135, 1990.
Mehal et al., "Antigen presentation by liver cells controls intrahepatic T cell trapping, whereas bone marrow-derived cells preferentially promote intrahepatic T cell apoptosis," J Immunol., 167(2):667-673, Jul. 15, 2001.
Mehal et al., "TCR ligation on CD8+ T cells creates double-negative cells in vivo," J Immunol., 161(4):1686-1693, Aug. 15, 1998.
Melero et al., "Amplification of tumor immunity by gene transfer of the co-stimulatory 4-1BB ligand: synergy with the CD28 co-stimulatory pathway," Eur J Immunol., 28(3):1116-1121, Mar. 1998.
Melero et al., "Monoclonal antibodies against the 4-1BB T-cell activation molecule eradicate established tumors," Nat Med., 3(6):682-685, Jun. 1997.
Melero et al., "NK1.1 cells express 4-1BB (CDw137) costimulatory molecule and are required for tumor immunity elicited by anti-4-1BB monoclonal antibodies," Cell Immunol., 190(2):167-172, Dec. 15, 1998.
Melief et al., "Strategies for immunotherapy of cancer," Advances in Immunology, 75:235-282, Jan. 1, 2000.
Mellado et al., "A potential immune escape mechanism by melanoma cells through the activation of chemokine-induced T cell death," Curr Biol., 11(9):691-696, May 1, 2001.
Mendez-Fernandez et al., "Clearance of Theiler's virus infection depends on the ability to generate a CD8+ T cell response against a single immunodominant viral peptide," Eur J Immunol., 33(9):2501-2510, Sep. 2003.
Merrill, "Emergence of targeted immune therapies for systemic lupus," Expert Opin Emerg Drugs, 10(1):53-65, Feb. 2005.
Merritt et al., "Activation of p38 mitogen-activated protein kinase in vivo selectively induces apoptosis of CD8(+) but not CD4(+) T cells," Mol Cell Biol., 20(3):936-946, Feb. 2000.
Metzler et al., "Solution structure of human CTLA-4 and delineation of a CD80/CD86 binding site conserved in CD28," Nat Struct Biol., 4(7):527-531, Jul. 1997.
Meyts et al., "Deficiency of Adenosine Deaminase 2 (DADA2): Updates on the Phenotype, Genetics, Pathogenesis, and Treatment," J. Clin. Immunology, Jun. 27, 2018, 38(5):569-578.
Mezzadra et al., "Identification of CMTM6 and CMTM4 as PD-L1 Protein Regulators," Nature, 549(7670):106-110, Sep. 7, 2017.

Miller et al., "Gene transfer by retrovirus vectors occurs only in cells that are actively replicating at the time of infection," Mol Cell Biol., 10(8):4239-4242, Aug. 1990.
Miller et al., "Generation of helper-free amphotropic retroviruses that transduce a dominant-acting, methotrexate-resistant dihydrofolate reductase gene," Mol Cell Biol., 5(3):431-437, Mar. 1985.
Miller et al., "Molecular Pathways: Receptor Ectodomain Shedding in Treatment, Resistance, and Monitoring of Cancer," Clin. Cancer Research, 23(3):623-629, Feb. 1, 2017.
Miller et al., "Redesign of retrovirus packaging cell lines to avoid recombination leading to helper virus production," Mol Cell Biol., 6(8):2895-2902, Aug. 1986.
Miller, "Human gene therapy comes of age," Nature, 357(6378):455-460, Jun. 11, 1992.
Minderman et al., "DiOC2(3) is not a substrate for multidrug resistance protein (MRP)-mediated drug efflux," Cytometry, 25(1):14-20, Sep. 1, 1996.
Misquitta et al., "Targeted disruption of gene function in Drosophila by RNA interference (RNA-i): A role for nautilus in embryonic somatic muscle formation," Proc Natl Acad Sci USA., 96(4):1451-1456, Feb. 16, 1999.
Mizuhara et al., "T cell activation-associated hepatic injury: mediation by tumor necrosis factors and protection by interleukin 6," J Exp Med., 179(5):1529-1537, May 1, 1994.
Mohammadi et al., "Exosomes and cancer: From oncogenic roles to therapeutic applications," IUBMB Life, 72(4):724-728, Oct. 16, 2019.
Mohan et al., "Interaction between CD40 and its ligand gp39 in the development of murine lupus nephritis," J Immunol., 154(3):1470-1480, Feb. 1, 1995.
Montesano et al., "Genetic alterations in esophageal cancer and their relevance to etiology and pathogenesis: a review," Int J Cancer., 69(3):225-235, Jun. 21, 1996.
Morrison et al., "Chimeric human antibody molecules: mouse antigen-binding domains with human constant region domains," Proc Natl Acad Sci USA., 81(21):6851-6855, Nov. 1984.
Morse et al., "Abnormalities induced by the mutant gene lpr: expansion of a unique lymphocyte subset," J Immunol., 129(6):2612-2615, Dec. 1982.
Moskowitz et al., "PD-1 Blockade with the Monoclonal Antibody Pembrolizumab (MK-3475) in Patients with Classical Hodgkin Lymphoma after Brentuximab Vedotin Failure: Preliminary Results from a Phase 1b Study (KEYNOTE-013)," Blood, 124(21):290, Dec. 6, 2014.
Moss, "Poxvirus expression vectors," Curr Top Microbiol Immunol., 158:25-38, 1992.
Moss, "Poxvirus vectors: cytoplasmic expression of transferred genes," Curr Opin Genet Dev., 3(1):86-90, Feb. 1993.
Moss, "Use of vaccinia virus as an infectious molecular cloning and expression vector," Gene Amplif Anal., 3:201-213, 1983.
Moss, "Vaccinia virus vectors," Biotechnology, 20:345-362, 1992.
Moss, "Vaccinia virus: a tool for research and vaccine development," Science, 252(5013):1662-1667, Jun. 21, 1991.
Motzer et al., "Nivolumab versus Everolimus in Advanced Renal-Cell Carcinoma," N Engl J Med., 373(19):1803-1813, Nov. 5, 2015.
Motzer et al., "Renal Cell Carcinoma," N Engl J Med., 335(12):865-75, Sep. 19, 1996.
Mukherjee et al., "DNA-PK phosphorylates histone H2AX during apoptotic DNA fragmentation in mammalian cells," DNA Repair (Amst)., 5(5):575-590, Mar. 29, 2006.
Muller et al., "Tumor-derived exosomes regulate expression of immune function-related genes in human T cell subsets," Sci. Reports, 6:20254, Feb. 4, 2016, 13 pages.
Mumprecht et al., "Programmed death 1 signaling on chronic myeloid leukemia-specific T cells results in T-cell exhaustion and disease progression," Blood, 114(8):1528-1536, May 6, 2009.
Murooka et al., "CCL5-CCR5-mediated apoptosis in T cells: Requirement for glycosaminoglycan binding and CCL5 aggregation," J Biol Chem., 281(35):25184-25194, Sep. 1, 2006.
Muyldermans, "Single domain camel antibodies: current status," J Biotechnol., 74(4):277-302, Jun. 2001.

(56) References Cited

OTHER PUBLICATIONS

Nabel et al., "Recombinant gene expression in vivo within endothelial cells of the arterial wall," Science, 244(4910):1342-1344, Jun. 16, 1989.
National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/detection/tumor-markers/print>, 8 pages.
National Comprehensive Cancer Network, "NCCN Clinical Practice Guidelines in Oncology (NCCN Guidelines): Melanoma—Version 3.2016," Jul. 7, 2016, 154 pages.
Nava-Parada et al., "Peptide vaccine given with a Toll-like receptor agonist is effective for the treatment and prevention of spontaneous breast tumors," Cancer Res., 67(3):1326-1334, Feb. 1, 2007.
Nechiporuk et al., "The mouse SCA2 gene: cDNA sequence, alternative splicing and protein expression," Hum Mol Genet., 7(8):1301-1309, Aug. 1998.
Needleman et al., "A general method applicable to the Search for similarities in the amino acid sequence of two proteins," J Mol Biol., 48(3):443-453, Mar. 1970.
Neelapu et al., "Axicabtagene Ciloleucel CAR T-Cell Therapy in Refractory Large B-Cell Lymphoma," N. Engl. J. Medicine, 377(26):2531-2544, Dec. 28, 2017.
Neer, "Vasopressin-responsive, Soluble Adenylate Cyclase from the Rat Renal Medulla," J. Biol. Chemistry, 248(10):3742-3744, May 25, 1973.
Nelson et al., "Tumor progression despite efficient tumor antigen cross-presentation and effective "arming" of tumor antigen-specific CTL," J Immunol., 166(9):5557-5566, May 1, 2001.
Nevala et al., "Evidence of systemic Th2-driven chronic inflammation in patients with metastatic melanoma," Clin Cancer Res., 15(6):1931-1939, Mar. 15, 2009.
Neves et al., "Surgical treatment of renal cancer with vena cava extension," Br J Urol., 59(5):390-395. May 1987.
Newmark et al., "Preparation and properties of adducts of streptokinase and streptokinase-plasmin complex with poly ethylene glycol and pluronic polyol F38," J Appl Biochem., 4:185-189, 1982.
Newton et al., "Clinical benefit of INCB7839, a potent and selective ADAM inhibitor, in combination with trastuzumab in patients with metastatic HER2+ breast cancer," J. Clin. Oncol., 28(15 Suppl):3025, May 2010.
Neyns et al., "Dose-dense temozolomide regimens: antitumor activity, toxicity, and immunomodulatory effects," Cancer, 116(12):2868-2877, Jun. 15, 2010.
Ngiow et al., "A Threshold Level of Intratumor CD8+ T-cell PD1 Expression Dictates Therapeutic Response to Anti-PD1," Cancer Res., 75(18):3800-3811, Sep. 15, 2015.
Nicolau et al., "In vivo expression of rat insulin after intravenous administration of the liposome-entrapped gene for rat insulin I," Proc Natl Acad Sci USA., 80(4):1068-1072, Feb. 1983.
Nielsen et al., "Melanoma vaccines: the paradox of T cell activation without clinical response," Cancer Chemother Pharmacol., 46 Suppl:S62-S66, 2000.
Nielsen et al., "Peptide nucleic acid (PNA). A DNA mimic with a peptide backbone," Bioconjug Chem., 5(1):3-7, Jan./Feb. 1994.
Nielsen et al., "Sequence-selective recognition of DNA by strand displacement with a thymine-substituted polyamide," Science, 254(5037):1497-1500, Dec. 6, 1991.
Nishimura et al., "Autoimmune dilated cardiomyopathy in PD-1 receptor-deficient mice," Science, 291(5502):319-322, Jan. 12, 2001.
Nishimura et al., "Development of lupus-like autoimmune diseases by disruption of the PD-1 gene encoding an ITIM motif-carrying immunoreceptor," Immunity, 11(2):141-151, Aug. 1999.
Nishimura et al., "Dual functions of fractalkine/CX3C ligand 1 in trafficking of perforin+/granzyme B+ cytotoxic effector lymphocytes that are defined by CX3CR1 expression," J Immunol., 168(12):6173-6180, Jun. 15, 2002.
Nishimura et al., "Immunological studies on PD-1-deficient mice: implication of PD-1 as a negative regulator for B cell responses," Int Immunol., 10(10):1563-1572, Oct. 1998.
Nishino et al., "Monitoring immune-checkpoint blockade: response evaluation and biomarker development," Nat. Reviews, 14(11):655-668, Nov. 2017.
Nisonhoff et al., "Separation of univalent fragments from the bivalent rabbit antibody molecule by reduction of disulfide bonds," Arch Biochem Biophys., 89:230-244, Aug. 1960.
Ohaegbulam et al., "Human cancer immunotherapy with antibodies to the PD-1 and PD-L1 pathway," Trends. Mol. Medicine, 21(1):24-33, Jan. 2015.
Ohigashi et al., "Clinical significance of programmed death-1 ligand-1 and programmed death-1 ligand-2 expression in human esophageal cancer," Clin Cancer Res., 11(8):2947-2953, Apr. 15, 2005.
Okazaki et al., "PD-1 and PD-1 ligands: from discovery to clinical application," Int Immunol., 19(7):813-824, Jul. 2, 2007.
Okazaki et al., "PD-1 immunoreceptor inhibits B cell receptor-mediated signaling by recruiting src homology 2-domain-containing tyrosine phosphatase 2 to phosphotyrosine," Proc Natl Acad Sci USA., 98(24):13866-13871, Nov. 20, 2001.
Opferman al., "Linear differentiation of cytotoxic effectors into memory T lymphocytes," Science, 283(5408):1745-1748, Mar. 12, 1999.
O'Reilly et al., "MEK/ERK-mediated phosphorylation of Bim is required to ensure survival of T and B lymphocytes during mitogenic stimulation," J Immunol., 183(1):261-269, Jul. 1, 2009.
Orlandi et al., "Cloning immunoglobulin variable domains for expression by the polymerase chain reaction," Proc Natl Acad Sci USA., 86(10):3833-3837, May 1989.
Orme et al., "Disparate outcomes of patients with Multiple Myeloma based on geographic distance from NCI-Designated National Cancer Centers: A SEER based analysis," Blood, 130(S1):4689, Dec. 7, 2017.
Orme et al., "Heightened cleavage of Axl receptor tyrosine kinase by ADAM metalloproteases may contribute to disease pathogenesis in SLE," Clin. Immunol., 169:58-68, Aug. 2016.
Orme et al., "Leukocyte betacatenin expression is disturbed in systemic lupus erythematosus," PLoS One, 11(8):e0161682, 14 pages.
Orme et al., "Macrophage subpopulations in systemic lupus erythematosus.," Discov. Med., 13(69):151-158, Feb. 2012.
Orme et al., "Macrophages and neutrophils in SLE—An online molecular catalog," Autoimmun. Rev., 11(5):365-372, Mar. 2012.
Ostrov et al., "Structure of murine CTLA-4 and its role in modulating T cell responsiveness," Science, 290(5492):816-819, Oct. 27, 2000.
Otano et al., "Human CD8 T cells are susceptible to TNF-mediated activation-induced cell death," Theranostics, Mar. 15, 2020, 10(10):4481-4489.
Ott et al., "Pembrolizumab in Patients With Extensive-Stage Small-Cell Lung Cancer: Results From the Phase Ib KEYNOTE-028 Study," J. Clin. Oncol., 35(34):3823-3829, Aug. 16, 2017.
Ozkaynak et al., "Programmed death-1 targeting can promote allograft survival," J Immunol., 169(11):6546-6553, Dec. 1, 2002.
Palmer et al., "Cish actively silences TCR signaling in CD8+ T cells to maintain tumor tolerance," J Exp Med., 212(12):2095-2113, Nov. 2, 2015.
Panta et al., "ATM and the catalytic subunit of DNA-dependent protein kinase activate NF-kappaB through a common MEK/extracellular signal-regulated kinase/p90(rsk) signaling pathway in response to distinct forms of DNA damage," Mol Cell Biol., 24(5):1823-1835, Mar. 2004.
Pantuck et al., "The changing natural history of renal cell carcinoma," J Urol., 166(5):1611-1623, Nov. 2001.
Pardoll, "Spinning molecular immunology into successful immunotherapy," Nat Rev Immunol., 2(4):227-238, Apr. 2002.
Pardoll., "The Blockade of Immune Checkpoints in Cancer Immunotherapy," Nat Review., 12:252-264, Apr. 2012.
Park et al., "B7—H1/CD80 interaction is required for the induction and maintenance of peripheral T-cell tolerance," Blood., 116(8):1291-1298, May 14, 2010.

(56) References Cited

OTHER PUBLICATIONS

Park et al., "Increased Response Rates to Salvage Chemotherapy Administered after PD-1/PD-L1 Inhibitors in Patients with Non-Small Cell Lung Cancer," J Thorac Oncol., 13(1):106-111, Jan. 2018.
Park et al., "PD-1 Restrains Radiotherapy-Induced Abscopal Effect," Cancer Immunol Res., 3(6):610-619, Jun. 2015.
Parker et al., "Potential utility of uroplakin III, thrombomodulin, high molecular weight cytokeratin, and cytokeratin 20 in noninvasive, invasive, and metastatic urothelial (transitional cell) carcinomas," Am J Surg Pathol., 27(1):Jan. 1-10, 2003.
Parmentier et al., "Human TH2 cells respond to cysteinyl leukotrienes through selective expression of cysteinyl leukotriene receptor 1," J. Allergy Clin. Immunology, Apr. 2012, 129(4):1136-1142.
Parry et al., "CTLA-4 and PD-1 receptors inhibit T-cell activation by distinct mechanisms," Mol Cell Biol., 25(21):9543-9553, Nov. 2005.
Parsa et al., "Loss of tumor suppressor PTEN function increases B7—H1 expression and immunoresistance in glioma," Nat Med., 13(1):84-88, Dec. 10, 2006.
Paterson et al., "The PD-L1:B7-1 pathway restrains diabetogenic effector T cells in vivo," J Immunol., 187(3):1097-1105, Aug. 1, 2011.
Patrone et al., "Nuclear Run-On Assay Using Biotin Labeling, Magnetic Bead Capture and Analysis by Fluorescence-Based RT-PCR," BioTechniques, 29(5):1012-1017, Nov. 2000.
Patsoukis et al., "Selective effects of PD-1 on Akt and Ras pathways regulate molecular components of the cell cycle and inhibit T cell proliferation," Sci Signal., 5(230):ra46, Jun. 26, 2012.
Pavelko et al., "The epitope integration site for vaccine antigens determines virus control while maintaining efficacy in an engineered cancer vaccine," Mol Ther., 21(5):1087-1095, Apr. 9, 2013.
Peach et al., "Both extracellular immunoglobulin-like domains of CD80 contain residues critical for binding T cell surface receptors CTLA-4 and CD28," J Biol Chem., 270(36):21181-21187, Sep. 8, 1995.
Pece and Gutkind, "Signaling from E-cadherins to the MAPK pathway by the recruitment and activation of epidermal growth factor receptors upon cell-cell contact formation," J Biol Chem., 275(52):41227-41233, Dec. 29, 2000.
Pedraza-Alva et al., "Activation of p38 MAP kinase by DNA double-strand breaks in V(D)J recombination induces a G2/M cell cycle checkpoint," EMBO J., 25(4):763-773, Feb. 2, 2006.
Peghini et al, [Immunophaenotyping in the diagnosis of lymphoma]. Praxis (Bern 1994)., 93(41):1687-1692, Oct. 6, 2004, Article in German, English abstract included.
Pei et al., "FKBP51 affects cancer cell response to chemotherapy by negatively regulating Akt," Cancer Cell., 16(3):259-266, Sep. 8, 2009.
Peng et al., "PD-1 blockade enhances T-cell migration to tumors by elevating IFN-gamma inducible chemokines," Cancer Res, 72(20):5209-5218, Oct. 15, 2012.
Penix et al., "Two essential regulatory elements in the human interferon gamma promoter confer activation specific expression in T cells," J Exp Med., 178(5):1483-1496, Nov. 1, 1993.
Perriman et al., "Effective ribozyme delivery in plant cells," Proc Natl Acad Sci USA., 92(13):6175-6179, Jun. 20, 1995.
Petroff et al., "B7 family molecules: novel immunomodulators at the maternal-fetal interface," Placenta, 23 Suppl A:S95-101, Apr. 2002.
Piccini, "Vaccinia: virus, vector, vaccine," Adv Virus Res., 34:43-64, 1988.
Pitt et al., "Resistance Mechanisms to Immune-Checkpoint Blockade in Cancer: Tumor-Intrinsic and -Extrinsic Factors," Immunity, 44(6):1255-1269, Jun. 21, 2016.
Pluckthun et al., "Expression of functional antibody Fv and Fab fragments in *Escherichia coli*," Methods Enzymol., 178:497-515, 1989.
Pluckthun, "Antibodies from *Escherichia coli*." The Pharmacology of Monoclonal Antibodies. Handbook of Experimental Pharmacology, Springer Berlin Heidelberg, pp. 269-315, 1994.
Poirier, "Protective immunity evoked by oral administration of attenuated aroA *Salmonella typhimurium* expressing cloned streptococcal M protein," J Exp Med., 168(1):25-32, Jul. 1, 1988.
Pollok et al., "4-1BB T-cell antigen binds to mature B cells and macrophages, and costimulates anti-mu-primed splenic B cells," Eur J Immunol., 24(2):367-374, Feb. 1994.
Pollok et al., "Inducible T Cell Antigen 4-1BB," J Immunol., 150(3):771-781, Feb. 1, 1993.
Ponder et al., "Tertiary templates for proteins. Use of packing criteria in the enumeration of allowed sequences for different structural classes," J Mol Biol., 193(4):775-791, Feb. 20, 1987.
Porter et al., "Chimeric antigen receptor T cells persist and induce sustained remissions in relapsed refractory chronic lymphocytic leukemia," Sci. Transl. Medicine, 7(303):303ra139, Sep. 2, 2015, 13 pages.
Porter et al., "Chimeric antigen receptor-modified T cells in chronic lymphoid leukemia," N. Engl. J. Medicine, 365(8):725-733, Aug. 25, 2011.
Porter, "The hydrolysis of rabbit γ-globulin and antibodies with crystalline papain," Biochem J., 73:119-126, Sep. 1959.
Porteus et al., "Gene targeting using zinc finger nucleases," Nat. Biotechnology, Aug. 2005, 23(8):967-973.
Postow et al., "Immune Checkpoint Blockade in Cancer Therapy," J. Clin. Oncology, 33(17):1974-1982, Jun. 10, 2015.
Powell et al., "Compendium of excipients for parenteral formulations," PDA J Pharm Sci Technol., 52(5):238-311, Sep./Oct. 1998.
Powles et al., "MPDL3280A (anti-PD-L1) treatment leads to clinical activity in metastatic bladder cancer," Nature, 515(7528):558-562, Nov. 27, 2014.
Prabhu et al., "Gamma interferon regulates contraction of the influenza virus-specific CD8 T cell response and limits the size of the memory population," J Virol., 87(23):12510-12522, Dec. 2013.
Prasad et al., "B7S1, a novel B7 family member that negatively regulates T cell activation," Immunity, 18(6):863-873, Jun. 2003.
Presta, "Antibody engineering," Curr Opin Biotechnol., 2(4):593-596, 1992.
Presta, "Antibody engineering," Curr Opin Biotechnol., 3(4):394-398, Aug. 1992.
Prévost-Blondel et al., "Tumor-infiltrating lymphocytes exhibiting high ex vivo cytolytic activity fail to prevent murine melanoma tumor growth in vivo," J Immunol., 161(5):2187-2194, Sep. 1, 1998.
Prlic et al., "Exploring regulatory mechanisms of CD8+ T cell contraction," Proc Natl Acad Sci USA., 105(43):16689-16694, Oct. 28, 2008.
PRNewswire.com [online], "Global $4.92 Billion Programmed Death-1 (PD-1) & Programmed Death Ligand-1 (PD-L1) Inhibitors Pipeline Analysis 2017-2025—Research and Markets," Mar. 13, 2017, retrieved on Mar. 25, 2021, retrieved from URL<https://www.prnewswire.com/news-releases/global-492-billion-programmed-death-1-pd-1--programmed-death-ligand-1-pd-11-inhibitors-pipeline-analysis-2017-2025---research-and-markets-300422553.html>, 3 pages.
Probst-Cousin et al., "Annexin-1 is no useful surrogate marker of multiple sclerosis—an immunocytochemical study of the cerebrospinal fluid," Clin. Neuropathol., 30(1):Jan. 18-24, 2011.
Pu et al., "Mechanisms and functions of lysosome positioning," J Cell Sci., 129(23):4329-4339, Dec. 2016.
Pulko et al., "B7—H1 expressed by activated CD8 T cells is essential for their survival," J Immunol., 187(11):5606-5614, Oct. 24, 2011.
Pulko et al., "TLR3-stimulated dendritic cells up-regulate B7—H1 expression and influence the magnitude of CD8 T cell responses to tumor vaccination," J Immunol., 183(6):3634-3641, Aug. 26, 2009.
Qi et al., "Evidence that Ser87 of BimEL is phosphorylated by Akt and regulates BimEL apoptotic function," J Biol Chem., 281(2):813-823, Nov. 10, 2005.
Radhakrishnan et al., "Dendritic cells activated by cross-linking B7-DC (PD-L2) block inflammatory airway disease," J Allergy Clin Immunol., 116(3):668-674, Sep. 2005.

(56) References Cited

OTHER PUBLICATIONS

Rai et al., "Tracking the total CD8 T cell response to infection reveals substantial discordance in magnitude and kinetics between inbred and outbred hosts," J Immunol., 183(12):7672-7681, Dec. 15, 2009.
Rajewsky et al., "Genetics, expression, and function of idiotypes," Annu Rev Immunol., 1:569-607, 1983.
Rathmell et al., "The central effectors of cell death in the immune system," Annu. Rev. Immunol., 17:781-828, 1999.
Razi-Wolf, "Expression and function of the murine B7 antigen, the major costimulatory molecule expressed by peritoneal exudate cells," Proc Natl Acad Sci USA., 89(9):4210-4214, May 1, 1992.
Refaeli et al., "Interferon gamma is required for activation-induced death of T lymphocytes," J Exp Med., 196(7):999-1005, Oct. 7, 2002.
Ren et al., "Analysis of the Effects of the Bruton's tyrosine kinase (Btk) Inhibitor Ibrutinib on Monocyte Fcgamma Receptor (FcgammaR) Function," J. Biol. Chemistry, Feb. 5, 2016, 291(6):3043-3052.
Renauld et al., "Expression cloning of the murine and human interleukin 9 receptor cDNAs," Proc Natl Acad Sci USA., 89(12):5690-5694, Jun. 15, 1992.
Ribas et al., "Association of Pembrolizumab With Tumor Response and Survival Among Patients With Advanced Melanoma," JAMA, 315(15):1600-1609, Apr. 19, 2016.
Ribas et al., "Pembrolizumab versus investigator-choice chemotherapy for ipilimumab-refractory melanoma (KEYNOTE-002): a randomised, controlled, phase 2 trial," Lancet Oncol., 16(8):908-918, Aug. 2015.
Riechmann et al., "Reshaping human antibodies for therapy," Nature, 332(6162):323-327, Mar. 24, 1988.
Rincon et al., "JNK and p38 MAP kinases in CD4+ and CD8+ T cells," Immunol Rev., 192:131-142, Apr. 2003.
Rios-Doria et al., "A Monoclonal Antibody to ADAM17 Inhibits Tumor Growith by Inhibiting EGFR and Non-EGFR-Mediated Pathways," Mol. Cancer Ther., 14(7):1637-1649, Jul. 2015.
Rios-Doria et al., "Doxil synergizes with cancer immunotherapies to enhance antitumor responses in syngeneic mouse models," Neoplasia, 17(8):661-670, Aug. 2015.
Ritz et al., "Bioassay analysis using R," J Stat Softw., 12(5):1-22, Jan. 19, 2005.
Rivoltini et al., "Immunity to cancer: attack and escape in T lymphocyte-tumor cell interaction," Immunol Rev., 188:97-113, Oct. 2002.
Rizvi et al., "Nivolumab in Combination With Platinum-Based Doublet Chemotherapy for First-Line Treatment of Advanced Non-Small-Cell Lung Cancer," J Clin Oncol., 34(25):2969-2979, Sep. 1, 2016.
Robbins et al., "Regulation of immune responses by extracellular vesicles," Nat. Rev. Immunology, 14(3):195-208, Feb. 25, 2014.
Robert et al., "Anti-programmed-death-receptor-1 treatment with pembrolizumab in ipilimumab-refractory advanced melanoma: a randomised dose-comparison cohort of a phase 1 trial," Lancet, 384(9948):1109-1117, Sep. 20, 2014.
Robert et al., "Nivolumab in previously untreated melanoma without BRAF mutation," N Engl J Med., 372(4):320-330, Jan. 22, 2015.
Robert et al., "Pembrolizumab versus Ipilimumab in Advanced Melanoma," N Engl J Med., 372(26):2521-2532, Jun. 25, 2015.
Robison-Cox, "Multiple estimation of concentrations in immunoassay using logistic models," J Immunol Methods, 186(1):79-88, Oct. 12, 1995.
Romano et al., "Quelling: transient inactivation of gene expression in Neurospora crassa by transformation with homologous sequences," Mol Microbiol., 6(22):3343-3353, Nov. 1992.
Romer et al., "Plant pathogen recognition mediated by promoter activation of the pepper Bs3 resistance gene," Science, 318(5850):645-648, Oct. 26, 2007.
Romero et al., "Ex vivo staining of metastatic lymph nodes by class I major histocompatibility complex tetramers reveals high numbers of antigen-experienced tumor-specific cytolytic T lymphocytes," J Exp Med., 188(9):1641-1650, Nov. 2, 1998.
Romero et al., "Four functionally distinct populations of human effector-memory CD8+ T lymphocytes," J Immunol., 178(7):4112-4119, Apr. 1, 2007.
Roos et al., "DNA damage and the balance between survival and death in cancer biology," Nat. Rev. Cancer, 16(1):20-33, Jan. 2016.
Rosenberg, "Progress in human tumor immunology and immunotherapy," Nature, 411(6835):380-384, May 17, 2001.
Rosenfeld et al., "Adenovirus-mediated transfer of a recombinant alpha 1-antitrypsin gene to the lung epithelium in vivo," Science, 252(5004):431-434, Apr. 19, 1991.
Rousseaux et al, "Optimal conditions for the preparation of proteolytic fragments from monoclonal IgG of different rat IgG subclasses," Methods Enzymol., 121:663-669, 1986.
Rowe et al., "PDL-1 blockade impedes T cell expansion and protective immunity primed by attenuated Listeria monocytogenes," J Immunol., 180(11):7553-7557, Jun. 1, 2008.
Ruella et al., "Combination of Anti-CD123 and Anti-CD19 Chimeric Antigen Receptor T Cells for the Treatment and Prevention of Antigen-Loss Relapses Occurring after CD19-Targeted Immunotherapies," Blood, 126(23):2523, Dec. 3, 2015, 8 pages.
Ruella et al., "Overcoming the Immunosuppressive Tumor Microenvironment of Hodgkin Lymphoma Using Chimeric Antigen Receptor T Cells," Cancer Discovery, 7(10):1154-1167, Oct. 2017.
Ruppert et al., "The major isoforms of Bim contribute to distinct biological activities that govern the processes of autophagy and apoptosis in interleukin-7 dependent lymphocytes," Biochim Biophys Acta., 1823(10):1877-1893, Oct. 2012.
Sadoff, "Oral *Salmonella typhimurium* vaccine expressing circumsporozoite protein protects against malaria," Science, 240(4850):336-338, Apr. 15, 1988.
Saito et al., "Metformin suppresses the growth of leukemia cells partly through downregulation of AXL receptor tyrosine kinase," Leukemia Research, May 15, 2020, 94:106383, 6 pages.
Sakemura et al., "Targeting Cancer Associated Fibroblasts in the Bone Marrow Prevents Resistance to Chimeric Antigen Receptor T Cell Therapy in Multiple Myeloma," Blood, 134(Supplement_1):865, Nov. 13, 2019, 7 pages.
Salama et al., "Critical role of the programmed death-1 (PD-1) pathway in regulation of experimental autoimmune encephalomyelitis," J Exp Med., 198(1):71-78, Jul. 7, 2003.
Salib et al., "Utilization of sodium alginate in drug microencapsulation," Pharm Ind., 40(11a):1230-1234, 1978.
Salih et al., "4-1 BB ligand—just another costimulating molecule?," Int J Clin Pharmacol Ther., 40(8):348-353, Aug. 2002.
Salih et al., "The role of leukemia-derived B7—H1 (PD-L1) in tumor-T-call interactions in humans," Exp Hematol., 34(7):888-894, Jul. 2006.
Sallusto et al., "Two subsets of memory T lymphocytes with distinct homing potentials and effector functions," Nature, 401(6754):708-712, Oct. 14, 1999.
Salomon et al., "Complexities of CD28/B7: CTLA-4 costimulatory pathways in autoimmunity and transplantation," Annu Rev Immunol., 19:225-252, 2001.
Sampson et al., "Greater chemotherapy-induced lymphopenia enhances tumor-specific immune responses that eliminate EGFRvIII-expressing tumor cells in patients with glioblastoma," Neuro Oncol., 13(3):324-333, Dec. 10, 2010.
Samulski, "Targeted integration of adenoassociated virus (AAV) into human chromosome 19," EMBO J., 10(12):3941-3950, Dec. 1991.
Sandhu, "Protein engineering of antibodies," Crit Rev Biotechnol., 12(5-6):437-462, 1992.
Sanjana et al., "Improved vectors and genome-wide libraries for CRISPR screening," Nat. Methods, 11(8):783-784, Aug. 2014.
Sanni et al., "Evolution of aminoacyl-tRNA synthetase quaternary structure and activity: *Saccharomyces cerevisiae* mitochondrial phenylalanyl-tRNA synthetase," Proc Natl Acad Sci USA., 88(19):8387-8391, Oct. 1, 1991.
Sarbassov et al., "Phosphorylation and regulation of Akt/PKB by the rictor-mTOR complex," Science, 307(5712):1098-1101, Feb. 18, 2005.

(56) References Cited

OTHER PUBLICATIONS

Satelli et al., "Potential role of nuclear PD-L1 expression in cell-surface vimentin positive circulating tumor cells as a prognostic marker in cancer patients," Sci Rep., 6:28910, Jul. 1, 2016, 7 pages.
Sawhney et al., "Bioerodible hydrogels based on photopolymerized poly(ethylene glycol)-co-poly(.alpha.-hydroxy acid) diacrylate macromers," Macromolecules, 26(4):581-587, Jul. 1993.
Schafer, "Induction of a cellular immune response to a foreign antigen by a recombinant Listeria monocytogenes vaccine," J Immunol., 149(1):53-59, Jul. 1, 1992.
Schinkel et al., "Mammalian drug efflux transporters of the ATP binding cassette (ABC) family: an overview," Adv Drug Deliv Rev., 55(1):3-29, Jan. 21, 2003.
Schmid et al, "Expression of AMPA receptor subunit flip/flop splice variants in the rat auditory brainstem and inferior colliculus," J Comp Neurol., 430(2):160-171, Feb. 5, 2001.
Schmidt et al., "Extreme CD8 T cell requirements for anti-malarial liver-stage immunity following immunization with radiation attenuated sporozoites," PLoS Pathog., 6(7):e1000998, Jul. 15, 2010.
Schmits et al., "LFA-1-deficient mice show normal CTL responses to virus but fail to reject immunogenic tumor," J Exp Med., 183(4):1415-1426, Apr. 1, 1996.
Schornack et al., "Gene-for-gene-mediated recognition of nuclear-targeted AvrBs3-like bacterial effector proteins," J. Plant Physiology, 163(3):256-272, Feb. 2006.
Schoumacher et al., "Key Roles of AXL and MER Receptor Tyrosine Kinases in Resistance to Multiple Anticancer Therapies," Curr. Oncol. Rep. Curr. Science, Mar. 2017, 19(3):19, 14 pages.
Schurich et al., "The third signal cytokine IL-12 rescues the anti-viral function of exhausted HBV-specific CD8 T cells," PLoS Pathog., 9(3):e1003208, Mar. 14, 2013.
Schuster et al., "Chimeric Antigen Receptor T Cells in Refractory B-Cell Lymphomas," N. Engl. J. Medicine, 377(26):2545-2554, Dec. 28, 2017.
Schwartz et al, "Costimulation of T lymphocytes: the role of CD28, CTLA-4, and B7/BBI in interluekin-2 production and immunotherapy," Cell, 71(7):1065-1068, Dec. 24, 1992.
Schwartz et al., "Structural basis for co-stimulation by the human CTLA-4/B7-2 complex," Nature, 410(6828):604-608, Mar. 29, 2001.
Schwartz et al., "Structural mechanisms of costimulation," Nat Immunol., 3(5):427-434, May 2002.
Sedletska et al., "Cisplatin is a DNA-damaging antitumour compound triggering multifactorial biochemical responses in cancer cells: importance of apoptotic pathways," Curr Med Chem Anticancer Agents., 5(3):251-265, May 2005.
Seiwert et al., "Antitumor activity and safety of pembrolizumab in patients (pts) with advanced squamous cell carcinoma of the head and neck (SCCHN): Preliminary results from KEYNOTE-012 expansion cohort," J. Clin. Oncol., 33(18 Suppl):LBA6008, Jun. 20, 2015.
Seki et al., "Tumor-specific CTL kill murine renal cancer cells using both perforin and Fas ligand-mediated lysis in vitro, but cause tumor regression in vivo in the absence of perforin," J Immunol., 168(7):3484-3492, Apr. 1, 2002.
Selenko-Gebauer et al., "B7-III (programmed death-1 ligand) on dendritic cells is involved in the induction and maintenance of T cell anergy," J Immunol., 170(7):3637-3644, Apr. 1, 2003.
Seo et al., "Blockade of endogenous B7—H1 suppresses antibacterial protection after primary Listeria monocytogenes infection," Immunology, 123(1):90-99, Oct. 25, 2007.
Seymour et al., "iRECIST: guidelines for response criteria for use in trials testing immunotherapeutics," Lancet Oncol., 18(3):e143-e152, Mar. 2017.
Shaknovich et al., "The promyelocytic leukemia zinc finger protein affects myeloid cell growth, differentiation, and apoptosis," Mol Cell Biol., 18(9):5533-5545, Sep. 1998.
Shalem et al., "Genome-scale CRISPR-Cas9 knockout screening in human cells," Science, 343(6166):84-87, Jan. 3, 2014.

Shao et al., "Deficiency of the DNA repair enzyme ATM in rheumatoid arthritis," J Exp Med., 206(6):1435-1449, May 18, 2009.
Shao et al., "DNA-dependent protein kinase catalytic subunit mediates T-cell loss in rheumatoid arthritis," EMBO Mol Med., 2(10):415-427, Oct. 2010.
Shao et al., "ERK2 phosphorylation of serine 77 regulates Bmf pro-apoptotic activity," Cell Death Dis., 3(1):e253, Jan. 19, 2012, 10 pages.
Sharma et al., "Immune checkpoint targeting in cancer therapy: toward combination strategies with curative potential," Cell, 161(2):205-214, Apr. 9, 2015.
Sharma et al., "The future of immune checkpoint therapy," Science, 348(6230):56-61, Apr. 3, 2015.
Sharon et al., "Preparation of Fv fragment from the mouse myeloma XRPC-25 immunoglobulin possessing anti-dinitrophenyl activity," Biochemistry, 15(7):1591-1594, Apr. 6, 1976.
Sheather, "Density Estimation," Statistical Sci., 19(4):588-597, 2004.
Shenoy et al., "Exosomes Associated with Human Ovarian Tumors Harbor a Reversible Checkpoint of T-cell Responses," Cancer Immunol. Research, 6(2):236-247, Feb. 2018.
Shenoy et al., "IL-15 regulates Bcl-2 family members Bim and Mcl-1 through JAK/STAT and PI3K/AKT pathways in T cells," Eur J Immunology, 44(8):2500-2507, Aug. 2014.
Shin et al., "Cooperative B7-½ (CD80/CD86) and B7-DC costimulation of CD4+ T cells independent of the PD-1 receptor," J Exp Med., 198(1):31-38, Jul. 7, 2003.
Sica et al., "B7—H4, a molecule of the B7 family, negatively regulates T cell immunity," Immunity, 18(6):849-861, Jun. 2003.
Sica et al., "Biochemical and immunological characteristics of 4-1BB (CD137) receptor and ligand and potential applications in cancer therapy," Arch Immunol Ther Exp (Warsz)., 47(5):275-279, 1999.
Siddiqi et al., "Rapid Undetectable MRD (uMRD) Responses in Patients with Relapsed/Refractory (R/R) Chronic Lymphocytic Leukemia/Small Lymphocytic Lymphoma (CLL/SLL) Treated with Lisocabtagene Maraleucel (liso-cel), a CD19-Directed Car T Cell Product: Updated Results from Transcend CLL 004, a Phase ½ Study Including Patients with High-Risk Disease Previously Treated with Ibrutinib," Blood, 134(Suppl 1):503, Nov. 13, 2019, 7 pages.
Siddiqui et al., "Enhanced recruitment of genetically modified CX3CR1-positive human T cells into Fractalkine/CX3CL1 expressing tumors: importance of the chemokine gradient," J. Immunotherapy, 4:21, Apr. 19, 2016, 12 pages.
Siddiqui et al., "Tumor-infiltrating Foxp3-CD4+CD25+ T cells predict poor survival in renal cell carcinoma," Clin Cancer Res., 13(7):2075-2081, Apr. 1, 2007.
Simon et al., "B7—H4 is a novel membrane-bound protein and a candidate serum and tissue biomarker for ovarian cancer," Cancer Res., 66(3):1570-1575, Feb. 1, 2006.
Singer et al., "Optimal humanization of 1B4, an Anti-CD18 murine monoclonal antibody, is achieved by correct choice of human v-region framework sequences," J Immunol., 150(7):2844-2857, Apr. 1, 1993.
Skerra et al., "Assembly of a functional immunoglobulin Fv fragment in *Escherichia coli*," Science, 240(4855):1038-1041, May 20, 1988.
Skolnick et al., "From genes to protein structure and function: novel applications of computational approaches in the genomic era," Trends Biotechnol., 18(1):34-39, Jan. 2000.
Smallwood et al., "Extracellular vesicles released by CD40/IL-4-stimulated CLL cells confer altered functional properties to CD4+ T cells," Blood, 128(4):542-552, Jul. 28, 2016.
Smith et al., Differential outcome of IL-2/anti-IL-2 complex therapy on effector and memory CD8+ T cells following vaccination with an adenoviral vector encoding EBV epitopes, J Immunol., 186(10):5784-5790, Apr. 11, 2011.
Smith et al., "Pulmonary deposition and clearance of aerosolized alpha-1-proteinase inhibitor administered to dogs and to sheep," J Clin Invest., 84(4):1145-1154, Oct. 1989.

(56) References Cited

OTHER PUBLICATIONS

Sneller et al., "A novel lymphoproliferative/autoimmune syndrome resembling murine lpr/gld disease," J Clin Invest., 90(2):334-341, Aug. 1992.
Solier et al., "Death receptor-induced activation of the Chk2- and histone H2AX-associated DNA damage response pathways," Mol Cell Biol., 29(1):68-82, Oct. 27, 2008.
Sorge et al., "Amphotropic retrovirus vector system for human cell gene transfer," Mol Cell Biol., 4(9):1730-1737, Sep. 1984.
Soriano, "Targeted and nontargeted liposomes for in vivo transfer to rat liver cells of a plasmid containing the preproinsulin I gene," Proc Natl Acad Sci USA., 80(23):7128-7131, Dec. 1983.
Sotillo et al., "Convergence of Acquired Mutations and Alternative Splicing of CD19 Enables Resistance to CART-19 Immunotherapy," Cancer Discovery, 5(12):1282-1295, Dec. 2015.
Soubeyrand et al., "Artemis phosphorylated by DNA-dependent protein kinase associates preferentially with discrete regions of chromatin," J Mol Biol., 358(5):1200-1211, Mar. 20, 2006.
Stammers et al., "BTL-II: A polymorphic locus with homology to the butyrolphilin gene family, located at the border of the major histocompatibility complex class II and class III regions in human and mouse," Immunogenetics, 51(4-5):373-382, Apr. 2000.
Stamper et al., "Crystal structure of the B7-1/CTLA-4 complex that inhibits human immune responses," Nature, 410(6828):608-611, Mar. 29, 2001.
Sterner et al., "GM-CSF inhibition reduces cytokine release syndrome and neuroinflammation but enhances CAR-T cell function in xenografts," Blood, 133(7):697-709, Feb. 14, 2019.
Sterner et al., "Myeloid cell and cytokine interactions with chimeric antigen receptor-T-cell therapy: implication for future therapies," Curr. Opin. Hematology, 27(1):41-48, Jan. 2020.
Sterner et al., "Using CRISPR/Cas9 to Knock Out GMCSF in CAR-T Cells," J. Vis. Experiments, 149:e59629, Jul. 2019, 6 pages.
Stoklasek et al., "Combined IL-15/IL-15Ralpha immunotherapy maximizes IL-15 activity in vivo," J Immunol., 177(9):6072-6080, Nov. 1, 2006.
Strasser, "The role of BH3-only proteins in the immune system," Nat Rev Immunol., 5:189-200, Feb. 18, 2005.
Strome et al., "B7—H1 blockade augments adoptive T-cell immunotherapy for squamous cell carcinoma," Cancer Res., 63(19):6501-6505, Oct. 1, 2003.
Strome et al., "Enhanced therapeutic potential of adoptive immunotherapy by in vitro CD28/4-1BB costimulation of tumor-reactive T cells against a poorly immunogenic, major histocompatibility complex class 1-negative A9P melanoma," J Immunother., 23(4):430-437, Jul./Aug. 2000.
Stroncek et al., "Myeloid cells in peripheral blood mononuclear cell concentrates inhibit the expansion of chimeric antigen receptor T cells," Cytotherapy, 18(7):893-901, Jul. 2016.
Subudhi et al., "Local expression of B7—H1 promotes organ-specific autoimmunity and transplant rejection," J Clin Invest., 113(5):694-700, Mar. 2004.
Suda et al., "Why do defects in the Fas-Fas ligand system cause autoimmunity?" J Allergy Clin Immunol., 100(6 Pt 2):S97-S101, Dec. 1997.
Sugio et al., "Two type III effector genes of *Xanthomonas oryzae* pv. *oryzae* control the induction of the host genes OsTFIIAγ1 and OsTFX1 during bacterial blight of rice," Proc. Natl. Acad. Sci. USA, 104(25):10720-10725, Jun. 19, 2007.
Summerton et al., "Morpholino antisense oligomers: design, preparation, and properties," Antisense Nucleic Acid Drug Dev., 7(3):187-195, Jun. 1997.
Sun et al., "CAP-miRSeq: a comprehensive analysis pipeline for microRNA sequencing data," BMC Genomics, 15:423, Jun. 3, 2014, 10 pages.
Sun et al., "Administration of agonistic anti-4-1BB monoclonal antibody leads to the amelioration of experimental autoimmune encephalomyelitis," J Immunol., 168(3):1457-1465, Feb. 1, 2002.
Sun et al., "Costimulatory molecule-targeted antibody therapy of a spontaneous autoimmune disease," Nat Med., 8(12):1405-1413, Nov. 11, 2002.
Sun et al., "Signaling of 4-1BB Leads to Amelioration of Experimental Autoimmune Encephalomyelitis," FASEB J., vol. 5, p. A1210 Abstract 950.9, 2001.
Sutter et al., "Nonreplicating vaccinia vector efficiently expresses recombinant genes," Proc Natl Acad Sci USA., 89(22):10847-10851, Nov. 15, 1992.
Suzuki et al., "T cell-specific loss of Pten leads to defects in central and peripheral tolerance," Immunity, 14(5):523-534, May 2001.
Suzuki et al., "The dual functions of fas ligand in the regulation of peripheral CD8+ and CD4+ T cells," Proc Natl Acad Sci USA., 97(4):1707-1712, Feb. 15, 2000.
Swallow et al., "B7h, a novel costimulatory homolog of B7.1 and B7.2, is induced by TNFalpha," Immunity, 11(4):423-432, Oct. 1999.
Szajnik et al., "Tumor-derived microvesicles induce, expand and up-regulate biological activities of human regulatory T cells (Treg)," PLoS One, 5(7):e11469, Jul. 22, 2010, 13 pages.
Takahashi et al., "Serum levels of soluble programmed cell death ligand 1 as a prognostic factor on the first-line treatment of metastatic or recurrent gastric cancer," J. Cancer Res. Clin. Oncol., 142(8):1727-1738, Aug. 2016.
Takahashi et al., "Cutting edge: 4-1BB is a bona fide CD8 T cell survival signal," J Immunol., 162(9):5037-5040, May 1, 1999.
Takeda et al., "Critical contribution of liver natural killer T cells to a murine model of hepatitis," Proc Natl Acad Sci USA., 97(10):5498-5503, May 9, 2000.
Tamura et al., "B7—H1 costimulation preferentially enhances CD28-indepenent T-helper cell function," Blood, 97(6):1809-1816, Mar. 15, 2001.
Tamura et al., "Marrow stromal cells induce B7—H1 expression on myeloma cells, generating aggressive characteristics in multiple myeloma," Leukemia, 27(2):464-472, 2013.
Taylor et al., "Glycogen Synthase Kinase 3 Inactivation Drives T-bet-Mediated Downregulation of Co-receptor PD-1 to Enhance CD8(+) Cytolytic T Cell Responses," Immunity, 44(2):274-286, Feb. 16, 2016.
Taylor et al., "Tumour-derived exosomes and their role in cancer-associated Tcell signalling defects," Br. J. Cancer, 92(2):305-311, Jan. 18, 2005.
Taylor et al., "Human immunoglobulin transgenes undergo rearrangement, somatic mutation and class switching in mice that lack endogenous IgM," Int Immunol., 6(4):579-591, Apr. 1994.
Tazi-Ahnini et al., "Cloning, localization, and structure of new members of the butyrophilin gene family in the juxtatelomene region of the major histocompatibility complex," Immunogenetics, 47(1):55-63, 1997.
Teh et al., "TNF receptor 2-deficient CD8 T cells are resistant to Fas/Fas ligand-induced cell death," J. Immunology, Nov. 1, 2000, 165(9):4814-4821.
Temin, "Safety considerations in somatic gene therapy of human disease with retrovirus vectors," Hum Gene Ther., 1(2):111-123, Summer 1990.
Templeton et al., "Improved DNA: liposome complexes for increased systemic delivery and gene expression," Nat Biotechnol., 15(7):647-652, Jul. 1997.
Tham et al., "Melanoma-initiating cells exploit M2 macrophage TGFbeta and arginase pathway for survival and proliferation," Oncotarget, 5(23):12027-12042, Dec. 15, 2014.
Theofilopoulos et al., "Tumour necrosis factor and other cytokines in murine lupus," Ann Rheum Dis., 58(suppl 1):149-55, Nov. 1, 1999.
Theofilopoulos et al., "Etiopathogenesis of Murine SLE," Immunol Rev., 55:179-216, 1981.
Thery et al., "Minimal information for studies of extracellular vesicles 2018 (MISEV2018): a position statement of the International Society for Extracellular Vesicles and update of the MISEV2014 guidelines," J. Extracell. Vesicles, 7(1):1535750, Nov. 23, 2018, 47 pages.

(56) References Cited

OTHER PUBLICATIONS

Thompson et al., "cis-acting sequences required for inducible interleukin-2 enhancer function bind a novel Ets-related protein, Elf-1," Mol Cell Biol., 12(3):1043-1053, Mar. 1992.
Thompson et al., "Costimulatory B7—H1 in renal cell carcinoma patients: Indicator of tumor aggressiveness and potential therapeutic target," Proc Natl Acad Sci USA., 101(49):17174-17179, Nov. 29, 2004.
Thompson et al., "Costimulatory molecule B7—H1 in primary and metastatic clear cell renal cell carcinoma," Cancer, 104(10):2084-2091, Nov. 15, 2005.
Thompson et al., "PD-1 is expressed by tumor-infiltrating immune cells and is associated with poor outcome for patients with renal cell carcinoma," Clin Cancer Res., 13(6):1757-1761, Mar. 15, 2007.
Thompson et al., "Tumor B7—H1 is associated with poor prognosis in renal cell carcinoma patients with long-term follow-up," Cancer Res., 66(7):3381-3385, Apr. 1, 2006.
Thompson et al., "Tumor masses support naive T cell infiltration, activation, and differentiation into effectors," J Exp Med., 207(8):1791-1804, Jul. 26, 2010.
Tian et al., "The relationship between the down-regulation of DNA-PKcs or Ku70 and the chemosensitization in human cervical carcinoma cell line HeLa," Oncol Rep., 18(4):927-932, Oct. 2007.
Tickner et al., "Functions and therapeutic roles of exosomes in cancer," Front. Oncology, 4:127, May 27, 2014, 8 pages.
Tiedt et al., "RNA-Seq Identifies Circulating miR-125a-Sp, miR-125b-Sp, and miR-143-3p as Potential Biomarkers for Acute Ischemic Stroke," Circ. Research, 121(8):970-980, Sep. 29, 2017.
Tiegs et al., "A T cell-dependent experimental liver injury in mice inducible by concanavalin A," J Clin Invest., 90(1):196-203, Jul. 1992.
Titomirov, "In vivo electroporation and stable transformation of skin cells of newborn mice by plasmid DNA," Biochim Biophys Acta., 1088(1):131-134, Jan. 17, 1991.
Tocknnan et al., "Considerations in bringing a cancer biomarker to clinical application," Cancer Res., 52(9 Suppl.):2711s-2718s, May 1992.
Todd et al., "Transcription of the interleukin 4 gene is regulated by multiple promoter elements," J Exp Med., 177(6):1663-1674, Jun. 1, 1993.
Topalian et al., "Safety, Activity, and Immune Correlates of Anti-PD-1 Antibody in Cancer," N Engl J Med, 366(26):2443-2454, Jun. 28, 2012.
Townsend et al., "Tumor rejection after direct costimulation of CD8+ T cells by B7-transfected melanoma cells," Science, 259(5093):368-370, Jan. 15, 1993.
Trabattoni et al. "B7—H1 is up-regulated in HIV infection and is a novel surrogate marker of disease progression" Blood, 101(7):2514-2520, Dec. 5, 2002.
Tringler et al., "B7—H4 is highly expressed in ductal and lobular breast cancer," Clin Cancer Res., 11(5):1842-1848, Mar. 1, 2005.
Truneh et al., "Early steps of lymphocyte activation bypassed by synergy between calcium ionophores and phorbol ester," Nature., 313(6000):318-320, Jan. 24, 1985.
Tsai et al., "Long noncoding RNA as modular scaffold of histone modification complexes," Science, 329(5992):689-693, Aug. 6, 2010.
Tseng et al., "B7-DC, a new dendritic cell molecule with potent costimulatory properties for T cells," J Exp Med., 193(7):839-846, Apr. 2, 2001.
Tumeh et al., "PD-1 blockade induces responses by inhibiting adaptive immune resistance," Nature, 515(7528):568-571, Nov. 27, 2014.
Turman et al., "Characterization of a novel gene (NKG7) on human chromosome 19 that is expressed in natural killer cells and T cells," Hum Immunol., 36(1):34-40, Jan. 1993.
Turtle et al., "A distinct subset of self-renewing human memory CD8+ T cells survives cytotoxic chemotherapy," Immunity, 31(5):834-844, Nov. 20, 2009.
Turtle et al., "CD19 CAR-T cells of defined CD4+:CD8+ composition in adult B cell ALL patients," J. Clin. Investigation, 126(6):2123-2138, Jun. 1, 2016.
Turtle et al., "Durable Molecular Remissions in Chronic Lymphocytic Leukemia Treated With CD19-Specific Chimeric Antigen Receptor-Modified T Cells After Failure of Ibrutinib," J. Clin. Oncology, 35(26):3010-3020, Sep. 10, 2017.
Ueda et al., "Sequence-specific DNA damage induced by reduced mitomycin C and 7-N-(p-hydroxyphenyl)mitomycin C.," Nucleic Acids Res., 12(17):6673-6683, Sep. 11, 1984.
Ueha et al., "Robust Antitumor Effects of Combined Anti-CD4-Depleting Antibody and Anti-PD-1/PD-L1 Immune Checkpoint Antibody Treatment in Mice," Cancer Immunol Res., 3(6):631-640, Jun. 2015.
Umansky et al., "Myeloid-derived suppressor cells in malignant melanoma," J Dtsch Dermatol Ges., 12(11):1021-1027, Nov. 2014.
Verhoeyen et al., "Reshaping human antibodies: grafting an antilysozyme activity," Science, 239(4847):1534-1536, Mar. 25, 1988.
Vesely et al., "Natural innate and adaptive immunity to cancer," Annu Rev Immunol., 29:235-271, 2011.
Veuger et al., "Radiosensitization and DNA repair inhibition by the combined use of novel inhibitors of DNA-dependent protein kinase and poly(ADP-ribose) polymerase-1," Cancer Res., 63(18):6008-6015, Sep. 15, 2003.
Vinay et al., "Role of 4-1BB in immune responses," Semin Immunol., 10(6):481-489, Dec. 1998.
Wahl et al., "Improved radioimaging and tumor localization with monoclonal F(ab')2" J Nucl Med., 24(4):316-25, Apr. 1983.
Wallin et al., "Atezolizumab in combination with bevacizumab enhances antigen-specific T-cell migration in metastatic renal cell carcinoma," Nat Commun., 7:12624, Aug. 30, 2016, 8 pages.
Walter et al., "The peripheral benzodiazepine receptor ligand PK11195 overcomes different resistance mechanisms to sensitize AML cells to gemtuzumab ozogamicin," Blood, 103(11):4276-4284, Jun. 1, 2004.
Walunas et al., "CTLA-4 ligation blocks CD28-dependent T cell activation," J Exp Med., 183(6):2541-2550, Jun. 1, 1996.
Wang et al., "Costimulation of T cells by B7—H2, a B7-like molecule that binds ICOS," Blood, 96(8):2808-2813, Oct. 15, 2000.
Wang et al., "Doxorubicin induces apoptosis in normal and tumor cells via distinctly different mechanisms. intermediacy of H(2)((2)- and p53-dependent pathways," J Biol Chem., 279(24):25535-25543, Mar. 30, 2004.
Wang et al., "Ligand binding sites of inducible costimulator and high avidity mutants with improved function," J Exp Med., 195(8):1033-1041, Apr. 15, 2002.
Wang et al., "Molecular modeling and functional mapping of B7—H1 and B7-DC uncouple costimulatory function from PD-1 interaction," J Exp Med., 197(9):1083-1091, Apr. 28, 2003.
Wang et al., "Multiple Functions of the RNA-Binding Protein HuR in Cancer Progression, Treatment Responses and Prognosis," Int J Mol Sci., 14(5):10015-10041, May 10, 2013.
Wang et al., "RVboost: RNA-seq variants prioritization using a boosting method," Bioinformatics, 30(23):3414-3416, Dec. 1, 2014.
Wang et al., "Serum levels of soluble programmed death ligand 1 predict treatment response and progression free survival in multiple myeloma," Oncotarget, 6(38):41228-36, Dec. 2015.
Wang, "Lyophilization and development of solid protein pharmaceuticals," Int J Pharm., 203(1-2):1-60, Aug. 10, 2000.
Wang, "pH-sensitive immunoliposomes mediate target-cell-specific delivery and controlled expression of a foreign gene in mouse," Proc Natl Acad Sci USA., 84(22):7851-7855, Nov. 1987.
Ward et al., "Binding activities of a repertoire of single immunoglobulin variable domains secreted from *Escherichia coli*," Nature, 341(6242):544-546, Oct. 12, 1989.
Webster et al., "Targeting molecular and cellular inhibitory mechanisms for improvement of antitumor memory responses reactivated by tumor cell vaccine," J Immunol., 179(5):2860-2869, Sep. 1, 2007.
Weide et al., "Myeloid-derived suppressor cells predict survival of patients with advanced melanoma: comparison with regulatory T cells and NY-ESO-1- or melan-A-specific T cells," Clin Cancer Res., 20(6):1601-1609, Mar. 15, 2014.

(56) References Cited

OTHER PUBLICATIONS

Weiss, "Hot Prospect for New Gene Amplifier: Ligase chain reaction, a combination DNA amplifier and genetic screen could do for DNA diagnostics what PCR has done for basic molecular biology," Science, 254(5036):1292-1293, Nov. 29, 1991.

Wherry et al., "Lineage relationship and protective immunity of memory CD8 T cell subsets," Nat Immunol., 4(3):225-234, Feb. 3, 2003.

Whilding et al., "CAR T-cell immunotherapy: The path from the by-road to the freeway?," Mol. Oncology, Oct. 23, 2015, 9(10):1994-2018.

White et al., "Fractalkine has anti-apoptotic and proliferative effects on human vascular smooth muscle cells via epidermal growth factor receptor signalling," Cardiovasc Res., 85(4):825-835, Mar. 1, 2010.

Wick et al., "The hepatic immune system," Crit Rev Immunol., 22(1):47-103, 2002.

Wieckowski et al., "Tumor-derived microvesicles promote regulatory T cell expansion and induce apoptosis in tumor-reactive activated CD8+ T lymphocytes," J. Immunology, 183(6):3720-3730, Sep. 15, 2009.

Wilcox et al., "Provision of antigen and CD137 signaling breaks immunological ignorance, promoting regression of poorly immunogenic tumors," J Clin Invest., 109(5):651-659, Mar. 2002.

Williams et al., "Introduction of foreign genes into tissues of living mice by DNA-coated microprojectiles," Proc Natl Acad Sci USA., 88(7):2726-2730, Apr. 1, 1991.

Williams et al., "T cell immune reconstitution following lymphodepletion," Semin Immunol., 19(5):318-330, Oct. 2007.

Williams et al., "The immunoglobulin superfamily—domains for cell surface recognition," Annu Rev Immunol., 6:381-405, 1988.

Williams et al., "Nitric oxide synthase plays a signaling role in TCR-triggered apoptotic death," J Immunol., 161(12):6526-6531, Dec. 15, 1998.

Willmore et al., "A novel DNA-dependent protein kinase inhibitor, NU7026, potentiates the cytotoxicity of topoisomerase II poisons used in the treatment of leukemia," Blood, 103(12):4659-4665, Mar. 9, 2004.

Winter et al., "Man-made antibodies," Nature, 349(6307):293-299, Jan. 24, 1991.

Winter et al., "Making antibodies by phage display technology," Annu Rev Immunol., 12:433-455, 1994.

Wintterle et al., "Expression of the B7-related molecule B7—H1 by glioma cells: a potential mechanism of immune paralysis," Cancer Res., 63(21):7462-7467, Nov. 1, 2003.

Wofsy et al., "The proliferating cells in autoimmune MRL/lpr mice lack L3T4, an antigen on "helper" T cells that is involved in the response to class II major histocompatibility antigens," J Immunol., 132(6):2686-2689, Jun. 1984.

Wofsy, "Treatment of murine lupus with anti-CD4 monoclonal antibodies," Immunol Ser., 59:221-236, 1993.

Wojciechowski et al., "Bim/Bcl-2 balance is critical for maintaining naive and memory T cell homeostasis," J Exp Med., 204(7):1665-1675, Jul. 9, 2007.

Wolff, "Direct gene transfer into mouse muscle in vivo," Science, 247(4949 Pt 1):1465-1468, Mar. 23, 1990.

Wolke et al., "Assigning the phenotype of a natural regulatory T-cell to the human T-cell line, KARPAS-299," Int J Mol Med., 17(2):275-278, Feb. 2006.

Wong et al., "Human GM-CSF: molecular cloning of the complementary DNA and purification of the natural and recombinant proteins," Science, 228(4701):810-815, May 17, 1985.

Wu et al., "Emerging roles and therapeutic value of exosomes in cancer metastasis," Mol. Cancer, 18(1):53, Mar. 30, 2019, 11 pages.

Wu et al., "Targeting B7—H1 (PD-L1) Sensitizes Cancer Cells to Chemotherapy," Heliyon, 4(12):e01039, Dec. 18, 2018, 24 pages.

Wu et al., "The double-edged sword of activation-induced cytidine deaminase," J Immunol., 174(2):934-941, Jan. 15, 2005.

Wu, "Receptor-mediated gene delivery and expression in vivo," J Biol Chem., 263(29):14621-14624, Oct. 15, 1988.

Wu, "Targeting genes: delivery and persistent expression of a foreign gene driven by mammalian regulatory elements in vivo," J Biol Chem., 264(29):16985-16987, Oct. 15, 1989.

Xu et al., "A potential new pathway for PD-L1 costimulation of the CD8-T cell response to Listeria monocytogenes infection," PLoS One, 8(2):e56539, Feb. 11, 2013, 8 pages.

Xu et al., "Autophagy is essential for effector CD8(+) T cell survival and memory formation." Nat Immunol., 15(12):1152-1161, Dec. 2014.

Xu et al., "The inducible expression of the tumor suppressor gene PTEN promotes apoptosis and decreases cell size by inhibiting the PI3K/Akt pathway in Jurkat T cells," Cell Growth Differ., 13(7):285-296, Jul. 2002.

Yamamoto et al., "B7—H1 expression is regulated by MEK/ERK signaling pathway in anaplastic large cell lymphoma and Hodgkin lymphoma," Cancer Sci., 100(11):2093-2100, Aug. 1, 2009.

Yamauchi et al., "23.02: Defining CD8+ T-cell Subsets that are Rescued by PD-1/PD-L1 Blockade in the Tumor Microenvironment," Abstract, presented at Proceedings of the 13th Annual Academic Surgical Congress, Jacksonville, FL, Jan. 30-Feb. 1, 2018, 4 pages.

Yamazaki et al., "Expression of programmed death 1 ligands by murine T cells and APC," J Immunol., 169(10):5538-5545, Nov. 15, 2002.

Yan et al., "CX3CR1 identifies PD-1 therapy-responsive CD8+ T cells that withstand chemotherapy during cancer chemoimmunotherapy," JCI Insight, 3(8):e97828, Apr. 19, 2018, 13 pages.

Yan et al., "Effect of paclitaxel and carboplatin on tumor-reactive T cells and the efficacy of PD-1 blockade," J. Clin. Oncology, 35(7S):65, Mar. 1, 2017.

Yan et al., "The Mayo Clinic experience in patients with metastatic melanoma who have failed previous pembrolizumab treatment," J Clin Oncol., 34(15 Suppl):e21014, May 20, 2016.

Yang et al., "In vitro priming of tumor-reactive cytolytic T lymphocytes by combining IL-10 with B7-CD28 costimulation," J Immunol., 155(8):3897-3903, Oct. 15, 1995.

Yang et al., "In vivo and in vitro gene transfer to mammalian somatic cells by particle bombardment," Proc Natl Acad Sci USA., 87(24):9568-9572, Dec. 1990.

Yang et al., "Os8N3 is a host disease-susceptibility gene for bacterial blight of rice," Proc. Natl. Acad. Sci. USA, 103(27):10503-10508, Jul. 5, 2006.

Yang, "Gene transfer into mammalian somatic cells in vivo," Crit Rev Biotechnol., 12(4):335-356, 1992.

Yao et al., "Interferon regulatory factor 4 sustains CD8(+) T cell expansion and effector differentiation," Immunity, 39(5):833-845, Nov. 14, 2013.

Yin et al., "Checkpoint Blockade Reverses Anergy in IL-13Ralpha2 Humanized scFv-Based CAR T Cells to Treat Murine and Canine Gliomas," Mol. Ther. Oncolytics, 11:20-38, Aug. 28, 2018.

Yin et al., "CpG-induced antitumor immunity requires IL-12 in expansion of effector cells and down-regulation of PD-1," Oncotarget, 7(43):70223-70231, Oct. 25, 2016.

Yokosuka et al., "Programmed cell death 1 forms negative costimulatory microclusters that directly inhibit T cell receptor signaling by recruiting phosphatase SHP2," J Exp Med., 209(6):1201-1217, Jun. 4, 2012.

Yoshinaga et al., "T-cell co-stimulation through B7RP-1 and ICOS," Nature, 402(6763):827-832, Dec. 16, 1999.

Yotsumoto et al., "Endosomal translocation of CpG-oligodeoxynucleotides inhibits DNA-PKcs-dependent IL-10 production in macrophages," J Immunol., 180(2):809-816, Jan. 15, 2008.

Youngnak et al., "Differential binding properties of B7—H1 and B7-DC to programmed death-1," Biochem Biophys Res Commun., 307(3):672-677, Aug. 1, 2003.

Yu et al., "Bim is required for T-cell allogeneic responses and graft-versus-host disease in vivo," Am J Blood Res., 2(1):77-85, Jan. 15, 2012.

Yuan et al., "Focus on histone variant H2AX: to be or not to b," FEBS Lett., 584(17):3717-3724, May 21, 2010.

(56) References Cited

OTHER PUBLICATIONS

Zang et al., "B7x: a widely expressed b7 family member that inhibits T cell activation," Proc Natl Acad Sci USA., 100(18):10388-10392, Aug. 14, 2003.

Zang et al., "The B7 family and cancer therapy: costimulation and coinhibition," Clin Cancer Res., 13(18 Pt 1):5271-5279, Sep. 15, 2007.

Zavialov et al., "Human adenosine deaminase 2 induces differentiation of monocytes into macrophages and stimulates proliferation of T helper cells and macrophages," J. Leukoc. Biology, Aug. 2010, 88(2):279-290.

Zeiser et al., "Acute Graft-versus-Host Disease—Biologic Process, Prevention, and Therapy," N. Engl. J. Medicine, Nov. 30, 2017, 377(22):2167-2179.

Zelenin et al., "Genetic transformation of mouse cultured cells with the help of high-velocity mechanical DNA injection," FEBS Lett., 244(1):65-67, Feb. 13, 1989.

Zelenin et al., "High-velocity mechanical DNA transfer of the chloramphenicolacetyl transferase gene into rodent liver, kidney and mammary gland cells in organ explants and in vivo," FEBS Lett., 280(1):94-96, Mar. 11, 1991.

Zhang et al., "A high M1/M2 ratio of tumor-associated macrophages is associated with extended survival in ovarian cancer patients," J Ovarian Res., 7:19, Feb. 8, 2014.

Zhang et al., "Exosomes and cancer: a newly described pathway of immune suppression," Clin. Cancer Research, 17(5):959-964, Mar. 1, 2011.

Zhang et al., "PD-1/PD-L1 interactions inhibit antitumor immune responses in a murine acute myeloid leukemia model," Blood, 114(8):1545-1552, May 5, 2009.

Zhang et al., "Theiler's virus-infected L-selectin-deficient mice have decreased infiltration of CD8(+) T lymphocytes in central nervous system but clear the virus," J Neuroimmunol., 116(2):178-187, Jun. 1, 2001.

Zhou et al., "Inducible-costimulator-mediated suppression of human immunodeficiency virus type 1 replication in CD4+ T lymphocytes," Virology, 325(2):252-263, Aug. 1, 2004.

Zitvogel et al., "Immunological aspects of cancer chemotherapy," Nat Rev Immunol., 8(1):59-73, Jan. 2008.

Zou et al., "Inhibitory B7-family molecules in the tumour microenvironment," Nat Rev Immunol., 8(6):467-477, Jun. 2008.

Zula et al., "The role of cell type-specific responses in IFN-β therapy of multiple sclerosis," Proc Natl Acad Sci USA., 108(49):19689-19694, Nov. 21, 2011.

Zumla et al. "Granulomatous infections: etiology and classification," Clin Infect Dis., 23(1):146-158, Jul. 1996.

Zwiebel et al., "Drug delivery by genetically engineered cell implants," Ann NY Acad Sci., 618:394-404, 1991.

Weitzel et al., "microRNA 184 regulates expression of NFAT1 in umbilical cord blood CD4+T cells," Blood, Jun. 25, 2009, 113(26):6648-6657.

PCT International Preliminary Report on Patentability in International Appln. No. PCT/US2019/059260, dated Apr. 27, 2021, 8 pages.

Agarwal et al., "In vivo generated human CAR T cells eradicate tumor cells," Oncoimmunology, Oct. 10, 2019, 8(12):E1671761, 7 pages.

Bender et al., "Receptor-Targeted Nipah Virus Glycoproteins Improve Cell-Type Selective Gene Delivery and Reveal a Preference for Membrane-Proximal Cell Attachment," PLOS Pathogens, Jun. 9, 2016, 12(6):E1005641, 28 pages.

Buchholz et al., "Surface-Engineered Viral Vectors for Selective and Cell Type-Specific Gene Delivery," Trends in Biotechnology, Dec. 2015, 33(12):777-790.

Extended Search Report in European Appln. No. 19879051.1, dated Dec. 14, 2022, 7 pages.

Frank et al., "Surface-Engineered Lentiviral Vectors for Selective Gene Transfer into Subtypes of Lymphocytes," Mol. Ther. Methods Clin. Development, Mar. 12, 2019:19-31.

Pfeiffer et al., "T cells results in B-cell depletion and signs of cytokine release syndrome," EMBO Mol. Medicine, Sep. 17, 2018, 10(11):E9158, 11 pages.

Zhou et al., "Exclusive Transduction of Human CD4+ T Cells upon Systemic Delivery of CD4-Targeted Lentiviral Vectors," J. Immunology, Jul. 31, 2015, 195(5):2493-2501.

Grupp et al., "T cells engineered with a chimeric antigen receptor (CAR) targeting CD19 (CTL019) produce significant in vivo proliferation, complete responses and long-term persistence without GVHD in children and adults with relapsed, refractory ALL," Blood, Nov. 15, 2013, 122(21):67, 3 pages.

Adusumilli et al., "Regional delivery of mesothelin-targeted CAR T cell therapy generates potent and long-lasting CD4-dependent tumor immunity," Sci. Transl. Medicine, Nov. 5, 2014, 6(261):261ra151, 15 pages.

Agace et al., "T-lymphocyte-epithelial-cell interactions: integrin αE(CD103)β7, LEEP-CAM and chemokines," Curr. Opin. Cell Biology, Oct. 1, 2000, 12(5):563-568.

Altschul et al., "Gapped BLAST and PSI-BLAST: a new generation of protein database search programs," Nucleic Acids Research, Sep. 1, 1997, 25(17):3389-3402.

An et al., "Anti-Multiple Myeloma Activity of Nanobody-Based Anti-CD38 Chimeric Antigen Receptor T Cells," Mol. Pharmaceutics, Sep. 5, 2018, 15(10):4577-4588.

Ao et al., "Anti-αFR CAR-engineered NK-92 Cells Display Potent Cytotoxicity Against αFR-positive Ovarian Cancer," J. Immunotherapy, Oct. 2019, 42(8):284-296.

Belov et al., "Extensive surface protein profiles of extracellular vesicles from cancer cells may provide diagnostic signatures from blood samples," J. Extracell. Vesicles, Apr. 15, 2016, 5:25355, 12 pages.

Bielamowics et al., "Trivalent CAR T cells overcome interpatient antigenic variability in glioblastoma," Neuro-Oncology, Sep. 16, 2017, 20(4):506-518.

Blat et al., "Suppression of Murine Colitis and its Associated Cancer by Carcinoembryonic Antigen-Specific Regulatory T Cells," Mol. Therapy, May 2014, 22(5):1018-1028.

Caivano et al., "Extracellular Vesicles In Hematological Malignancies: From Biology to Therapy," Int. J. Mol. Sciences, Jun. 2, 2017, 18(6):1183, 23 pages.

Caruso et al., "Tuning Sensitivity of CAR to EGFR Density Limits Recognition of Normal Tissue While Maintaining Potent Antitumor Activity," Cancer Research, Sep. 2015, 75(17):3505-3518.

Chi et al., "Significantly increased anti-tumor activity of carcinoembryonic antigen-specific chimeric antigen receptor T cells in combination with recombinant human IL-12," Cancer Medicine, Jun. 25, 2019, 8(10):4753-4765.

Chu et al., "CS1-specific chimeric antigen receptor (CAR)-engineered natural killer cells enhance in vitro and in vivo antitumor activity against human multiple myeloma," Leukemia, Apr. 2014, 28(4):917-927.

ClinicalTrials.gov [online], "First-in-human Study of Oral TP-0903 (a Novel Inhibitor of AXL Kinase) in Patients With Advanced Solid Tumors," NCT02729298, last updated Jan. 25, 2021, retrieved on Apr. 23, 2021, retrieved from URL<https://www.clinicaltrials.gov/ct2/show/NCT02729298>, 24 pages.

ClinicalTrials.gov [online], "Phase ½ Study of TP-0903 (an Inhibitor of AXL Kinase) in Patients With Previously Treated CLL," NCT03572634, last updated Feb. 2, 2021, retrieved on Apr. 23, 2021, retrieved from URL<https://clinicaltrials.gov/ct2/show/NCT03572634>, 34 pages.

Cohen et al., "B cell maturation antigen-specific CAR T cells are clinically active in multiple myeloma," J. Clin. Investigation, Mar. 21, 2019, 129(6):2210-2221.

Dahlhamer et al., "Prevalence of Inflammatory Bowel Disease Among Adults Aged≥18 Years—United States, 2015," MMWR Morb. Mortal. Wkly Report, Oct. 28, 2016, 65(42):1166-1169.

Dimopoulos et al., "Elotuzumab plus Pomalidomide and Dexamethasone for Multiple Myeloma," N. Engl. J. Medicine, Nov. 8, 2018, 379(19):1811-1822.

(56) References Cited

OTHER PUBLICATIONS

Forsberg et al., "HER2 CAR-T Cells Eradicate Uveal Melanoma and T-cell Therapy—Resistant Human Melanoma in IL2 Transgenic NOD/SCID IL2 Receptor Knockout Mice," Cancer Research, Mar. 2019, 79(5):899-904.
Forsman et al., "Size Matters: Identification of Larger Size CD19 Positive Extracellular Vesicles in Chronic Lymphocytic Leukemia That Inhibit Chimeric Antigen Receptor T Cell Functions," Blood, Nov. 29, 2018, 132(S1):1865.
Fry et al., "CD22-targeted Car T cells induce remission in B-ALL that is naive or resistant to CD19-targeted CAR immunotherapy," Nat. Medicine, Nov. 20, 2017, 24(1):20-28.
GenBank Accession No. AAH32229.1, "AXL receptor tyrosine kinase [Homo sapiens]," dated Jul. 15, 2006, 3 pages.
GenBank Accession No. EAW57023.1, "AXL receptor tyrosine kinase, isoform CRA_b [Homo sapiens]," dated Mar. 23, 2015, 2 pages.
GenBank Accession No. M76125.1, "Human tyrosine kinase receptor (axl) mRNA, complete cds," dated Jan. 14, 1995, 2 pages.
GenBank Accession No. NM_001699.5, "Homo sapiens AXL receptor tyrosine kinase (AXL), transcript variant 2, mRNA," dated Oct. 6, 2016, 5 pages.
Gill et al., "Preclinical targeting of human acute myeloid leukemia and myeloablation using chimeric antigen receptor-modified T cells," Blood, Apr. 10, 2014, 123(15):2343-2354.
Guo et al., "Axl Inhibition Induces The Antitumor Immune Response Which Can Be Further Potentiated By PD-1 Blockade in The Mouse Cancer Models," Oncotarget, Sep. 21, 2017, 8(52):89761-8977.
Haas et al., "Phase I Study of Lentiviral-Transduced Chimeric Antigen Receptor-Modified T Cells Recognizing Mesothelin in Advanced Solid Cancers," Mol. Therapy, Nov. 6, 2019, 27(11):1919-1929.
Hoffmann et al., "Only the CD45RA+ subpopulation of CD4+ CD25high T cells gives rise to homogeneous regulatory T-cell lines upon in vitro expansion," Blood, Dec. 15, 2006, 108(13):4260-4267.
Jacobsohn et al., "Acute graft versus host disease," Orphanet. J. Rare Diseases, Sep. 4, 2007, 2:35, 9 pages.
Jiang et al., "Selective Targeting of Glioblastoma with EGFRvIII/EGFR Bitargeted Chimeric Antigen Receptor T Cell," Cancer Immunol. Research, Nov. 2018, 6(11):1314-1326.
Kantarjian et al., "Inotuzumab Ozogamicin versus Standard Therapy for Acute Lymphoblastic Leukemia," N. Engl. J. Medicine, Aug. 25, 2016, 375(8):740-753.
Katz et al., "Phase I Hepatic Immunotherapy for Metastases Study of Intra-Arterial Chimeric Antigen Receptor—Modified T-cell Therapy for CEA+ Liver Metastases," Clin. Cancer Research, Jul. 2015, 21(14):3149-3159.
Kellner et al., "The Fc-engineered CD19 antibody MOR208 (XmAb5574) induces natural killer cell-mediated lysis of acute lymphoblastic leukemia cells from pediatric and adult patients," Leukemia, Jan. 1, 2013, 27(7): 1595-1598.
Kemp et al., "Lck Mediates Th2 Differentiation through Effects on T-bet and GATA-3," J. Immunology, Apr. 15, 2010, 184(8):4178-4184.
Kenderian et al., "CD33-specific chimeric antigen receptor T cells exhibit potent preclinical activity against human acute myeloid leukemia," Leukemia, Feb. 27, 2015, 29(8):1637-1647.
Koneru et al., "IL-12 secreting tumor-targeted chimeric antigen receptor T cells eradicate ovarian tumors in vivo," Oncoimmunology, Jan. 23, 2015, 4(3):e994446, 11 pages.
Kong et al., "Suppression of Human Glioma Xenografts with Second-Generation IL13R-Specific Chimeric Antigen Receptor-Modified T Cells," Clin. Cancer Research, Nov. 2012, 18(21):5949-5960.
Kreitman et al., "Moxetumomab pasudotox in relapsed/refractory hairy cell leukemia," Leukemia, Jul. 20, 2018, 32(8):1768-1777.
Laurenzana et al., "Extracellular Vesicles: A New Prospective in Crosstalk between Microenvironment and Stem Cells in Hematological Malignancies," Stem Cells International, May 27, 2018, 2018:9863194, 11 pages.
Lee et al., "Preclinical Optimization of a CD20-specific Chimeric Antigen Receptor Vector and Culture Conditions," J. Immunotherapy, Jan. 2018, 41(1):19-31.
Leuci et al., "CD44v6 as innovative sarcoma target for CAR-redirected CIK cells," Oncoimmunology, Feb. 15, 2018, 7(5):e1423167, 10 pages.
Liu et al., "RAxML and FastTree: Comparing Two Methods for Large-Scale Maximum Likelihood Phylogeny Estimation," PLoS One, Nov. 21, 2011, 6(11):e27731, 11 pages.
Liu et al., "Targeting Alpha-Fetoprotein (AFP)—MHC Complex with CAR T-Cell Therapy for Liver Cancer," Clin. Cancer Research, Jan. 2017, 23(2):478-488.
MacDonald et al., "Alloantigen-specific regulatory T cells generated with a chimeric antigen receptor," J. Clin. Investigation, Mar. 21, 2016, 126(4):1413-1424.
Martin et al., "National Institutes of Health Consensus Development Project on Criteria for Clinical Trials in Chronic Graft-versus-Host Disease: VI. The 2014 Clinical Trial Design Working Group Report," Biol. Blood Marrow Transplantation, Aug. 2015, 21(8):1343-1359.
Mejstrikova et al., "CD19-negative relapse of pediatric B-cell precursor acute lymphoblastic leukemia following blinatumomab treatment," Blood Cancer Journal, Dec. 20, 2017, 7(12):659, 5 pages.
Milone et al., "Chimeric receptors containing CD137 signal transduction domains mediate enhanced survival of T cells and increased antileukemic efficacy in vivo," Mol. Therapy, Aug. 2009, 17(8):1453-1464.
Myers et al., "AXL Inhibitors in Cancer: A Medicinal Chemistry Perspective," J. Med. Chemistry, Nov. 10, 2015, 59(8):3593-3608.
Nellan et al., "Durable regression of Medulloblastoma after regional and intravenous delivery of anti-HER2 chimeric antigen receptor T cells," J. Immunotherapy, Cancer, 6(1):30, 14 pages.
Ohnishi et al., "Prolonged survival of mice with human gastric cancer treated with an anti-c-ErbB-2 monoclonal antibody," Br. J. Cancer, May 1, 1995, 71(5):969-973.
Ormhøj et al., "Chimeric Antigen Receptor T Cells Targeting CD79b Show Efficacy in Lymphoma with or without Cotargeting CD19," Clin. Cancer Research, Dec. 2019, 25(23):7046-7057.
Parihar et al., "NK Cells Expressing a Chimeric Activating Receptor Eliminate MDSCs and Rescue Impaired CAR-T Cell Activity against Solid Tumors," Cancer Immunol. Research, Mar. 2019, 7(3):363-375.
Parikh, "Chronic lymphocytic leukemia treatment algorithm 2018," Blood Cancer J., Oct. 3, 2018, 8:93, 10 pages.
Park et al., "CD70 as a target for chimeric antigen receptor T cells in head and neck squamous cell carcinoma," Oral Oncology, Mar. 2018, 78:145-150.
PCT International Search Report and Written Opinion in International Appln. No. PCT/US2019/059260, dated Jan. 31, 2020, 11 pages.
Pemmaraju et al., "Tagraxofusp in Blastic Plasmacytoid Dendritic-Cell Neoplasm," N. Engl. J. Medicine, Apr. 25, 2019, 380(17):1628-1637.
Posey Jr. et al., "Distinguishing Truncated and Normal MUC1 Glycoform Targeting from Tn-MUC1-Specific CAR T Cells: Specificity Is the Key to Safety," Immunity, Nov. 15, 2016, 45(5):947-948.
Priceman et al., "Regional Delivery of Chimeric Antigen Receptor-Engineered T Cells Effectively Targets HER2+ Breast Cancer Metastasis to the Brain," Clin. Cancer Research, Jan. 2018, 24(1):95-105.
Raje et al., "Anti-BCMA CAR T-Cell Therapy bb2121 in Relapsed or Refractory Multiple Myeloma," N. Engl. J. Medicine, May 2, 2019, 380(18):1726-1737.
Rincon et al., "Signal transduction by MAP kinases in T lymphocytes," Oncogene, Apr. 30, 2001, 20(19):2490-2497.
Ruella et al., "Catch me if you can: Leukemia Escape after CD19-Directed T Cell Immunotherapies," Comput. Struct. Biotechnol. Journal, Sep. 28, 2016, 14:357-362.

(56) References Cited

OTHER PUBLICATIONS

Sakemura et al., "Axl-RTK Inhibition Modulates T Cell Functions and Synergizes with Chimeric Antigen Receptor T Cell Therapy in B Cell Malignancies," Biol. Blood Marrow Transplantation, Mar. 2019, 25(3S):S165.

Sandström et al., "A novel CD44v6 targeting antibody fragment with improved tumor-to-blood ratio," Int. J. Oncology, Feb. 1, 2012, 40(5):1525-1532.

Smith et al., "BCMA-Targeted CAR T-cell Therapy plus Radiotherapy for the Treatment of Refractory Myeloma Reveals Potential Synergy," Cancer Immunol. Research, Jul. 2019, 7(7):1047-1053.

Smith et al., "GPRC5D is a target for the immunotherapy of multiple myeloma with rationally designed CAR T cells," Sci. Transl. Medicine, Mar. 27, 2019, 11(485)eaau7746, 15 pages.

Socie et al., "Acute graft-versus-host disease: from the bench to the bedside," Blood, Nov. 12, 2009, 114(20):4327-4336.

Song et al., "Effective adoptive immunotherapy of triple-negative breast cancer by folate receptor-alpha redirected CAR T cells is influenced by surface antigen expression level," J. Hematol. Oncology, Jul. 20, 2016, 9(1):56, 12 pages.

Sun et al., "Safety and efficacy of targeting CD138 with a chimeric antigen receptor for the treatment of multiple myeloma," Oncotarget, Mar. 22, 2019, 10(24):2369-2383.

Tang et al., "In Vitro-expanded Antigen-specific Regulatory T Cells Suppress Autoimmune Diabetes," J. Exp. Medicine, Jun. 7, 2004, 199(11):1455-1465.

Thistlethwaite et al., "The clinical efficacy of first-generation carcinoembryonic antigen (CEACAM5)-specific CAR T cells is limited by poor persistence and transient pre-conditioning-dependent respiratory toxicity," Cancer Immunol. Immunotherapy, Jun. 28, 2017, 66(11):1425-1436.

Tsuchiya et al., "Differential expression of N-cadherin and E-cadherin in normal human tissues," Arch. Histol. Cytology, Jun. 2006, 69(2):135-145.

Wang et al., "Lenalidomide Enhances the Function of CS1 Chimeric Antigen Receptor-Redirected T Cells Against Multiple Myeloma," Clin. Cancer Research, Jan. 1, 2018, 24(1):106-119.

Wang et al., "Targeting Fibroblast Activation Protein in Tumor Stroma with Chimeric Antigen. Receptor T Cells Can Inhibit Tumor Growth and Augment Host Immunity without Severe Toxicity," Cancer Immunol. Research, Feb. 2014, 2(2):154-166.

Xu et al., "Exploratory trial of a biepitopic CAR T-targeting B cell maturation antigen in relapsed/refractory multiple myeloma," Proc. Natl, Acad. Sci. USA, May 7, 2019, 116(19):9543-9551.

Yalniz et al., "Safety and Efficacy of Infliximab Therapy in the Setting of Steroid-Refractory Acute Graft-versus-Host Disease," Biol. Blood Marrow Transplantation, Sep. 2017, 23(9):1478-1484.

Yamazaki et al., "Effective expansion of alloantigen-specific Foxp3+ CD25+ CD4+ regulatory T cells by dendritic cells during the mixed leukocyte reaction," Proc. Natl. Acad. Sci. USA, Feb. 21, 2006, 103(8):2758-2763.

Yang et al., "T cells expressing NKG2D chimeric antigen receptors efficiently eliminate glioblastoma and cancer stem cells," J. Immunother. Cancer, Jul. 9, 2019, 7(1):171, 13 pages.

Yoon et al., "FVIII-specific human chimeric antigen receptor T-regulatory cells suppress T- and B-cell responses to FVIII," Blood, Jan. 12, 2017, 129(2):238-245.

Yoshida et al., "All-trans retinoic acid enhances cytotoxic effect of T cells with an anti-CD38 chimeric antigen receptor in acute myeloid leukemia," Clin. Transl. Immunology, Dec. 9, 2016, 5(12):e116, 7 pages.

Zhang et al., "An Anti-CD103 Immunotoxin Promotes Long-Term Survival of Pancreatic Islet Allografts," Am. J. Transplantation, Aug. 20, 2009, 9(9):2012-2023.

Zhang et al., "Treatment of CD20-directed Chimeric Antigen Receptor-modified T cells in patients with relapsed or refractory B-cell non-Hodgkin lymphoma; an early phase IIa trial report," Signal Transduct. Target. Therapy, Mar. 11, 2016, 1:16002.

Zhao et al., "A phase 1, open-label study of LCAR-B38M, a chimeric antigen receptor T cell therapy directed against B cell maturation antigen, in patients with relapsed or refractory multiple myeloma," J. Hematol. Oncology, Dec. 20, 2018, 11(1):141, 8 pages.

Zhao et al., "In vivo-activated CD103+CD4+ regulatory T cells ameliorate ongoing chronic graft-versus-host disease," Blood, Sep. 1, 2008, 112(5):2129-2138.

CAR19(SEQ ID NO:1)

atggccttaccagtgaccgccttgctcctgccgctggccttgctgctccacgccgcca
ggccggacatccagatgacacagactacatcctccctgtctgcctctctgggagacag
agtcaccatcagttgcagggcaagtcaggacattagtaaatatttaaattggtatcag
cagaaaccagatggaactgttaaactcctgatctaccatacatcaagattacactcag
gagtcccatcaaggttcagtggcagtgggtctggaacagattattctctcaccattag
caacctggagcaagaagatattgccacttacttttgccaacagggtaatacgcttccg
tacacgttcggaggggggaccaagctggagatcacaggtggcggtggctcgggcggtg
gtgggtcgggtggcggcggatctgaggtgaaactgcaggagtcaggacctggcctggt
ggcgccctcacagagcctgtccgtcacatgcactgtctcaggggtctcattacccgac
tatggtgtaagctggattcgccagcctccacgaaagggtctggagtggctgggagtaa
tatggggtagtgaaaccacatactataattcagctctcaaatccagactgaccatcat
caaggacaactccaagagccaagttttcttaaaaatgaacagtctgcaaactgatgac
acagccatttactactgtgccaaacattattacggtggtagctatgctatggact
actggggccaaggaacctcagtcaccgtctcctcaaccacgacgccagcgccgcgacc
accaacaccggcgcccaccatcgcgtcgcagcccctgtcctgcgcccagaggcgtgc
cggccagcggcggggggcgcagtgcacacgaggggctggacttcgcctgtgatatct
acatctgggcgcccttggccgggacttgtggggtccttctcctgtcactggttatcac
cctttactgcaaacggggcagaaagaaactcctgtatatattcaaacaaccatttatg
agaccagtacaaactactcaagaggaagatggctgtagctgccgatttccagaagaag
aagaaggaggatgtgaactgagagtgaagttcagcaggagcgcagacgcccccgcgta
caagcagggccagaaccagctctataacgagctcaatctaggacgaagagaggagtac
gatgttttggacaagagacgtggccgggaccctgagatggggggaaagccgagaagga
agaaccctcaggaaggcctgtacaatgaactgcagaaagataagatggcggaggccta
cagtgagattgggatgaaaggcgagcgccggaggggcaaggggcacgatggcctttac
cagggtctcagtacagccaccaaggacacctacgacgccttcacatgcaggccctgc
cccctcgc

FIG. 2

CD3 directed Envelope(SEQ ID NO:2)

GAATTCGAGCTCGCCCCGTTACATAACTTACGGTAAATGGCCCGCCTGGCTGACCGCC
CAACGACCCCCGCCCATTGACGTCAATAATGACGTATGTTCCCATAGTAACGCCAATA
GGGACTTTCCATTGACGTCAATGGGTGGAGTATTTACGGTAAACTGCCCACTTGGCAG
TACATCAAGTGTATCATATGCCAAGTACGCCCCCTATTGACGTCAATGACGGTAAATG
GCCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAACAACTCC
GCCCCATTGACGCAAATGGGCGGTAGGCGTGTACGGTGGGAGGTCTATATAAGCAGAG
CTCGTTTAGTGAACCGTCAGATCGCCTGGAGACGCCATCCACGCTGTTTTGACCTCCA
TAGAAGACACCGGGACCGATCCAGCCTCCGGGGGATCGATCCCCCGATCCTGAGAAC
TTCAGGGTGAGTTTGGGGACCCTTGATTGTTCTTTCTTTTCGCTATTGTAAAATTCA
TGTTATATGGAGGGGGCAAAGTTTTCAGGGTGTTGTTTAGAATGGGAAGATGTCCCTT
GTATCACCATGGACCCTCATGATAATTTTGTTTCTTTCACTTTCTACTCTGTTGACAA
CCATTGTCTCCTCTTATTTTCTTTTCATTTTCTGTAACTTTTTCGTTAAACTTTAGCT
TGCATTTGTAACGAATTTTTAAATTCACTTTTGTTTATTTGTCAGATTGTAAGTACTT
TCTCTAATCACTTTTTTTTCAAGGCAATCAGGGTATATTATATTGTACTTCAGCACAG
TTTTAGAGAACAATTGTTATAATTAAATGATAAGGTAGAATATTTCTGCATATAAATT
CTGGCTGGCGTGGAAATATTCTTATTGGTAGAAACAACTACATCCTGGTCATCATCCT
GCCTTTCTCTTTATGGTTACAATGATATACACTGTTTGAGATGAGGATAAAATACTCT
GAGTCCAAACCGGGCCCCTCTGCTAACCATGTTCATGCCTTCTTCTTTTTCCTACAGC
TCCTGGGCAACGTGCTGGTTATTGTGCTGTCTCATCATTTTGGCAAAGAATTGTAATA
CGACTCACTATAGGGCGAATTCGGATCCCCGGTAGttaattaaaacttagggtgcaA
GAtcatccacaATGAGCCCCCAGAGAGACCGCATCAACGCATTCTACAAGGACAACCC
ACATAGCAAAGGGAGCCGCATCGTGATTAATCGAGAGCACCTGATGATCGATAGACCT
TACGTGCTGCTGGCTGTGCTGTTCGTCATGTTTCTGAGCCTGATTGGTCTGCTGGCAA
TCGCCGGCATTAGACTGCACCGCGCCGCTATCTATACAGCAGAGATTCATAAGTCCCT
GTCTACCAACCTGGACGTGACAAATTCCATCGAACATCAGGTGAAGGATGTCCTGACT
CCACTGTTCAAAATCATTGGTGACGAGGTCGGACTGCGAACTCCACAGCGGTTCACCG
ACCTGGTGAAGTTTATCAGCGATAAGATCAAGTTCCTGAACCCAGACCGGGAGTACGA
CTTTAGGGATCTGACCTGGTGCATCAACCCCCTGAACGGATCAAGCTGAACTACGAC
CAGTATTGTGCAGATGTCGCAGCCGAGGAACTGATGAACGCCCTGGTGAATTCCACAC

FIG. 3

CD3 directed Envelope(SEQ ID NO:2 - continued)

```
TGCTGGAGACTAGGACCACAAACCAGTTCCTGGCCGTGTCTAAGGGAAATTGCCCTGG
GCCAACTACCATCCGCGGCCAGTTTTCAAATATGAGTCTGTCACTGCTGGATCTGTAC
CTGAGCCGAGGATATAACGTGAGCTCCATTGTCACCATGACATCCCAGGGGATGTACG
GCGGAACCTATCTGGTGGGAAAGCCAGACCTGAATTCCAAAGGGTCTGAGCTGAGTCA
GCCTTCAATGTACCGAGTGTTCGAAGTGGGCGTCATCCGAAACCCAGGACTGGGAGCA
CCCGTGTTCCACATGACCAATTATTTTGAGCAGCCCATTAGCAAGGATCTGTCCAACT
GTATGGTGGCCCTGGGTGAACTGAAACTGGCTGCACTGTGCCATAGGGCGACAGTAT
CACAATTCCCTGTAGAGGGTCCGGCAAGGGCGTGTCTTTTCAGCTGGTGAAGCTGGGC
GTCTGGAAAAGCCCTACTGATATGCACAGTTGGGTCCCACTGTCAACCGACGATCCCG
TGATCGATAGACTGTACCTGTCTAGTCATCGCGGAGTCATTACCGACAACCAGGCTAA
TTGGGCAGTGCCTACAACTAGAACCGACGATAAGCTGCAGAAAGAGACATGCTTCCAG
CAGGCCTGTAAGGGGAAAATCCAGGCTCTGtGcGAGAATCTGGAATGGGCTCCTCTGA
AGGATTCTCGCATTCCAAGTTATGGAGTGCTGTCAGTCAACCTGAGCCTGGCCGCTGA
ACCCAAGATCAAAATTGCCTCTGGATTTGGGCCTCTGATCACTCACGGTAGCGGCATG
GACCTGTACAAGTCCAACCATAACAACGTGTACTGGCTGACTATTCCACCCATGAAAA
ACCTGGCTCTGGGCGTGATCAATACCCTGAAGTGGATTCCTCGCCTGAAGGTCAGCCC
ATACCTGTTTACAGTGCCCATCGAGGAAGCCGACGAGGATTGTCGGGCTCCAACATAC
CTGCCCGCAGAAGTGACTGGCGACGTGAAACTGTCAAGCAACCTGGTCATCCTGCCAG
GACAGGACCTGCAGTACGTGCTGGCTACTTATGATACCTCTGGAGTCGAACATGCAGT
GGTCTACTACGTGTACAGCCCTGGCGGGTCTTTCAGTTACGTGTATCCTTTTCGGCTG
CCAATCAAGGGTACACCAATTGAGCTGCAGGTGGAATGCTTCACTTGGGCCCAGAGGC
TGTGGTGCAGACACTTTTGCGTGCTGGCTGATTCAGAGAGCGGGGGTCACCTGACCCA
TTCTGGAATGGTGGGGATGGAAGTCAGTTGTACAGTGAACAGGGAGGACGAAGCCAAT
ATCGAGGGAAGGGCGGCCCAGCCGGCCCAGGTGCAGCTGCAGCAGAGCGGCGCCGAGC
TGGCCAGGCCCGGCGCCAGCGTGAAGATGAGCTGCAAGGCCAGCGGCTACACCTTCAC
CAGGTACACCATGCACTGGGTGAAGCAGAGGCCCGGCCAGGGCCTGGAGTGGATCGGC
TACATCAACCCCAGCAGGGGCTACACCAACTACAACCAGAAGTTCAAGGACAAGGCCA
CCCTGACCACCGACAAGAGCAGCAGCACCGCCTACATGCAGCTGAGCAGCCTGACCAG
CGAGGACAGCGCCGTGTACTACTGCGCCAGGTACTACGACGACCACTACTGCCTGGAC
TACTGGGGCCAGGGCACCACCCTGACCGTGAGCAGCGCCGGCGGCGGCGGCAGCGGCG
GCGGCGGCAGCGGCGGCGGCGGCAGCCAGATCGTGCTGACCCAGAGCCCCGCCATCAT
GAGCGCCAGCCCCGGCGAGAAGGTGACCATGACCTGCAGCGCCAGCAGCAGCGTGAGC
```

FIG. 3 (continued)

CD3 directed Envelope(SEQ ID NO:2 - continued)

TACATGAACTGGTACCAGCAGAAGAGCGGCACCAGCCCCAAGAGGTGGATCTACGACA
CCAGCAAGCTGGCCAGCGGCGTGCCCGCCCACTTCAGGGGCAGCGGCAGCGGCACCAG
CTACAGCCTGACCATCAGCGGCATGGAGGCCGAGGACGCCGCCACCTACTACTGCCAG
CAGTGGAGCAGCAACCCCTTCACCTTCGGCAGCGGCACCAAGCTGGAGATCAACAGGG
CCGACACCGCCCCCACCgcgGCCGCAAGAGGATCGCATCACCATCACCATCACTGATA
GTTTGTACTAGTGTGAAATAGACATCAGAATTAAGAAAAACGTAGGGTCCAAGTGGTT
CCCCGTTATGGACTCGCTATCTGTCAACCAGATCTTATACCCTGAAGTTCACCTAGAT
AGCCCGATAGTTACCAATAAGATAGTAGCCATCCTGGAGTATGCTCGACTGTTTAAAC
CTGCAGGCATGCAAGCTGATCTTTTTCCCTCTGCCAAAAATTATGGGGACATCATGAA
GCCCCTTGAGCATCTGACTTCTGGCTAATAAAGGAAATTTATTTTCATTGCAATAGTG
TGTTGGAATTTTTTGTGTCTCTCACTCGGAAGGACATATGGGAGGGCAAATCATTTAA
AACATCAGAATGAGTATTTGGTTTAGAGTTTGGCAACATATGCCCATATGCTGGCTGC
CATGAACAAAGGTTGGCTATAAAGAGGTCATCAGTATATGAAACAGCCCCTGCTGTC
CATTCCTTATTCCATAGAAAAGCCTTGACTTGAGGTTAGATTTTTTTATATTTTGTT
TTGTGTTATTTTTTCTTTAACATCCCTAAAATTTTCCTTACATGTTTTACTAGCCAG
ATTTTTCCTCCTCTCCTGACTACTCCCAGTCATAGCTGTCCCTCTTCTCTTATGGAGA
TCCCTCGAGGAGCTTTTTGCAAAAGCCTAGGCCTCCAAAAAAGCCTCTTCACTACTTC
TGGAATAGCTCAGAGGCCGCGGCCTCGGCCTCTGCATAAATAAAAAAAATTAGTCAGC
CATGGGGCGGAGAATGGGCGGAACTGGGCGGAGTTAGGGGCGGGATGGGCGGAGTTAG
GGGCGGGACTATGGTTGCTGACTAATTGCTGCATTAATGAATCGGCCAACGCGCGGGG
AGAGGCGGTTTGCGTATTGGGCGCTCTTCCGCTTCCTCGCTCACTGACTCGCTGCGCT
CGGTCGTTCGGCTGCGGCGAGCGGTATCAGCTCACTCAAAGGCGGTAATACGGTTATC
CACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTA
CACTAGAAGAACAGTATTTGGTATCTGCGCTCTGCTGAAGCCAGTTACCTTCGGAAAA

FIG. 3 (continued)

CD3 directed Envelope(SEQ ID NO:2 - continued)

```
AGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATG
AGATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCA
TTGCTACAGGCATCGTGGTGTCACGCTCGTCGTTTGGTATGGCTTCATTCAGCTCCGG
TTCCCAACGATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATCACTCATGG
TTATGGCAGCACTGCATAATTCTCTTACTGTCATGCCATCCGTAAGATGCTTTTCTGT
GACTGGTGAGTACTCAACCAAGTCATTCTGAGAATAGTGTATGCGGCGACCGAGTTGC
TCTTGCCCGGCGTCAATACGGGATAATACCGCGCCACATAGCAGAACTTTAAAAGTGC
TCATCATTGGAAAACGTTCTTCGGGGCGAAAACTCTCAAGGATCTTACCGCTGTTGAG
ATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAA
GGGCGACACGGAAATGTTGAATACTCATACTCTTCCTTTTTCAATATTATTGAAGCAT
TTATCAGGGTTATTGTCTCATGAGCGGATACATATTTGAATGTATTTAGAAAAATAAA
CAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTCTCGC
GCGTTTCGGTGATGACGGTGAAAACCTCTGACACATGCAGCTCCCGGAGACGGTCACA
GCTTGTCTGTAAGCGGATGCCGGGAGCAGACAAGCCCGTCAGGGCGCGTCAGCGGGTG
TTGGCGGGTGTCGGGCTGGCTTAACTATGCGGCATCAGAGCAGATTGTACTGAGAGT
GCACCATTCGACGCTCTCCCTTATGCGACTCCTGCATTAGGAAGCAGCCCAGTAGTAG
GTTGAGGCCGTTGAGCACCGCCGCCGCAAGGAATGGTCTGGCTTATCGAAATTAATAC
GACTCACTATAGGGAGACCG
```

FIG. 3 (continued)

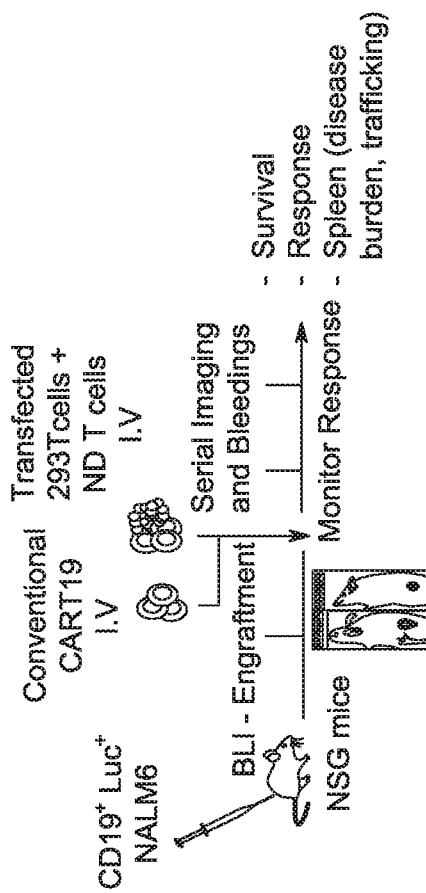
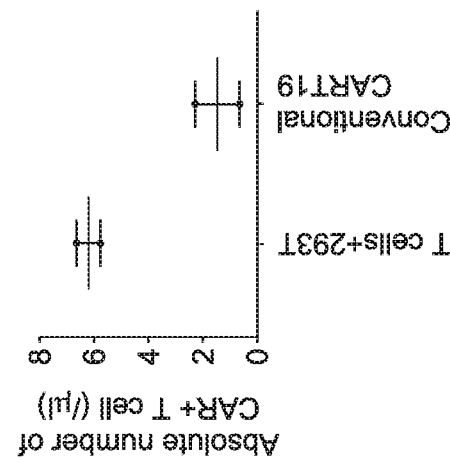
FIG. 5A
FIG. 5C
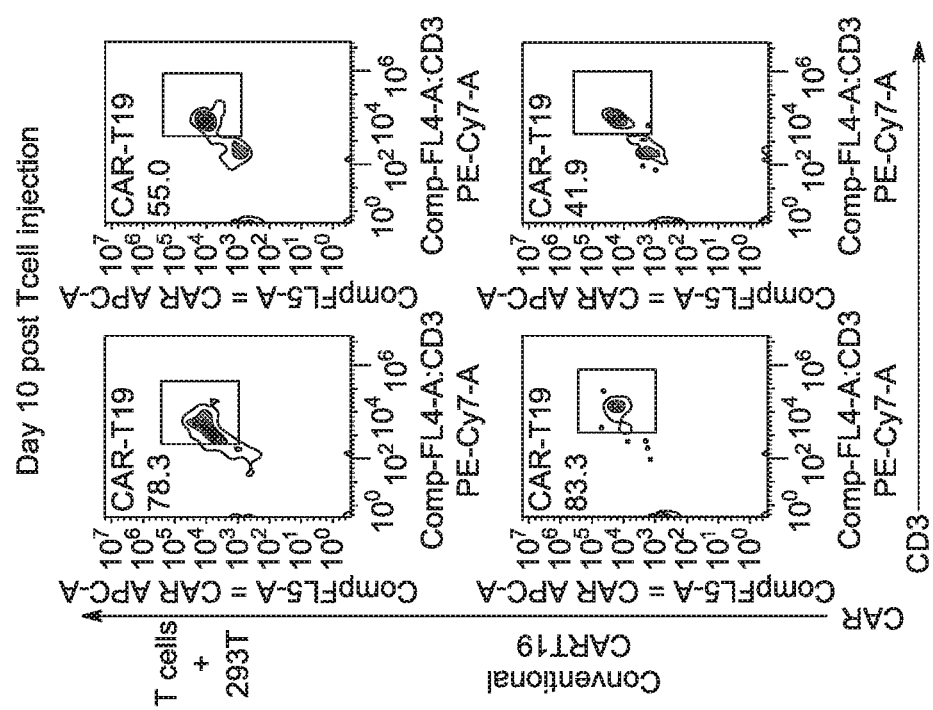
FIG. 5B

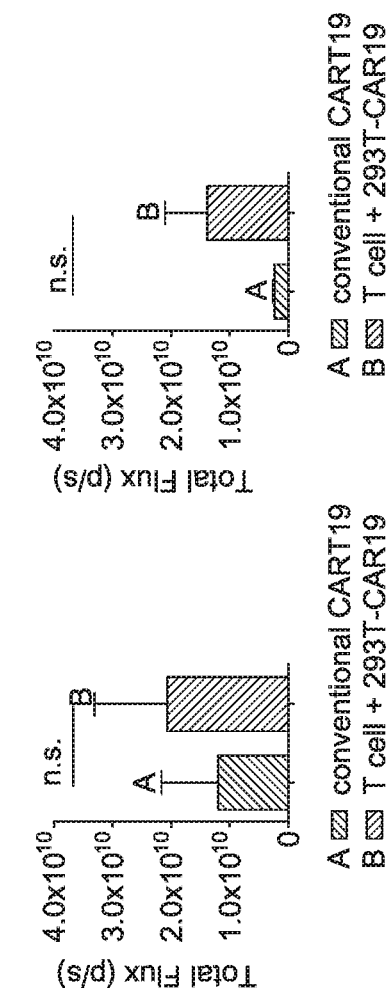
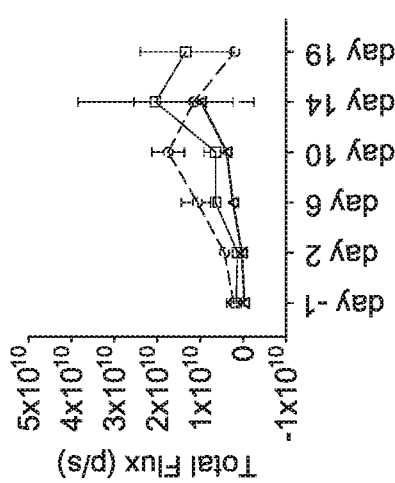
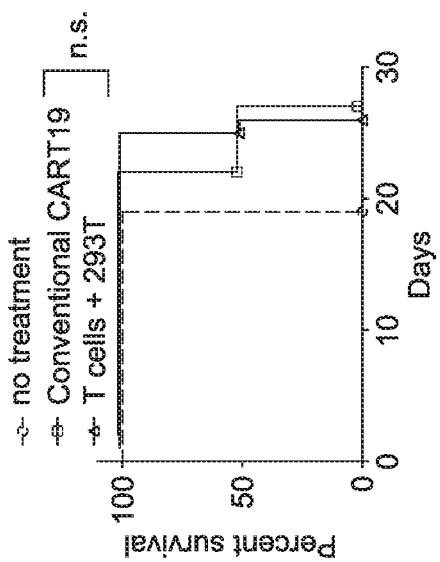

SEQUENCE LISTING

```
<160> NUMBER OF SEQ ID NOS: 2

<210> SEQ ID NO 1
<211> LENGTH: 1458
<212> TYPE: DNA
<213> ORGANISM: artificial
<220> FEATURE:
<223> OTHER INFORMATION: nucleic acid sequence encoding a chimeric
      antigen receptor targeting a CD19 antigen

<400> SEQUENCE: 1
atggccttac cagtgaccgc cttgctcctg ccgctggcct tgctgctcca cgccgccagg      60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360
ggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcaggggtc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cgggggggcgc agtgcacacg    900 aggggggctgg acttcgcctg tgatatctac atctgggcgc ccttggccgg gacttgtggg    960
gtccttctcc tgtcactggt tatcacccctt tactgcaaac ggggcagaaa gaaactcctg   1020
```

```
tatatattca aacaaccatt tatgagacca gtacaaacta ctcaagagga agatggctgt    1080
agctgccgat ttccagaaga agaagaagga ggatgtgaac tgagagtgaa gttcagcagg    1140
agcgcagacg cccccgcgta caagcagggc cagaaccagc tctataacga gctcaatcta    1200
ggacgaagag aggagtacga tgttttggac aagagacgtg gccggacccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgc                                                  1458

<210> SEQ ID NO 2
<211> LENGTH: 7212
<212> TYPE: DNA
<213> ORGANISM: artificial
<220> FEATURE:
<223> OTHER INFORMATION: nucleic acid sequence encoding a modified viral
      envelope polypeptide capable of targeting a CD3 antigen

<400> SEQUENCE: 2
gaattcgagc tcgcccccgtt acataactta cggtaaatgg cccgcctggc tgaccgccca      60
acgacccccg cccattgacg tcaataatga cgtatgttcc catagtaacg ccaatagggca    120 ctttccattg acgtcaatgg gtggagtatt tacggtaaac tgcccacttg gcagtacatc     180
aagtgtatca tatgccaagt acgcccccta ttgacgtcaa tgacggtaaa tggcccgcct     240
ggcattatgc ccagtacatg accttatggg actttcctac ttggcagtac atctacgtat     300
tagtcatcgc tattaccatg gtgatgcggt tttggcagta catcaatggg cgtggatagc     360
ggtttgactc acggggattt ccaagtctcc accccattga cgtcaatggg agtttgtttt     420
ggcaccaaaa tcaacgggac tttccaaaat gtcgtaacaa ctccgcccca ttgacgcaaa     480
tgggcggtag gcgtgtacgg tgggaggtct atataagcag agctcgttta gtgaaccgtc     540
agatcgcctg gagacgccat ccacgctgtt ttgacctcca tagaagacac cgggaccgat     600
ccagcctccg gggatcgat cccccgatc ctgagaactt cagggtgagt ttggggaccc      660
ttgattgttc tttctttttc gctattgtaa aattcatgtt atatggaggg ggcaaagttt     720
tcagggtgtt gtttagaatg ggaagatgtc ccttgtatca ccatggaccc tcatgataat     780
tttgtttctt tcactttcta ctctgttgac aaccattgtc cctcttatt ttcttttcat      840 tttctgtaac tttttcgtta aactttagct tgcatttgta acgaattttt aaattcactt     900
ttgtttattt gtcagattgt aagtactttc tctaatcact tttttttcaa ggcaatcagg     960
gtatattata ttgtacttca gcacagtttt agagaacaat tgttataatt aaatgataag    1020
gtagaatatt tctgcatata aattctggct ggcgtggaaa tattcttatt ggtagaaaca    1080
actacatcct ggtcatcatc ctgcctttct ctttatggtt acaatgatat acactgtttg    1140
agatgaggat aaaatactct gagtccaaac cgggcccctc tgctaaccat gttcatgcct    1200
tcttcttttt cctacagctc ctgggcaacg tgctggttat tgtgctgtct catcattttg    1260
gcaaagaatt gtaatacgac tcactatagg gcgaattcgg atccccggt agttaattaa     1320 aacttagggt gcaagatcat ccacaatgag cccccagaga gaccgcatca acgcattcta    1380
caaggacaac ccacatagca agggagccg catcgtgatt aatcgagagc acctgatgat    1440
cgatagacct tacgtgctgc tggctgtgct gttcgtcatg tttctgagcc tgattggtct    1500
gctggcaatc gccggcatta gactgcaccg cgccgctatc tatacagcag agattcataa    1560
```

-continued

```
gtccctgtct accaacctgg acgtgacaaa ttccatcgaa catcaggtga aggatgtcct    1620
gactccactg ttcaaaatca ttggtgacga ggtcggactg cgaactccac agcggttcac    1680
cgacctggtg aagtttatca gcgataagat caagttcctg aacccagacc gggagtacga    1740
ctttagggat ctgacctggt gcatcaaccc ccctgaacgg atcaagctga actacgacca    1800
gtattgtgca gatgtcgcag ccgaggaact gatgaacgcc ctggtgaatt ccacactgct    1860
ggagactagg accacaaacc agttcctggc cgtgtctaag ggaaattgcc ctgggccaac    1920
taccatccgc ggccagtttt caaatatgag tctgtcactg ctggatctgt acctgagccg    1980
aggatataac gtgagctcca ttgtcaccat gacatcccag gggatgtacg gcggaaccta    2040
tctggtggga aagccagacc tgaattccaa agggtctgag ctgagtcagc cttcaatgta    2100
ccgagtgttc gaagtgggcg tcatccgaaa cccaggactg ggagcacccg tgttccacat    2160
gaccaattat tttgagcagc ccattagcaa ggatctgtcc aactgtatgg tggccctggg    2220
tgaactgaaa ctggctgcac tgtgccatag gggcgacagt atcacaattc cctgtagagg    2280
gtccggcaag ggcgtgtctt ttcagctggt gaagctgggc gtctggaaaa gcctactgga    2340
tatgcacagt tgggtcccac tgtcaaccga cgatcccgtg atcgatagac tgtacctgtc    2400
tagtcatcgc ggagtcatta ccgacaacca ggctaattgg gcagtgccta caactagaac    2460
cgacgtaaag ctgcagaaag agacatgctt ccagcaggcc tgtaagggga aaatccaggc    2520
tctgtgcgag aatctggaat gggctcctct gaaggattct cgcattccaa gttatggagt    2580
gctgtcagtc aacctgagcc tggccgctga acccaagatc aaaattgcct ctggatttgg    2640
gcctctgatc actcacggta gcggcatgga cctgtacaag tccaaccata caacgtgta    2700
ctggctgact attccaccca tgaaaaacct ggctctgggc gtgatcaata ccctgaagtg    2760
gattcctcgc ctgaaggtca gcccatacct gtttacagtg cccatcgagg aagccgacga    2820
ggattgtcgg gctccaacat acctgcccgc agaagtgact ggcgacgtga aactgtcaag    2880
caacctggtc atcctgccag acaggacct gcagtacgtg ctggctactt atgatacctc    2940
tggagtcgaa catgcagtgg tctactacgt gtacagccct ggcgggtctt tcagttacgt    3000
gtatccttttt cggctgccaa tcaagggtac accaattgag ctgcaggtgg aatgcttcac    3060
ttgggcccag aggctgtggt gcagacactt ttgcgtgctg gctgattcag agagcggggg    3120
tcacctgacc cattctggaa tggtggggat ggaagtcagt tgtacagtga acagggagga    3180
cgaagccaat atcgagggaa gggcggccca gccggcccag gtgcagctgc agcagagcgg    3240
cgccgagctg gccaggcccg gcgccagcgt gaagatgagc tgcaaggcca gcggctacac    3300
cttcaccagg tacaccatgc actgggtgaa gcagaggccc ggccagggcc tggagtggat    3360
cggctacatc aaccccagca ggggctacac caactacaac cagaagttca aggacaaggc    3420
caccctgacc accgacaaga gcagcagcac cgcctacatg cagctgagca gcctgaccag    3480
cgaggacagc gccgtgtact actgcgccag gtactacgac gaccactact gcctggacta    3540
ctggggccag ggcaccaccc tgaccgtgag cagcgccggc ggcggcggca gcggcggcgg    3600
cggcagcggc ggcggcggca gccagatcgt gctgacccag agccccgcca tcatgagcgc    3660
cagcccccggc gagaaggtga ccatgacctg cagcgccagc agcagcgtga gctacatgaa    3720
ctggtaccag cagaagagcg gcaccagccc caagaggtgg atctacgaca ccagcaagct    3780
ggccagcggc gtgcccgccc acttcagggg cagcggcagc ggcaccagct acagcctgac    3840
catcagcggc atggaggccg aggacgccgc cacctactac tgccagcagt ggagcagcaa    3900
ccccttcacc ttcggcagcg gcaccaagct ggagatcaac agggccgaca ccgcccccac    3960
```

```
cgcggccgca agaggatcgc atcaccatca ccatcactga tagtttgtac tagtgtgaaa      4020
tagacatcag aattaagaaa aacgtagggt ccaagtggtt ccccgttatg gactcgctat      4080
ctgtcaacca gatcttatac cctgaagttc acctagatag cccgatagtt accaataaga      4140
tagtagccat cctggagtat gctcgactgt ttaaacctgc aggcatgcaa gctgatcttt      4200
ttccctctgc caaaaattat ggggacatca tgaagcccct tgagcatctg acttctggct      4260
aataaaggaa atttattttc attgcaatag tgtgttggaa ttttttgtgt ctctcactcg      4320
gaaggacata tgggagggca aatcatttaa aacatcagaa tgagtatttg gtttagagtt      4380
tggcaacata tgcccatatg ctggctgcca tgaacaaagg ttggctataa agaggtcatc      4440
agtatatgaa acagcccct gctgtccatt ccttattcca tagaaaagcc ttgacttgag       4500
gttagatttt ttttatattt tgttttgtgt tattttttc tttaacatcc ctaaaatttt       4560
ccttacatgt tttactagcc agattttcc tcctctcctg actactccca gtcatagctg       4620
tccctcttct cttatggaga tccctcgagg agcttttgc aaaagcctag gcctccaaaa       4680
aagcctcttc actacttctg gaatagctca gaggccgcgg cctcggcctc tgcataaata      4740
aaaaaaatta gtcagccatg gggcggagaa tgggcggaac tgggcggagt taggggcggg      4800
atgggcggag ttaggggcgg gactatggtt gctgactaat tgctgcatta atgaatcggc      4860
caacgcgcgg ggagaggcgg tttgcgtatt gggcgctctt ccgcttcctc gctcactgac      4920
tcgctgcgct cggtcgttcg gctgcggcga gcggtatcag ctcactcaaa ggcggtaata      4980
cggttatcca cagaatcagg ggataacgca ggaaagaaca tgtgagcaaa aggccagcaa      5040
aaggccagga accgtaaaaa ggccgcgttg ctggcgtttt tccataggct ccgcccccct      5100
gacgagcatc acaaaaatcg acgctcaagt cagaggtggc gaaacccgac aggactataa      5160
agataccagg cgtttccccc tggaagctcc ctcgtgcgct ctcctgttcc gaccctgccg      5220
cttaccggat acctgtccgc ctttctccct tcgggaagcg tggcgctttc tcatagctca      5280
cgctgtaggt atctcagttc ggtgtaggtc gttcgctcca agctgggctg tgtgcacgaa      5340
ccccccgttc agcccgaccg ctgcgcctta tccggtaact atcgtcttga gtccaacccg      5400
gtaagacacg acttatcgcc actggcagca gccactggta acaggattag cagagcgagg      5460
tatgtaggcg gtgctacaga gttcttgaag tggtggccta actacggcta cactagaaga      5520
acagtatttg gtatctgcgc tctgctgaag ccagttacct tcggaaaaag agttggtagc      5580
tcttgatccg gcaaacaaac caccgctggt agcggtggtt tttttgtttg caagcagcag      5640
attacgcgca gaaaaaaagg atctcaagaa gatcctttga tcttttctac ggggtctgac      5700
gctcagtgga acgaaaactc acgttaaggg attttggtca tgagattatc aaaaaggatc      5760
ttcacctaga tccttttaaa ttaaaaatga agttttaaat caatctaaag tatatatgag      5820
taaacttggt ctgacagtta ccaatgctta atcagtgagg cacctatctc agcgatctgt      5880
ctatttcgtt catccatagt tgcctgactc ccgtcgtgt agataactac gatacgggag       5940
ggcttaccat ctggccccag tgctgcaatg ataccgcgag acccacgctc accggctcca      6000
gatttatcag caataaacca gccagccgga agggccgagc gcagaagtgg tcctgcaact      6060
ttatccgcct ccatccagtc tattaattgt tgccgggaag ctagagtaag tagttcgcca      6120
gttaatagtt tgcgcaacgt tgttgccatt gctacaggca tcgtggtgtc acgctcgtcg      6180
tttggtatgg cttcattcag ctccggttcc caacgatcaa ggcgagttac atgatccccc      6240
atgttgtgca aaaaagcggt tagctccttc ggtcctccga tcgttgtcag aagtaagttg      6300
```

```
gccgcagtgt tatcactcat ggttatggca gcactgcata attctcttac tgtcatgcca    6360
tccgtaagat gcttttctgt gactggtgag tactcaacca agtcattctg agaatagtgt    6420
atgcggcgac cgagttgctc ttgcccggcg tcaatacggg ataataccgc gccacatagc    6480
agaactttaa aagtgctcat cattggaaaa cgttcttcgg ggcgaaaact ctcaaggatc    6540
ttaccgctgt tgagatccag ttcgatgtaa cccactcgtg cacccaactg atcttcagca    6600
tcttttactt tcaccagcgt ttctgggtga gcaaaaacag gaaggcaaaa tgccgcaaaa    6660
aagggaataa gggcgacacg gaaatgttga atactcatac tcttcctttt tcaatattat    6720
tgaagcattt atcagggtta ttgtctcatg agcggataca tatttgaatg tatttagaaa    6780
aataaacaaa tagggggttcc gcgcacattt ccccgaaaag tgccacctga cgtctaagaa    6840
accattatta tcatgacatt aacctataaa aataggcgta tcacgaggcc ctttcgtctc    6900
gcgcgtttcg gtgatgacgg tgaaaacctc tgacacatgc agctcccgga gacggtcaca    6960
gcttgtctgt aagcggatgc cgggagcaga caagcccgtc agggcgcgtc agcgggtgtt    7020
ggcgggtgtc ggggctggct taactatgcg gcatcagagc agattgtact gagagtgcac    7080
cattcgacgc tctcccttat gcgactcctg cattaggaag cagcccagta gtaggttgag    7140
gccgttgagc accgccgccg caaggaatgg tctggcttat cgaaattaat acgactcact    7200
atagggagac cg                                                        7212
```

METHODS AND MATERIALS FOR TREATING CANCER

CROSS-REFERENCE TO RELATED APPLICATIONS

This application is a National Stage application under 35 U.S.C. § 371 of International Application No. PCT/US2019/059260, having an International Filing Date of Oct. 31, 2019, which claims priority to U.S. Application Ser. No. 62/753,732, filed on Oct. 31, 2018. The disclosure of the prior application is considered part of the disclosure of this application, and is incorporated in its entirety into this application.

BACKGROUND

1. Technical Field

This document relates to methods and materials for generating T cells expressing an antigen receptor (e.g., a chimeric antigen receptor) in vivo. For example, viral particles including nucleic acid encoding an antigen receptor can be administered to a mammal to generate T cells expressing that antigen receptor within the mammal. In some cases, in vivo generation of T cells expressing a selected antigen receptor can be used to target cells (e.g., cancer cells) presenting an antigen (e.g., a tumor antigen) recognized by that selected antigen receptor.

2. Background Information

Chimeric antigen receptor T (CART) cell therapy is a revolutionary therapy in the treatment of cancer. In B cell malignancies, CD19 directed CART cell therapy resulted in unprecedented responses that led to FDA approval of two products in 2017. However, CART cell therapies are limited by complexity, high costs, the requirement for elaborate protocols that can only be applied in specialized good manufacturing practices (GMP) grade facilities, the highly individualized process, and the lead-time required for CART cell manufacturing. For example, in CART cell therapy, patients undergo apheresis, and T cells are isolated, stimulated, transduced, and expanded ex vivo for a period of 7-10 days to generate CART cells. Then patients receive lympho-depleting chemotherapy followed by infusion of the generated CART cells. Further, the activity of CART cell therapy in solid tumors is limited.

SUMMARY

This document provides methods and materials for generating T cells expressing a selected antigen receptor (e.g., a chimeric antigen receptor) in vivo.

In some cases, one or more viral particles containing nucleic acid encoding a selected antigen receptor can be administered to a mammal to generate T cells expressing that selected antigen receptor within the mammal. For example, one or more viral particles containing nucleic acid encoding a chimeric antigen receptor (CAR) administered to a mammal can transduce one or more T cells within the mammal (e.g., to introduce the nucleic acid encoding the selected antigen receptor into the T cells such that the T cells express the CAR) to generate one or more CART cells within the mammal.

In some cases, one or more cells capable of producing one or more viral particles containing nucleic acid encoding a selected antigen receptor (also referred to as virus-producing cells) can be administered to a mammal to generate T cells expressing that selected antigen receptor within the mammal. For example, one or more cells capable of producing viral particles containing nucleic acid encoding a CAR administered to a mammal can result in the production of infectious viral particles, which in turn can transduce one or more T cells within the mammal (e.g., to introduce the nucleic acid encoding the selected antigen receptor into the T cells such that the T cells express the CAR) to generate one or more CART cells within the mammal.

In some cases, in vivo generation of one or more T cells expressing a selected antigen receptor can be used to target cells (e.g., cancer cells) presenting an antigen (e.g., a tumor antigen) recognized by the selected antigen receptor. As described herein, one or more viral particles containing nucleic acid encoding a CAR (or one or more cells capable of producing such viral particles) can be administered to a mammal having cancer (e.g., a cancer presenting a tumor antigen) to generate one or more CART cells that can target cancer cells within the mammal. In some cases, the methods and materials described herein can be used for in vivo generation of tumor specific cytotoxic T cells (CTLs).

The ability to generate tumor-specific CARTs in vivo provides a unique opportunity to bypass ex vivo CART cell production, the most time consuming, labor intensive, and costly portion of CART cell manufacturing. The ability to generate tumor-specific CARTs in vivo also provides a unique opportunity to generate CART cells capable of targeting (e.g., locating and destroying) cancer cells, including cancer cells in solid tumors (that are typically undetectable by the immune system) and cancer cells at secondary (e.g., metastatic) locations. In addition, CART cells generated in vivo as described herein (e.g., by administering one or more viral particles containing nucleic acid encoding a selected antigen receptor or by administering one or more cells capable of producing such viral particles) can be more effective than ex vivo expanded and transduced T cells because a T cell generated in vivo as described herein can be naturally activated and differentiated in the tumor (or in the region of the tumor) and/or lymph nodes. Further, the methods and materials described herein can be more conducible to "off the shelf" reagents, thereby allowing individualized therapies (e.g., in the form of tumor-specific immune responses) to be quickly and readily applied to wide patient populations while limiting costs.

In general, one aspect of this document features a method for generating T cells expressing a selected antigen receptor in vivo within a mammal. The method comprises, or consists essentially of, administering a viral particle to the mammal. The viral particle comprises, or consists essentially of, (a) nucleic acid encoding the selected antigen receptor and (b) an exogenous molecule that targets the viral particle to infect T cells within the mammal, wherein the viral particle infects T cells comprising an endogenous T cell receptor within the mammal to form infected T cells, and wherein the infected T cells express the selected antigen receptor and the endogenous T cell receptor. The mammal can be a human. The viral particle can be a lentiviral particle. The antigen receptor can be a chimeric antigen receptor. The viral particle can target one or more cancer cells. The one or more cancer cells can express a tumor-specific antigen. The selected antigen receptor can target the tumor-specific antigen. The tumor-specific antigen can be CD19. The tumor-specific antigen can be CD19, and the antigen receptor targeting the tumor-specific antigen can be a CAR targeting CD19. The nucleic acid encoding the CAR targeting CD19 can comprise a nucleic acid sequence set forth in SEQ ID NO:1. The exogenous molecule can comprise an antigen-binding domain that can recognize CD3, and the viral particle can further comprise nucleic acid encoding the antigen-binding domain that can recognize CD3. The antigen-binding domain can be a single-chain variable fragment. The nucleic acid encoding the single-chain variable fragment that can recognize CD3 can comprise a nucleic acid sequence set forth in SEQ ID NO:2. The administration can be intravenous injection or intratumoral injection.

In another aspect, this document features a method for generating T cells expressing a selected antigen receptor in vivo within a mammal. The method comprises, or consists essentially of, administering, to the mammal, a cell capable of producing a viral particle, wherein the viral particle comprises, or consists essentially of, (a) nucleic acid encoding the selected antigen receptor, and (b) an exogenous molecule that targets the viral particle to infect T cells within the mammal, wherein the viral particle is produced within the mammal and infects T cells comprising an endogenous T cell receptor within the mammal to form infected T cells, and wherein the infected T cells express the selected antigen receptor and the endogenous T cell receptor. The mammal can be a human. The viral particle can be a lentiviral particle. The antigen receptor can be a chimeric antigen receptor. The viral particle can target one or more cancer cells. The one or more cancer cells can express a tumor-specific antigen. The selected antigen receptor can target the tumor-specific antigen. The tumor-specific antigen can be CD19. The tumor-specific antigen can be CD19, and the antigen receptor targeting the tumor-specific antigen can be a CAR targeting CD19. The nucleic acid encoding the CAR targeting CD19 can comprise a nucleic acid sequence set forth in SEQ ID NO:1. The exogenous molecule can comprise an antigen-binding domain that can recognize CD3, and the viral particle can further comprise nucleic acid encoding the antigen-binding domain that can recognize CD3. The antigen-binding domain can be a single-chain variable fragment. The nucleic acid encoding the single-chain variable fragment that can recognize CD3 can comprise a nucleic acid sequence set forth in SEQ ID NO:2. The administration can be intravenous injection or intratumoral injection.

In another aspect, this document features a method for treating a mammal having cancer comprising cancer cells presenting a selected antigen. The method comprises, or consists essentially of, administering a viral particle to the mammal, wherein the viral particle comprises, or consists essentially of, (a) nucleic acid encoding an antigen receptor targeting the selected antigen, and (b) an exogenous molecule that targets the viral particle to infect T cells within the mammal, wherein the administration is effective to generate T cells expressing the antigen receptor in vivo. The mammal can be a human. The viral particle can be a lentiviral particle. The cancer can be a B cell cancer. The antigen receptor can be a chimeric antigen receptor. The cancer can comprise cancer cells expressing a tumor-specific antigen. The antigen receptor can target the tumor-specific antigen. The tumor-specific antigen can be CD19. The tumor-specific antigen can be CD19, and the antigen receptor targeting the tumor-specific antigen can be a CAR targeting CD19. The nucleic acid encoding the CAR targeting CD19 can comprise a nucleic acid sequence set forth in SEQ ID NO:1. The exogenous molecule can comprise an antigen-binding domain that can recognize CD3, and the viral particle further can comprise nucleic acid encoding the antigen-binding domain that can recognize CD3. The antigen-binding domain can be a single-chain variable fragment. The nucleic acid encoding the single-chain variable fragment that can recognize CD3 can comprise a nucleic acid sequence set forth in SEQ ID NO:2. The administration can be intratumoral injection.

In another aspect, this document features a method for treating a mammal having cancer comprising cancer cells presenting a selected antigen. The method comprises, or consists essentially of, administering a cell producing a viral particle to the mammal, wherein the viral particle comprises, or consists essentially of, (a) nucleic acid encoding an antigen receptor targeting the selected antigen, and (b) an exogenous molecule that targets the viral particle to infect T cells within the mammal, wherein the administration is effective to generate T cells expressing the antigen receptor in vivo. The mammal can be a human. The viral particle can be a lentiviral particle. The cancer can be a B cell cancer. The antigen receptor can be a chimeric antigen receptor. The cancer can comprise cancer cells expressing a tumor-specific antigen. The antigen receptor can target the tumor-specific antigen. The tumor-specific antigen can be CD19. The tumor-specific antigen can be CD19, and the antigen receptor targeting the tumor-specific antigen can be a CAR targeting CD19. The nucleic acid encoding the CAR targeting CD19 can comprise a nucleic acid sequence set forth in SEQ ID NO:1. The exogenous molecule can comprise an antigen-binding domain that can recognize CD3, and the viral particle further can comprise nucleic acid encoding the antigen-binding domain that can recognize CD3. The antigen-binding domain can be a single-chain variable fragment. The nucleic acid encoding the single-chain variable fragment that can recognize CD3 can comprise a nucleic acid sequence set forth in SEQ ID NO:2. The administration can be intratumoral injection.

In another aspect, this document features a method for generating T cells expressing a selected antigen receptor in vivo within a mammal. The method comprises (or consists essentially of or consists of) administering, to the mammal, a cell capable of producing a viral particle, wherein the viral particle comprises nucleic acid encoding the selected antigen receptor, wherein the viral particle is produced within the mammal and infects T cells comprising an endogenous T cell receptor within the mammal to form infected T cells, and wherein the infected T cells express the selected antigen receptor and the endogenous T cell receptor. The mammal can be a human. The viral particle can be a lentiviral particle. The antigen receptor can be a chimeric antigen receptor. The viral particle can target one or more cancer cells. The one or more cancer cells can express a tumor-specific antigen. The selected antigen receptor can target the tumor-specific antigen. The tumor-specific antigen can be CD19. The antigen receptor targeting the tumor-specific antigen can be a CAR targeting CD19. The nucleic acid encoding the CAR targeting CD19 can comprise a nucleic acid sequence set forth in SEQ ID NO:1. The exogenous molecule can comprise an antigen-binding domain that can recognize CD3 and wherein the viral particle further comprises nucleic acid encoding the antigen-binding domain that can recognize CD3. The antigen-binding domain can be a single-chain variable fragment. The nucleic acid encoding the single-chain variable fragment that can recognize CD3 can comprise a nucleic acid sequence set forth in SEQ ID NO:2. The administration can be an intravenous injection or an intratumoral injection. The nucleic acid encoding the selected antigen receptor can comprise nucleic acid encoding a scFv set forth in Table 1.

In another aspect, this document features a method for treating a mammal having cancer comprising cancer cells expressing a selected antigen. The method comprises (or consists essentially of or consists of) administering a cell capable of producing a viral particle to the mammal, wherein the viral particle comprises nucleic acid encoding an antigen receptor targeting the selected antigen, wherein the administration is effective to generate T cells expressing the antigen receptor in vivo. The mammal can be a human. The viral particle can be a lentiviral particle. The cancer can be a B cell cancer. The antigen receptor can be a chimeric antigen receptor. The nucleic acid encoding the antigen receptor can comprise nucleic acid encoding a scFv set forth in Table 1. The administration can be an intravenous injection or an intratumoral injection.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

In FIG. 1A, viral particles containing nucleic acid encoding CARs are delivered intravenously or by intratumoral injection to a tumor site. The viral particles can include one or more targeting molecules (e.g., a single chain antibody that binds to CD3) that help direct the viral particles to infect T cells in vivo. In FIG. 1B, cells capable of producing viral particles containing nucleic acid encoding CARs are delivered by intratumoral injection to a tumor site. The produced viral particles can include one or more targeting molecules (e.g., a single chain antibody that binds to CD3) that help direct the produced viral particles to infect T cells in vivo.

FIG. 2 shows an exemplary nucleic acid sequence (SEQ ID NO:1) encoding a CAR targeting a cluster of differentiation 19 (CD19) antigen.

FIG. 3 shows an exemplary nucleic acid sequence (SEQ ID NO:2) encoding a modified viral envelope polypeptide capable of target a cluster of differentiation 3 (CD3) antigen.

FIG. 4A: Titration Assay of virus producing cells to T cells. Approximately 5:1 virus producing cell:T cell is used to achieve sufficient transduction of T cells and generation of CART cells. FIG. 4B: Cytotoxicity Assay. CART cells generated through 293 T cell direct transduction of T cells exhibited potent antitumor activity against the CD19$^+$ cell line NALM6 but not the CD19 negative cell line MOLM13.

FIGS. 5A-5F. (A) Schema of the experiment. NSG mice were engrafted with the human CD19$^+$, luc$^+$ NALM6 cell line subcutaneously. Engraftment was confirmed by bioluminescent imaging, and mice were then randomized to receive either ex-vivo expanded human CART19 or virus producing 293T cells transfected with human CAR19 plasmid followed by normal T cells intravenously. (B) Peripheral blood sampling 10 days later shows CART19 generation. Flow blots of human CD45$^+$ cells: CD3 on the X axis, and CAR on the Y axis. (C) Percentage of CAR$^+$ T cells detected in peripheral blood was higher when 293T cells were injected IV with T cells compared to ex-vivo transduced CART19 cells. (D) Antitumor activity after in vivo generation of CART19 cells was similar to that observed using ex vivo generated CART19. Untreated mice died of the disease within 20 days. (E) Mice treated with either (1) ex vivo generated CART19 or (2) 293T cells plus T cells (in vivo generated CART19) exhibited similar antitumor control on day 14 and day 19. (F) Mice treated with either (1) ex vivo generated CART19 or (2) 293T cells plus T cells (in vivo generated CART19) exhibited similar overall survival that is improved compared to untreated mice.

DETAILED DESCRIPTION

Figure 1A:
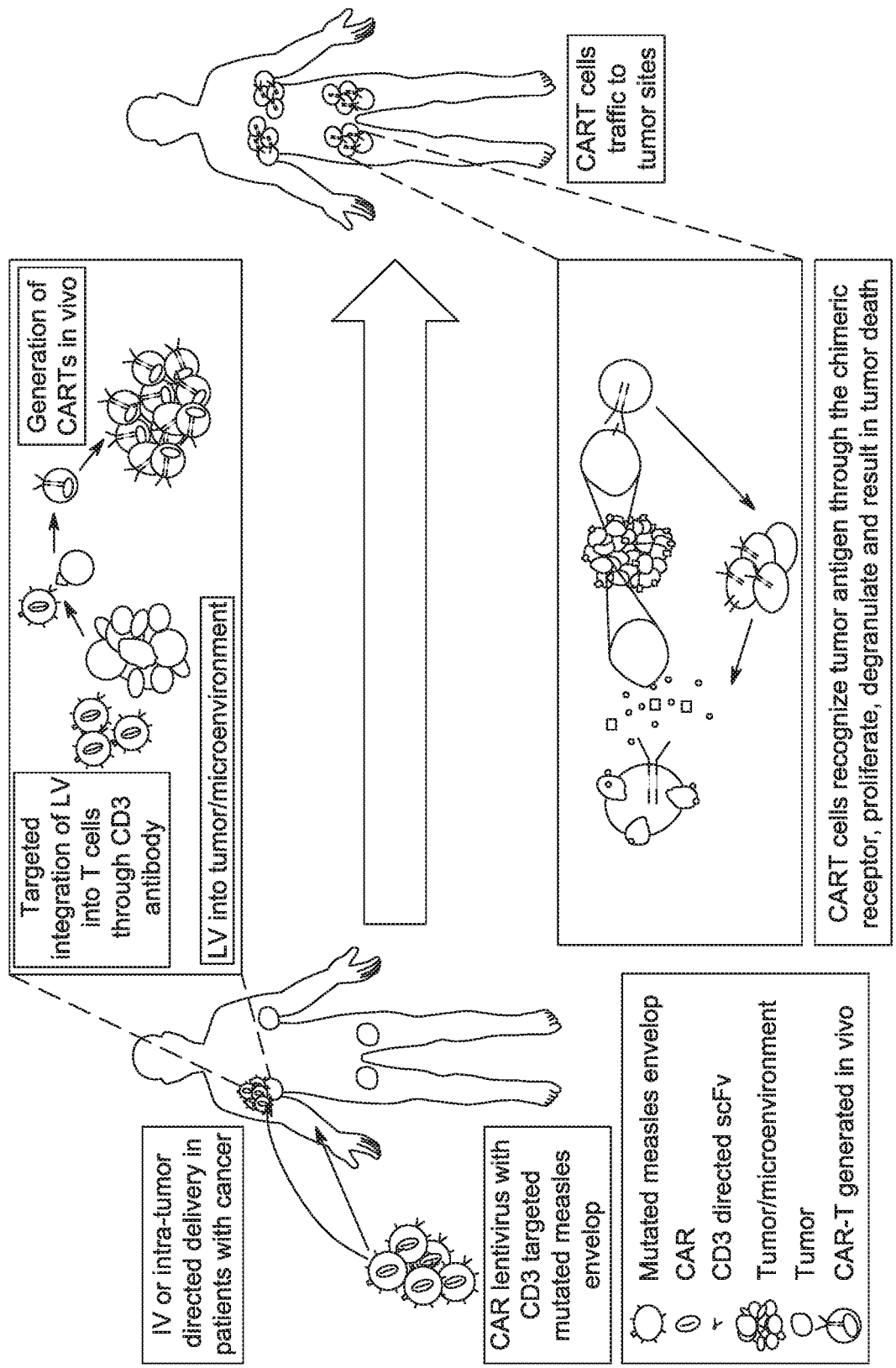
FIGS. 1A-1B contain schematic diagrams of exemplary methods for in vivo generation of CART cells.

This document provides methods and materials for generating T cells expressing a selected antigen receptor (e.g., a CAR) in vivo. In some cases, one or more viral particles containing (e.g., engineered to contain) nucleic acid encoding a selected antigen receptor (e.g., a selected CAR) can be administered to a mammal to generate T cells in vivo that express that selected antigen receptor. For example, one or more viral particles containing nucleic acid encoding a CAR can be administered to a mammal where the viral particle(s) can transduce one or more T cells such that the T cell(s) express the nucleic acid encoding the selected CAR, thereby generating CART cells expressing the selected antigen receptor within the mammal. In some cases, one or more cells capable of producing one or more viral particles containing (e.g., engineered to contain) nucleic acid encoding a selected antigen receptor (e.g., a selected CAR) can be administered to a mammal to generate T cells in vivo that express that selected antigen receptor. For example, one or more cells capable of producing viral particles containing nucleic acid encoding a CAR can be administered to a mammal such that the cell(s) produce infectious viral particles containing nucleic acid encoding the CAR, which in turn can transduce one or more T cells such that the T cell(s) express the nucleic acid encoding the selected CAR, thereby generating CART cells expressing the selected antigen receptor within the mammal.

In some embodiments, this document provides viral particles containing nucleic acid encoding a selected antigen receptor. A viral particle described herein (e.g., a viral particle containing nucleic acid encoding a selected antigen receptor) can include viral components (e.g., genetic material (e.g., a viral genome), a capsid, and/or an envelope) from any appropriate virus. A virus can be an infectious virus. A virus can be a chimeric virus. A virus can be a recombinant virus. In some cases, a viral particle can include viral components from the same virus. In some cases, a viral particle can be a recombinant viral particle. For example, a recombinant viral particle can include viral components from different viruses (e.g., two or more different viruses). Examples of viruses from which viral components can be obtained include, without limitation, retroviruses, (e.g., lentiviruses), measles viruses, canine distemper viruses, Cedar viruses, and Nipah viruses. For example, a viral particle can include a lentiviral backbone and a measles virus envelope.

A viral particle described herein (e.g., a viral particle containing nucleic acid encoding a selected antigen receptor) can contain (e.g., can be engineered to contain) nucleic acid encoding any appropriate antigen receptor. In some cases, an antigen receptor can be a heterologous antigen receptor. In some cases, an antigen receptor can be a CAR. In some cases, an antigen receptor can be a tumor antigen receptor (e.g., an antigen receptor that targets a tumor antigen). In cases where a viral particle contains nucleic acid encoding a tumor antigen receptor, the tumor antigen receptor can target any appropriate tumor antigen. In some cases, a tumor antigen can be a cell surface tumor antigen. In some cases, a tumor antigen can be a tumor-associated antigen (TAA; e.g., an antigen, such as an abnormal protein, present on tumor cells). In some cases, a tumor antigen can be a tumor-specific antigen (TSA; e.g., an antigen present only on tumor cells). Examples of tumor antigens that can be targeted by a selected antigen receptor include, without limitation, CD19, mucin 1 (MUC-1), human epidermal growth factor receptor 2 (HER-2), estrogen receptor (ER), epidermal growth factor receptor (EGFR), folate receptor alpha, mesothelin, alphafetoprotein (AFP), carcinoembryonic antigen (CEA), CA-125, epithelial tumor antigen (ETA), melanoma-associated antigen (MAGE), membrane cofactor protein 11 (MCP11, also known as CD46), CD123, CD33, CLEC12A, Mesothelin, CD22, CD20, BCMA, CS-1, CD138, CD44v6, NKGD2A, and CD38. In some cases, an antigen receptor can be a disease-associated antigen receptor (e.g., a disease-associated antigen that is associated with a disease other than cancer). In cases where a viral particle contains nucleic acid encoding a disease-associated antigen receptor, the disease-associated antigen receptor can target any appropriate disease-associated antigen. In some cases, a viral particle described herein can contain nucleic acid encoding a CAR targeting CD19 (e.g., an anti-CD19 CAR). Examples of scFv sequences and other binding sequences that can be used to design a CAR to a particular tumor antigen include, without limitation, those set forth in Table 1.

TABLE 1

Representative scFv antibodies and sequences for targeting CARs to tumor antigens.

| Antigen | scFv antibody name | Reference(s) |
|---|---|---|
| CD19 | FMC63 | Milone et al., Mol. Ther., 17(8):1453-64 (2009) (PMID: 26330164) |
| | MOR208 | Kellner et al., Leukemia, 27(7):1595-8 (2013) (FWD: 23277329) |
| | Humanized scFv | International Patent Application Publication No. W02015157252 |
| | 4G7 | EP Patent No. EP2997141 |
| | Low affinity scFv | Chinese Patent No. CN107406517 |
| MUC-1 | 5E5 | Posey et al., Immunity, 45(5):947-948 (2016) (PMID: 27851918) |
| HER-2 | 4D5 | Ohnishi et al., Br. J. Cancer, 71(5):969-73 (1995) (PMID: 7734322) |
| | | Forsberg et at, Cancer Res., 79(5):899-904 (2019) (PMID: 30622115) |
| | | Nellan et al., J. Immunother. Cancer, 6(1):30 (2018) (PMID: 29712574) |
| | | Priceman et al., Clin Cancer Res., 24(1):95-105 (2018) (PMID: 29061641) |
| | FRP5 | Bielamowics et al., Neuro. Oncol., 20(4):506-518 (2018) (PMID: 29016929) |
| EGFR | M27 | Jiang et al., Cancer Immunol. Res., 6(11):1314-1326 (2018) (PMID: 30201736) |
| | Cetuximab | Caruso et al., Cancer Res., 75(17):3505-18 (2015) (PMID: 26330164) |
| Folate receptor alpha | C4 based | Ao et al., J. Immunother., 42(8):284-296 (2019) (PMID: 31261167) |
| | MOv19 | Song et al., J. Hematol. Oncol., 9(1):56 (2016) (PMID: 27439908) |
| Mesothelin | SS1 | Haas et al., Mol. Ther., S1525-0016(19)30328-4 (2019) (PMID: 31420241) |
| | M clone | Adusumilli et al., Sci. Trarisl. Med., 6(261):261ra151 (2014) (PMID: 25378643) |
| AFP | ET1402L1 | Liu et al., Clin. Cancer Res., 23(2):478-488 (2017) (PMID: 27535982) |
| CEA | Anti-CEA scFv | Chi et al., Cancer Med., 8(10):4753-4765 (2019) (PMID: 31237116) |
| | CEACAM5 | Thistlethwaite et at, Cancer Immunol. Immunother., 66(11):1425-1436 (2017) (PMID: 28660319) |
| | hMN14 | Katz et al., Clin. Cancer Res., 21(14):3149-59 (2015) (PMID: 25850950) |
| CD123 | 22172,22176 | Gill et al., Blood, 123(15):2343-54 (2014) (PMID: 24596416) |
| | Humanized scFv | US Patent Application Publication No. 2016/0068601 |
| | Humanized scFv | EP Patent No. EP2968415 |
| | Tagrazofusp based | Pemmaraju et al. N. Engl. J. Med., 380(17):1628-1637 (2019) (PMID: 31018069) |
| CD33 | MY96 | Kenderian et at, Leukemia, 29(8):1637-47 (2015) (PMID: 25721896) |
| | Humanized scFv | International Patent Application Publication No. W02016014576 |
| CLEC12A | Humanized scFv | US Patent Application Publication No. US20160051651 |
| | CLL1 scFv | International Patent Application Publication No. W02016120219 |
| CD22 | M0971 | Fry et at, Nat. Med., 24(1):20-28 (2018) (PMID: 29155426) |
| | Humanized scFv clones | International Patent Application Publication No. WO/2016/164731 |
| | Inotuzumab based | Kantarjian et at, N. Engl. J. Med., 375(8):740-53 (2016) (PMID: 27292104) |
| | Moxetumomab based | Kreitman et al., Leukemia, 32(8):1768-1777 (2018) (PMID: 30030507) |
| CD20 | Rituximab | Zhang et al., Signal Transduct Target Ther., 1:16002 (2016) (PMID: 29263894) |
| | Leu 16 | Lee et al., J. Immunother., 41(1):19-31 (2018) (PMID: 29176334) |
| | CD20 scFvs | International Patent Application Publication No. WO/2016/164731 |
| BCMA | BCMA-02 | Raje et al., N. Engl. J. Med., 380(18):1726-1737 (2019) (PMID: 31042825) |
| | LCAR38 | Zhao et al., J. Hematol. Oncol., 11(1):141 (2018) (PMID: 30572922) |
| | BCMA scFv | Smith et al., Cancer Immunol. Res., 7(7):1047-1053 (2019) (PMID: 31113804) |

TABLE 1-continued

Representative scFv antibodies and sequences for targeting CARs to tumor antigens.

| Antigen | scFv antibody name | Reference(s) |
|---|---|---|
| | Biepitopic | Xu et al., Proc. Natl. Acad. Sci. USA, 116(19):9543-9551 (2019) (PMID: 30988175) |
| | NVS BCMA | Cohen et at, J. Clin. Invest., 129(6):2210-2221 (2019) (PMID: 30896447) |
| CS-1 | CS1R | Wang et al., Clin. Cancer Res., 24(1):106-119 (2018) (PMID: 29061640) |
| | CS1 ScFv | Chu et al., Leukemia, 28(4):917-27 (2014) (PMID: 24067492) |
| | Elotuzumab based | Dimopoulos et al., N. Engl. J. Med., 379(19):1811-1822 (2018) (PMID: 30403938) |
| CD138 | ScFv | Sun et al., Oncotarget., 10(24):2369-2383 (2019) (PMID: 31040928) |
| CD44v6 | Humanized scFv | Leuci et al., Oncoimmunology, 7(5):e1423167 (2018) (PMID: 29721373) |
| | cMAb U36 | Sandstrom et al., Int. J. Oncol., 40(5):1525-32 (2012) (PMID: 22307465) |
| NKG2D | scFv | Yang et al., J. Immunother. Cancer, 7(1):171 (2019) (PMID: 31288857) |
| | NKG2Dg scFv | Parihar et al., Cancer Immunol. Res., 7(3):363-375 (2019) (PMID: 30651290) |
| CD38 | Nanobody CD38 | An et al., Mol. Pharm., 15(10):4577-4588 (2018) (PMID: 30185037) |
| | Humanized scFv | Yoshida et al., Clin. Transl. Immunology, 5(12):e116 (2016) (PMID: 28090317) |
| GPRC5D | Humanized scFv | Smith et al., Sci. Transl. Med., 11(485)eaau7746 (2019) (PMID: 30918115) |
| CD79b | scFv (L-H) and (H-L) | Ormhoj et al., Clin. Cancer Res., (2019) (PMID: 31439577) |
| CD103 | M290 | Zhang et al., Am. J. Transplant., 9(9):2012-23 (2009) (PMID: 19645708) |
| FAP | FAP5 | Wang et al., Cancer Immunol. Res., 2(2):154-66 (2014) (PMID: 24778279) |
| CD70 | Human CD70 | Park et al., Oral Oncol., 78:145-150 (2018) (PMID: 29496042) |
| MUC16 | 4H11 | Koneru et al., Oncoimmunol., 4(3):e994446 (2015) (PMID: 25949921) |
| IL13Ra2 | IL13R | Kong et al., Clin. Cancer Res., 18(21):5949-60 (2012) (PMID: 22966020) |

In some cases, a viral particle described herein (e.g., a viral particle containing nucleic acid encoding a selected antigen receptor) can be used to target any appropriate type of cell. For example, a viral particle described herein can be used to target cancer cells presenting an antigen (e.g., a tumor antigen) associated with a particular cancer. Examples of antigens associated with a particular cancer include, without limitation, CD19 (associated with B cell lymphomas, acute lymphoblastic leukemia (ALL), and chronic lymphocytic leukemia (CLL)), AFP (associated with germ cell tumors and/or hepatocellular carcinoma), CEA (associated with bowel cancer, lung cancer, and/or breast cancer), CA-125 (associated with ovarian cancer), MUC-1 (associated with breast cancer), ETA (associated with breast cancer), MAGE (associated with malignant melanoma), CD33, CD123, CLEC12A (myeloid diseases), CD22, CD20, kappa, lambda (B cell malignancies), folate receptor alpha (ovarian cancer), BCMA, CS-1, CD138, CD38 (multiple myeloma), universal peptide receptor, T cell receptor (T cell lymphoma and leukemia), CD5, CD7, and CD2 (T cell lymphoma and leukemia). For example, a viral particle described herein can be used to target disease cells (e.g., disease cells other than cancer cells) presenting an antigen (e.g., a disease-associated antigen) associated with a particular disease (e.g., a disease other than cancer). Examples of antigens with a particular disease include, without limitation, Viral Capsid Antigen (associated with Mononucleosis) and GP120 (associated with HIV).

A viral particle described herein (e.g., a viral particle containing nucleic acid encoding a selected antigen receptor) can be engineered to contain nucleic acid encoding a selected antigen receptor using any appropriate methods and/or techniques. In some cases, nucleic acid encoding a selected antigen receptor can be incorporated into a viral genome. Nucleic acid encoding a selected antigen receptor can be introduced into a viral particle using any appropriate methods and/or techniques. For example, nucleic acid encoding a selected antigen receptor can be introduced into a viral particle using molecular cloning techniques. In some cases, a viral particle described herein can contain nucleic acid encoding a CAR targeting CD19 (e.g., an anti-CD19 CAR). An exemplary nucleic acid sequence encoding an anti-CD19 CAR can include a sequence as set forth in SEQ ID NO:1.

In some cases, a viral particle described herein (e.g., a viral particle containing nucleic acid encoding a selected antigen receptor) can target (e.g., can be engineered to target) one or more T cells. For example, a viral particle described herein can include one or more exogenous molecules that can direct the viral particle to target (e.g., target and infect) one or more T cells in vivo. Exogenous molecules that can direct a viral particle to target one or more T cells also can be referred to as targeting molecules. An exogenous molecule can target any appropriate type of T cell. In some cases, a T cell can be a naïve T cell. In some cases, a T cell can be an immunosuppressive T cell. Examples of T cells that can be targeted by one or more viral particles described herein include, without limitation, cytotoxic T cells (CTLs; e.g., $CD4^+$ CTLs and/or $CD8^+$ CTLs), regulatory T cells, and memory subsets of T cells. In some cases, a viral particle described herein can target a particular type of T cell. An exogenous molecule can target any appropriate molecule present on one or more T cells. Examples of molecules present on a T cell that can be targeted via a targeting molecule incorporated into a viral particle described herein include, without limitation, a component of a T cell receptor (such as a CD3 polypeptide, TCR-α chain polypeptide, a TCR-β chain polypeptide, or a ζ-chain polypeptide), CD2, CD8, CD4, Cd25, CD5, and CD7. An exogenous molecule can be any appropriate type of molecule that can target a molecule present on one or more T cells. In some cases, an exogenous molecule can contain an antigen-binding domain (e.g., an antigen-binding domain that recognizes an antigen on T cell) such as single-chain variable fragments (scFvs), antibodies, antigen-binding fragments (Fabs), single-domain antibodies (sdAbs), affibodies, and/or receptor proteins. In some cases, a targeting molecule incorporated into a viral particle described herein can be an antigen (e.g., an antigen that is recognized by an antigen-binding domain on a T cell). In some cases, an exogenous molecule can be a receptor (e.g., a receptor that forms a complex with a ligand on T cell). In some cases, a targeting molecule can be a ligand (e.g., a ligand that forms a complex with a receptor on a T cell). Examples of targeting molecules that can target a viral particle described herein to one or more T cells include, without limitation, anti-CD3 molecules containing CD3 antigen-binding domains (e.g., anti-CD3 scFvs), CD2, CD8, CD4, Cd25, CD5, and CD7.

In cases where a viral particle described herein (e.g., a viral particle containing nucleic acid encoding a selected antigen receptor) includes one or more exogenous molecules (e.g., one or more targeting molecules that can direct the viral particle to target one or more T cells), the targeting molecule can be engineered into the viral particle as an exogenous component of the viral particle using any appropriate methods and/or techniques. For example, a viral particle described herein can be engineered to include one or more viral components (e.g., modified genetic material (e.g., a viral genome), a modified capsid, and/or a modified envelope) that are modified to include one or more targeting molecules. In some cases, a viral particle described herein can include a modified envelope that includes one or more targeting molecules. An exogenous targeting molecule can be incorporated into a viral component (e.g., an envelope) using any appropriate methods and/or techniques. For example, a viral particle can include nucleic acid encoding a targeting molecule such that the targeting molecule is expressed and incorporated into a component (e.g., an envelope) of the viral particle. In cases where a viral particle described herein includes one or more targeting molecules containing a CD3 antigen-binding domain (e.g., one or more anti-CD3 scFvs), the viral particle can contain nucleic acid encoding the targeting molecule(s). For example, a viral particle including one or more anti-CD3 scFvs can contain nucleic acid encoding the anti-CD3 scFvs. An exemplary nucleic acid sequence encoding an anti-CD3 scFv can include a sequence as set forth in SEQ ID NO:2.

In some cases, a viral particle described herein (e.g., a viral particle containing nucleic acid encoding a selected antigen receptor) can include a lentiviral backbone and a measles virus envelope, can contain nucleic acid encoding an antigen receptor (e.g., a CAR) that can target CD19 (e.g., an anti-CD19 CAR), and can contain nucleic acid encoding a targeting molecule (e.g., an antigen-binding domain that recognizes an antigen on T cell such as an anti-CD3 scFv) such that the measles virus envelope presents the antigen-binding domain that recognizes an antigen on T cell. For example, a viral particle described herein can have a lentiviral backbone and a measles virus envelope, can contain nucleic acid encoding a CAR targeting CD19 as set forth in SEQ ID NO:1, and can contain nucleic acid encoding an anti-CD3 scFv as set forth in SEQ ID NO:2, such that the measles virus envelope presents the anti-CD3 scFv.

This document also provides cells capable of producing one or more viral particles described herein (e.g., one or more viral particles containing nucleic acid encoding a selected antigen receptor). A cell capable of producing one or more viral particles described herein can be any appropriate type of cell. Examples of cells that can be used to produce one or more viral particles described herein include, without limitation, 2293T, HEK293F, and Sup T1 cells. Any appropriate method and/or technique can be used to engineer a cell capable of producing one or more viral particles described herein (e.g., one or more viral particles containing nucleic acid encoding a selected antigen receptor). For example, a cell can be transduced with one or more viral particles described herein to engineer the cell to be capable of producing one or more viral particles described herein. In some cases, a cell can be transduced with one or more viral particles containing nucleic acid encoding a selected antigen receptor (e.g., nucleic acid encoding a CAR targeting CD19 as set forth in SEQ ID NO:1), and containing nucleic acid sequence encoding a targeting molecule that can direct the viral particle to target one or more T cells (e.g., nucleic acid encoding an anti-CD3 scFv as set forth in SEQ ID NO:2) to engineer the cell to be capable of producing one or more viral particles described herein. To generate these cells, virus producing cells can be transfected with a CAR plasmid, an envelope plasmid, and a packaging plasmid. Cells can then be purified and injected in situ or in vivo.

In some cases, a cell capable of producing one or more viral particles described herein (e.g., one or more viral particles containing nucleic acid encoding a selected antigen receptor) can produce one or more viral particles including a lentiviral backbone and a measles virus envelope, where the viral particle(s) contain nucleic acid encoding an antigen receptor (e.g., a CAR) that can target CD19 (e.g., an anti-CD19 CAR), and where the viral particle(s) contain nucleic acid encoding an antigen-binding domain that recognizes an antigen on T cell (e.g., an anti-CD3 scFv) such that the measles virus envelope presents the antigen-binding domain that recognizes an antigen on T cell. For example, a cell capable of producing one or more viral particles described herein can produce one or more viral particles having a lentiviral backbone and a measles virus envelope, where the viral particle(s) contain nucleic acid encoding a CAR targeting CD19 as set forth in SEQ ID NO:1, and where the viral particle(s) contain nucleic acid encoding an anti-CD3 scFv as set forth in SEQ ID NO:2, such that the measles virus envelope presents the anti-CD3 scFv.

This document also provides methods and materials for generating T cells expressing the selected antigen receptor within the mammal. In some cases, one or more viral particles provided herein (e.g., one or more viral particles containing nucleic acid encoding a selected antigen receptor) and/or one or more cells capable of producing such viral particles can be administered to a mammal to generate T cells expressing that selected antigen receptor within the mammal. For example, one or more viral particles containing nucleic acid encoding a selected antigen receptor (e.g., a selected CAR) administered to a mammal can transduce one or more T cells within the mammal (e.g., to introduce the nucleic acid encoding the selected antigen receptor into the T cells such that the T cells express the selected antigen receptor) to generate one or more T cells expressing the selected antigen receptor (e.g., one or more CART cells) within the mammal. For example, one or more cells capable of producing viral particles containing nucleic acid encoding a selected antigen receptor (e.g., a selected CAR) administered to a mammal can result in the production of infectious viral particles, which in turn can transduce one or more T cells within the mammal (e.g., to introduce the nucleic acid encoding the selected antigen receptor into the T cells such that the T cells express the a selected antigen receptor) to generate one or more T cells expressing the selected antigen receptor (e.g., one or more CART cells) within the mammal.

In some cases, when one or more viral particles provided herein (e.g., one or more viral particles containing nucleic acid encoding a selected antigen receptor) and/or one or more cells capable of producing such viral particles are administered to a mammal to generate T cells expressing that selected antigen receptor within the mammal, the T cells expressing that selected antigen receptor do not target normal (e.g., healthy) cells.

In some cases, when one or more viral particles provided herein (e.g., one or more viral particles containing nucleic acid encoding a selected antigen receptor) and/or one or more cells capable of producing such viral particles are administered to a mammal to generate T cells expressing that selected antigen receptor within the mammal, the T cells expressing that selected antigen receptor can avoid the mammal's immune system.

In some cases, when one or more viral particles provided herein (e.g., one or more viral particles containing nucleic acid encoding a selected antigen receptor) and/or one or more cells capable of producing such viral particles are administered to a mammal to generate T cells expressing that selected antigen receptor within the mammal, the T cells expressing that selected antigen receptor can target non cancer cells (e.g., auto immune disease cells) and can be non-pathogenic.

In some cases, when one or more cells capable of producing one or more viral particles provided herein (e.g., one or more viral particles containing nucleic acid encoding a selected antigen receptor) are administered to a mammal to generate T cells expressing that selected antigen receptor within the mammal, the one or more cells capable of producing one or more viral particles provided herein can continue to generate viral particles in situ. In some cases, these cells can produce virus for about 2 to 3 days until they are eliminated.

One or more viral particles provided herein (e.g., one or more viral particles containing nucleic acid encoding a selected antigen receptor) and/or one or more cells capable of producing such viral particles can be administered to any appropriate mammal to generate T cells expressing that selected antigen receptor within the mammal. In some cases, a mammal (e.g., a human) can have cancer. In some cases, a mammal (e.g., a human) can have a disease other than cancer. Examples of mammals within which T cells expressing a selected antigen receptor can be generated as described herein include, without limitation, humans, non-human primates (e.g., monkeys), dogs, cats, horses, cows, pigs, sheep, mice, and rats. In some cases, one or more viral particles provided herein and/or one or more cells capable of producing such viral particles can be administered to a human to generate T cells expressing a selected antigen receptor within the human.

In some cases, one or more viral particles provided herein (e.g., one or more viral particles containing nucleic acid encoding a selected antigen receptor) and/or one or more cells capable of producing such viral particles can be administered to a mammal having cancer to treat the mammal. For example, one or more viral particles containing nucleic acid encoding a selected tumor antigen receptor and/or one or more cells capable of producing viral particles containing nucleic acid encoding a selected tumor antigen receptor can be administered to a mammal having a cancer (e.g., a cancer containing cancer cells presenting a tumor antigen targeted by the selected tumor antigen receptor) to generate T cells expressing the selected tumor antigen receptor within the mammal to treat the mammal (e.g., by specifically targeting the cancer cells presenting a tumor antigen targeted by the selected tumor antigen receptor).

In some cases, when treating a mammal having cancer as described herein (e.g., by administering one or more viral particles containing nucleic acid encoding a selected antigen receptor and/or one or more cells capable of producing such viral particles to a mammal to generate T cells expressing a selected antigen receptor within the mammal), the mammal can have any type of cancer. A cancer can be a primary cancer or a metastatic cancer. In some cases, a cancer can include one or more solid tumors. In some cases, a cancer can be a cancer in remission. In some cases, a cancer can include quiescent (e.g., dormant or non-dividing) cancer cells. In some cases, a cancer can be cancer that has escaped chemotherapy and/or has been non-responsive to chemotherapy. Examples of cancers that can be treated by administering one or more viral particles containing nucleic acid encoding a selected antigen receptor and/or one or more cells capable of producing such viral particles to a mammal to generate T cells expressing an antigen receptor within the mammal include, without limitation, B cell lymphomas, ALLs, CLLs, germ cell tumors, hepatocellular carcinomas, bowel cancers, lung cancers, breast cancers, ovarian cancers, malignant melanomas, AML, multiple myeloma, thyroid cancer, head and neck cancers, and brain cancers. In some cases, a mammal treated as described herein can have a cancer containing cancer cells presenting a tumor antigen. Examples of tumor antigens associated with one or more particular cancers include, without limitation, CD19 (associated with B cell lymphomas, ALLs, and CLLs), AFP (associated with germ cell tumors and/or hepatocellular carcinomas), CEA (associated with bowel cancers, lung cancers, and/or breast cancers), CA-125 (associated with ovarian cancers), MUC-1 (associated with breast cancers), ETA (associated with breast cancers), MAGE (associated with malignant melanomas), CD38 (associated with multiple myeloma), CD33, CD123, CLEC12A (myeloid diseases), CD22, CD20, kappa, lambda (B cell malignancies), folate receptor alpha (ovarian cancer), BCMA, CS-1, CD138, CD38 (multiple myeloma), universal peptide receptor, T cell receptor (T cell lymphoma and leukemia), CD5, CD7, and CD2 (T cell lymphoma and leukemia). In some cases, a human having a B cell lymphomas, ALL, or CLL, can be treated by administering one or more viral particles expressing a CAR targeting CD19 to generate CART cells expressing a CAR targeting CD19 within the human.

In some cases, when treating a mammal having cancer as described herein (e.g., by administering one or more viral particles containing nucleic acid encoding a selected antigen receptor and/or one or more cells capable of producing such viral particles to a mammal to generate T cells expressing a selected antigen receptor within the mammal), the mammal can be identified as having cancer. Any appropriate method can be used to identify a mammal as having cancer. For example, imaging techniques can be used to identify a mammal as having cancer.

In some cases, when treating a mammal having cancer as described herein (e.g., by administering one or more viral particles containing nucleic acid encoding a selected antigen receptor and/or one or more cells capable of producing such viral particles to a mammal to generate T cells expressing a selected antigen receptor within the mammal), the treatment can reduce one or more symptoms of the cancer in the mammal. For example, the treatment can reduce the number of cancer cells (e.g., cancer cells expressing a tumor antigen) within a mammal. For example, the treatment can reduce the size (e.g., volume) of one or more tumors (e.g., tumors expressing a tumor antigen) within a mammal.

In some cases, one or more viral particles provided herein (e.g., one or more viral particles containing nucleic acid encoding a selected antigen receptor) and/or one or more cells capable of producing such viral particles can be administered to a mammal having a disease (e.g., a disease other than cancer) to treat the mammal. For example, one or more viral particles containing nucleic acid encoding a selected disease-associated antigen receptor and/or one or more cells capable of producing viral particles containing nucleic acid encoding a selected disease-associated antigen receptor can be administered to a mammal having a disease (e.g., a disease containing disease cells presenting a disease-associated antigen targeted by the selected disease-associated antigen receptor) to generate T cells expressing a selected antigen receptor within the mammal to treat the mammal (e.g., by specifically targeting the disease cells presenting a disease-associated antigen targeted by the selected disease-associated antigen receptor).

In some cases, when treating a mammal having a disease (e.g., a disease other than cancer) as described herein (e.g., by administering one or more viral particles containing nucleic acid encoding a selected antigen receptor and/or one or more cells capable of producing such viral particles to a mammal to generate T cells expressing a selected antigen receptor within the mammal), the mammal can have any type of disease. For example, a mammal having an infection (e.g., a viral infection or a bacterial infection) can be treated as described herein. Examples of infections that can be treated as described herein include, without limitation, influenza infections, hepatitis infections, fungal infections, CMV infections, EBV associated infections, HHV6 infections, and viral infections. In some cases, an infected cell can present a disease-associated antigen (e.g., a viral antigen or a bacterial antigen). Examples of disease-associated antigens associated with one or more particular infections include, without limitation, glactomannan (associated with *Aspergillus* and fungal infections) and candin (*Candida* antigen).

In some cases, when treating a mammal have a disease (e.g., a disease other than cancer) as described herein (e.g., by administering one or more viral particles containing nucleic acid encoding a selected antigen receptor and/or one or more cells capable of producing such viral particles to a mammal having a disease other than cancer to generate T cells expressing a selected antigen receptor within the mammal), the mammal can be identified as having a disease. Any appropriate method can be used to identify a mammal as having a disease. For example, when a disease is an infection, an infestation, and/or an autoimmune disease can be used to identify a mammal as having an infection.

In some cases, when treating a mammal having a disease (e.g., a disease other than cancer) as described herein (e.g., by administering one or more viral particles containing nucleic acid encoding a selected antigen receptor and/or one or more cells capable of producing such viral particles to a mammal to generate T cells expressing a selected antigen receptor within the mammal), the treatment can reduce one or more symptoms of the disease in the mammal. For example, when the disease is an infection, the treatment can reduce the number of infected cells within a mammal.

One or more viral particles provided herein (e.g., one or more viral particles containing nucleic acid encoding a selected antigen receptor) and/or one or more cells capable of producing such viral particles can be administered to a mammal to generate T cells expressing that selected antigen receptor within the mammal using any appropriate method and/or technique. In some cases, one or more viral particles described herein can be administered into or near a tumor. Examples of methods of administering one or more viral particles described herein to a mammal can include, without limitation, injections such as intratumoral, intravenous (IV), intradermal (ID), subcutaneous, in situ in the lymph node, or intra peritoneal injections. In some cases, when one or more viral particles described herein are administered to a mammal as described herein, the administration can be IV administration or intratumoral administration. In some cases, when one or more cells capable of producing one or more viral particles described herein are administered to a mammal as described herein, the administration can be intratumoral administration.

One or more T cells expressing that selected antigen receptor generated within a mammal as described herein (e.g., by administering one or more viral particles containing nucleic acid encoding a selected antigen receptor and/or one or more cells capable of producing such viral particles to a mammal to generate T cells expressing a selected antigen receptor within the mammal) can target a cell (e.g., a cell presenting an antigen recognized by the selected antigen receptor) in any appropriate location within the mammal. In some cases, a T cell expressing a selected antigen generated within a mammal as described herein can target a cell at a primary location (e.g., a site of administration) within the mammal. In some cases, a T cell expressing a selected antigen generated within a mammal as described herein can target a cell at one or more secondary locations (e.g., a site different from the site of administration) within a mammal. In some cases, a T cell expressing a selected antigen generated within a mammal as described herein can target cells at both a primary location and at one or more secondary locations within a mammal having cancer. For example, a T cell expressing a selected antigen generated within a mammal as described herein can target cells at a primary location within a mammal and can leave the primary location and can migrate to target cells at one or more secondary locations.

In some cases, one or more viral particles provided herein (e.g., one or more viral particles containing nucleic acid encoding a selected antigen receptor) and/or one or more cells capable of producing such viral particles can be administered to a mammal together with one or more additional therapeutic agents. For example, when treating a mammal having cancer as described herein, one or more viral particles provided herein and/or one or more cells capable of producing such viral particles can be administered to a mammal together with one or more additional anti-cancer treatments. Examples of anti-cancer treatments include, without limitation, surgery, radiation therapy, chemotherapy, targeted therapy, hormonal therapy, angiogenesis inhibitors, immunosuppressants, immunostimulants, immunomodulatory agents, and small molecule inhibitors. For example, when treating a mammal having an infection as described herein, one or more viral particles provided herein and/or one or more cells capable of producing such viral particles can be administered to a mammal together with one or more additional agents used to treat an infection. Examples of agents used to treat infections include, without limitation, antivirals, antibiotics, and antifungals. In cases where one or more viral particles provided herein and/or one or more cells capable of producing such viral particles are used with additional therapeutic agents, the one or more additional therapeutic agents can be administered at the same time or independently. In some cases, one or more viral particles provided herein and/or one or more cells capable of producing such viral particles can be administered first, and the one or more additional therapeutic agents administered second, or vice versa.

In some cases, a T cell generated as described herein to express a selected antigen receptor using one or more viral particles provided herein (and/or one or more cells capable of producing such viral particles) can express the selected antigen receptor (an antigen receptor heterologous to that T cell) in addition to a native antigen receptor of that T cell (e.g., the T cell's native TCR).

In some cases, virus producing cells described herein can be 293 T cells or any other type of virus producing cell. In some cases, such virus producing cells can be injected intravenously, intra tumorally, subcutaneously, or regionally into local lymph nodes. As described herein, a virus producing cell can be transfected with a lentivirus or retrovirus plasmid encoding a CAR construct (e.g., stably tranfected with a CAR-encoding sequence, envelope-encoding sequence, and packaging plasmid(s)) and cryopreserved for future use. In some cases, virus producing cells described herein can be transfected with a lentivirus or retrovirus plasmid encoding a CAR construct with engineered envelops directed to T cells. Examples of such envelop polypeptides include, without limitation, envelops engineered to include an anti-CD3, anti-CD2, anti-CD5, anti-CD4, anti-CD8 antibody (e.g., an anti-CD3, anti-CD2, anti-CD5, anti-CD4, or anti-CD8 scFv antibody) or other T cell molecule directed antibody to allow targeted and specific transduction of T cells.

In some cases, a CAR construct can be a first, second, third, or subsequent generation CAR. In some cases, a CAR construct can be designed to promote CD3 zeta stimulation and can include one or more domains of CD28, 41BB, CD27, CD2, OX40, ICOS, other T cell stimulatory molecules, and/or members of the TNFα receptor family. As described herein, a CAR can be directed to any appropriate antigen present on a tumor cell such as those set forth in Table 1.

The invention will be further described in the following examples, which do not limit the scope of the invention described in the claims.

EXAMPLES

Example 1: In Vivo Stimulation and Generation of CART Cells Using Engineered Lentivirus A platform was developed to generate CART cells in vivo. In this platform, lentiviruses are injected intravenously or in situ (e.g., into a tumor site). These virus particles attract T cells and stimulate and transduce the T cells to generate CART cells in situ/in vivo. Specifically, the lentiviruses encode a CD3 targeted envelope and a CAR plasmid to specifically transduce and stimulate T cells in situ and to generate CART cells in situ. See, e.g., FIG. 1A.

Methods/Experimental Design

Experimental Design on Human T Cells

This platform is applied to human T cells in mouse models. Two plasmids are generated: 1) a CD3 directed, mutated measles envelope plasmid (FIG. 2), and 2) a CAR lentivirus plasmid (FIG. 3). CAR19 in B cell leukemia xenografts is used. These plasmids are used for packaging and lentivirus production (as described below).

Two mouse models are employed:
1. Xenograft models: NSG mice are engrafted with the CD19 positive, luciferase positive cell line NALM6 subcutaneously and then engraftment is confirmed by bioluminescence imaging. Mice are then treated with human PBMCs intravenously and intra-tumor injection of our lentivirus particles. Generation of CART cell is measured by flow cytometry. Trafficking of CARTs to tumor sites is assessed and anti-tumor response is measured by bioluminescence imaging as a measure of disease burden.
2. Humanized Immune System (HIS) mice from the Jackson Laboratory: HIS mice are injected with fetal CD34+ cells as neonates and therefore develop human hematopoiesis. Mice are engrafted with the CD19+ cell line NALM6, as previously used. Similarly, CART19 are generated in vivo through the intratumoral injection of lentivirus particles. The activity of CART19 cells in eradication of NALM6 is measured and compared that to ex vivo generated lentivirally transduced CART 19 cells (e.g., as currently used in the clinic).

Generation of CAR Plasmid:

The anti-CD19 clone FMC63 is de novo synthesized into a CAR backbone using 41BB and CD3 zeta and is then cloned into a third generation lentivirus backbone.

To generate control CART19 cells, normal donor T cells are negatively selected using pan T cell kit and expanded ex vivo using anti-CD3/CD28 Dynabeads (Invitrogen, added on the first day of culture). T cells are transduced with lentiviral supernatant one day following stimulation at a multiplicity of infection (MOI) of 3. The anti-CD3/CD28 Dynabeads are removed on day 6 and T cells are grown in T-cell media (X-vivo 15 media, human serum 5%, penicillin, streptomycin and glutamax) for up to 15 days and then cryopreserved for future experiments. Prior to all experiments, T cells are thawed and rested overnight at 37° C.

Cells

The NALM6 cell line is obtained from the ATCC and maintained in R10 media RPMI media, 10% fetal calf serum, penicillin, and streptomycin). NALM6-cells transduced with luciferase-GFP cells under the control of the EF1α promoter are used in some experiments as indicated. De-identified primary human acute lymphoblastic leukemia (ALL) specimens are obtained. All samples are obtained after informed, written consent. For all functional studies, cells are thawed at least 12 hours before analysis and rested overnight at 37° C.

Flow Cytometry Analysis

Anti-human antibodies are purchased from Biolegend, eBioscience, or BD Biosciences. Cells are isolated from in vitro culture or from animals, washed once in PBS supplemented with 2% fetal calf serum, and stained at 4° C. after blockade of Fc receptors. For cell number quantitation, Countbright beads (Invitrogen) are used according to the manufacturer's instructions (Invitrogen). In all analyses, the population of interest is gated based on forward vs. side scatter characteristics followed by singlet gating, and live cells are gated using Live Dead Aqua (Invitrogen). Surface expression of anti-CD19 CAR is detected by staining with an Alexa Fluor 647-conjugated goat anti-mouse F(ab')2 antibody from Jackson Immunoresearch.

T Cell Function Assays:
1. T Cell Degranulation and Intracellular Cytokine Assays Briefly, T cells are incubated with target cells at a 1:5 ratio. After staining for CAR expression; CD107a, CD28, CD49d, and monensin are added at the time of incubation. After 4 hours, cells are harvested and stained for CAR expression, CD3 and Live Dead staining (Invitrogen). Cells are fixed and permeabilized (FIX & PERM® Cell Fixation & Cell Permeabilization Kit, Life technologies) and intracellular cytokine staining is then performed.

2. Proliferation Assays:

T cells are washed and resuspended at $1\times10^7$/mL in 100 µL of PBS and labeled with 100 µL of CFSE 2.5 µM (Life Technologies) for 5 minutes at 37° C. The reaction is then quenched with cold R10, and the cells are washed three times. Targets are irradiated at a dose of 100 Gy. T cells are incubated at a 1:1 ratio with irradiated target cells for 120 hours. Cells are then harvested, stained for CD3, CAR and Live Dead aqua (Invitrogen), and Countbright beads (Invitrogen) are added prior to flow cytometric analysis 3. Cytotoxicity Assays:

NALM6-Luc cells or CFSE (Invitrogen) labelled primary ALL samples are used for cytotoxicity assay. In brief, targets are incubated at the indicated ratios with effector T cells for 4 or 16 hours. Killing is calculated either by bioluminescence imaging on a Xenogen IVIS-200 Spectrum camera or by flow cytometry. For the latter, cells are harvested; Countbright beads and 7-AAD (Invitrogen) are added prior to analysis. Residual live target cells are CFSE+ 7-AAD-.

4. Secreted Cytokine Measurement:

Effector and target cells are incubated at a 1:1 ratio in T cell media for 24 or 72 hours as indicated. Supernatant is harvested and analyzed by 30-plex Luminex array according to the manufacturer's protocol (Invitrogen).

Results

Figure 4A:
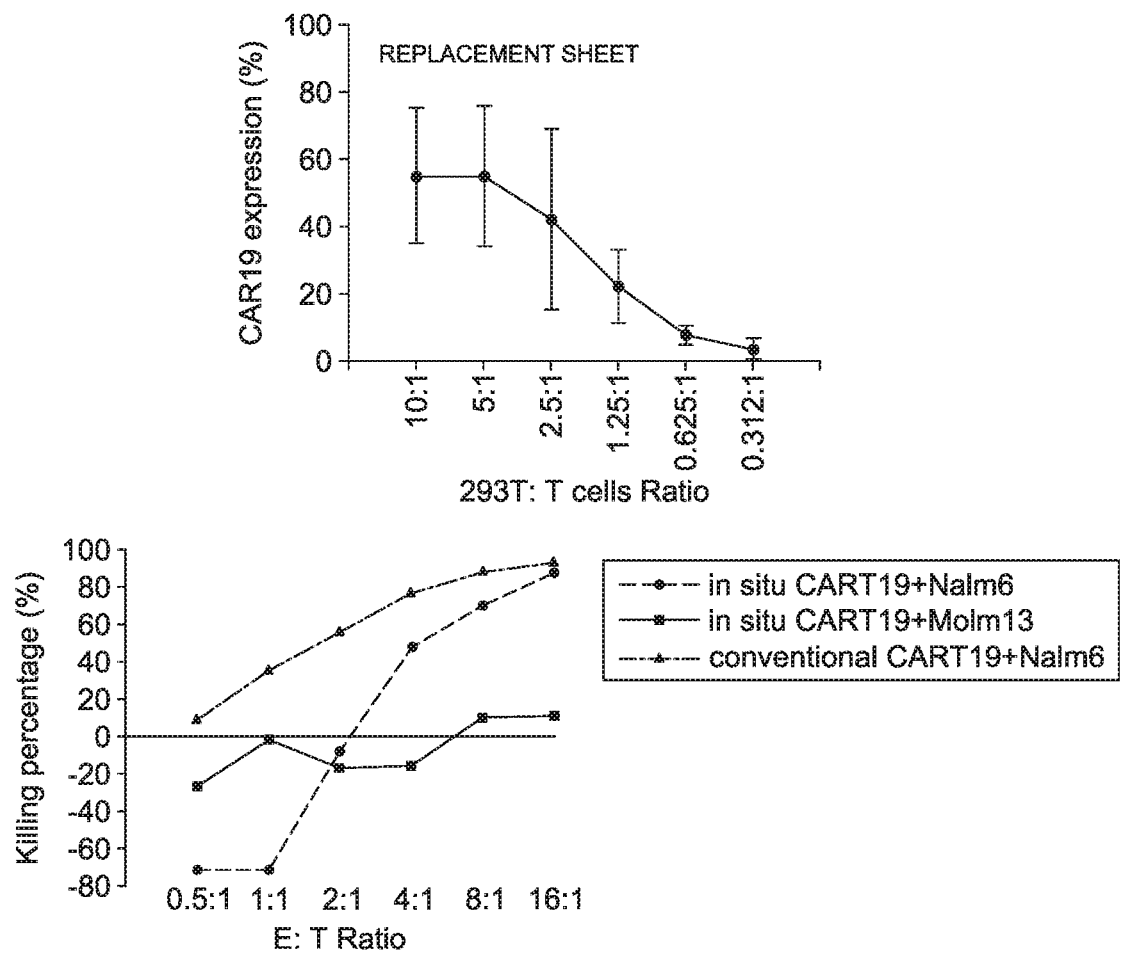
FIGS. 4A-4B. Virus producing cells are capable of transducing T cells and generating CART cells.
Figure 4B:
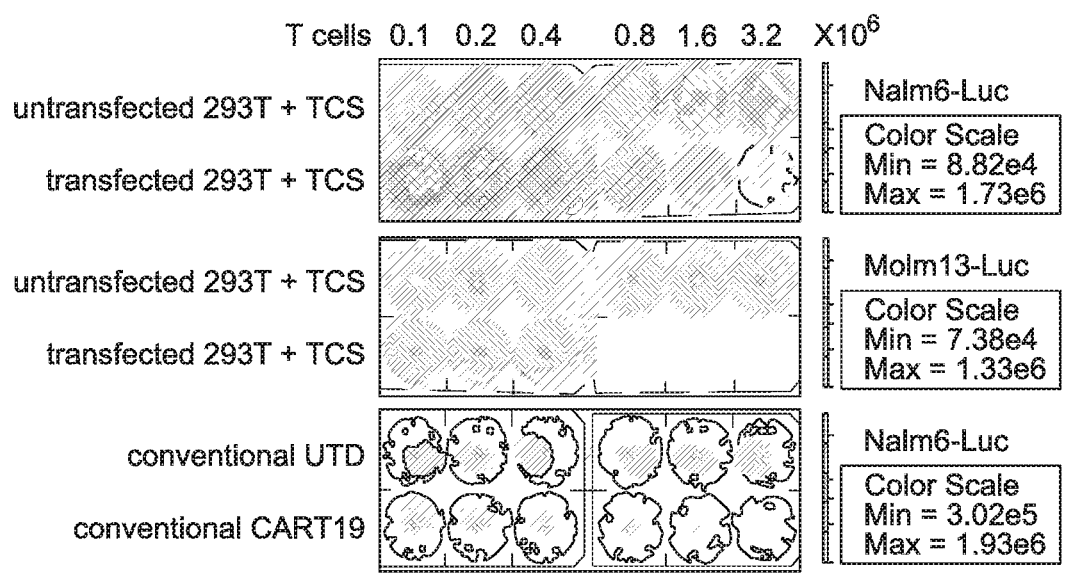

Virus producing cells were capable of transducing T cells and generating CART cells. Here, 293 T cells were transfected with a CAR plasmid, lipofectamine 3000, and packaging plasmids, in the presence of T cells. This resulted in the generation of CART cells. The optimal ratio in 5:1 virus producing cell:T cell resulted in 50-60% transduction efficiency (FIG. 4A). Virus producing cells generated CART19 cells exhibiting potent anti-tumor efficacy against $CD19^+$ tumors (FIG. 4B).

Figure 1B:
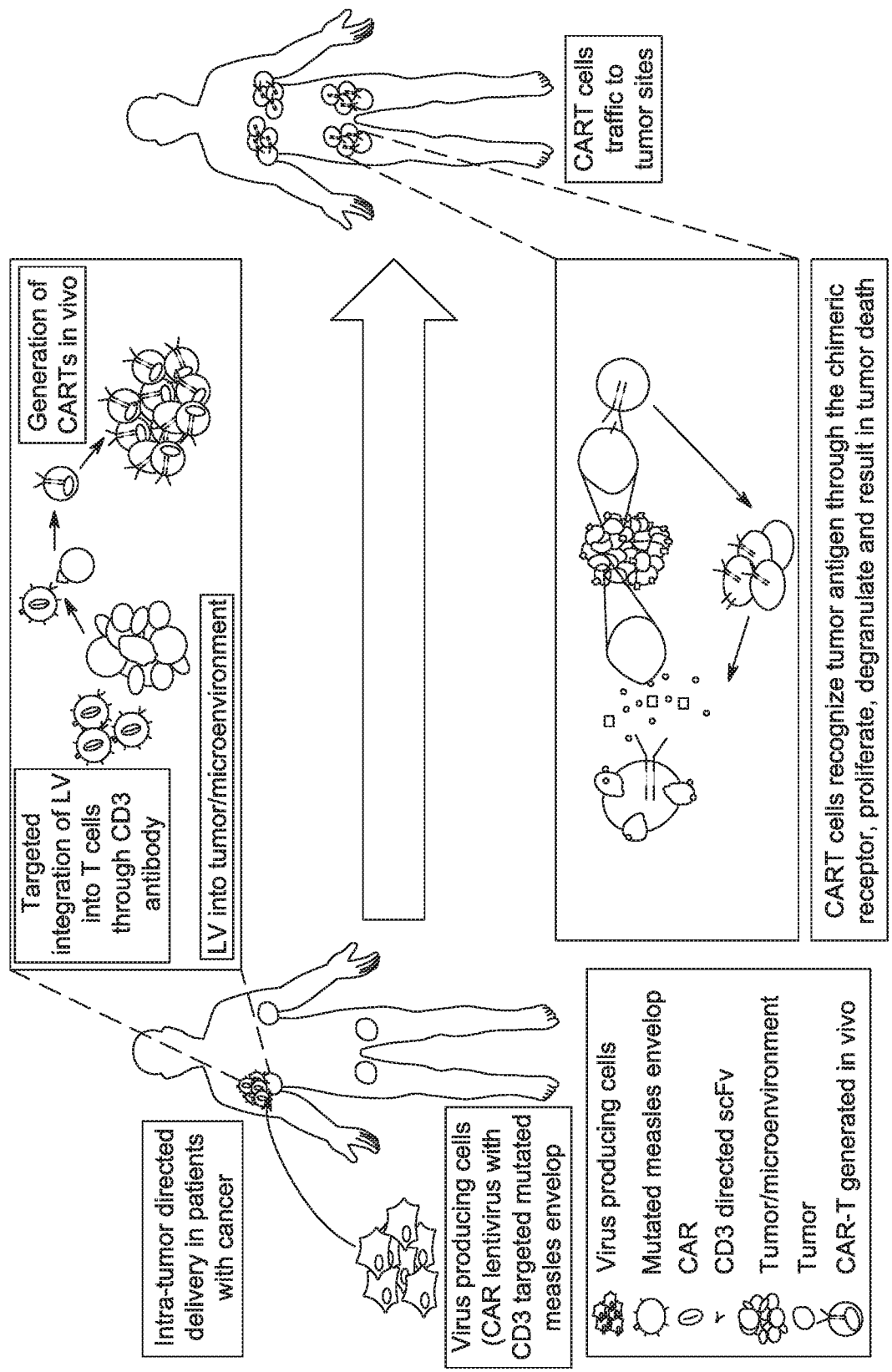

Example 2: In Vivo Generation of CART Cells Through the Use of CD3 Targeted Lentivirus Producing Cells A platform was developed to generate CART cells in vivo. In this platform, lentivirus producing cells are injected in situ (e.g., into a tumor site). These cells are transduced with viral particles described in Example 1 to produce virus particles that attract T cells, and stimulate and transduce the T cells to generate CART cells in situ/in vivo. Specifically, the lentiviruses encode a CD3 targeted envelope and a CAR plasmid to specifically transduce and stimulate T cells in situ, and generate CART cells in situ. See, e.g., FIG. 1B.

Example 3: Generating CART Cells In Vivo Through the Use of Lentivirus Producing Cells The following was performed. Immunocompromised mice (male and female 8-12 week old NOD-SCID-IL2r$\gamma^{-/-}$ (NSG) mice) were engrafted with the human $CD19^+$ luciferase$^+$ tumor cell line NALM6 subcutaneously. Engraftment was confirmed by bioluminescence imaging, and then mice were randomized to be treated with either conventional ex vivo generated CART19 or with 293T cells transfected with CAR plasmid followed by stimulated T cells (FIG. 5A). Ten days later, the mice were bled to look for CART cell generation. The mice treated with transfected 293T cells followed by human T cells had CART19 generated in vivo, and at higher concentration compared to ex vivo generated CART19 (FIG. 5B-C). Follow up of these mice showed similar anti-tumor activity and overall survival that is improved compared to untreated mice (FIG. 5D-F).

Cells Line

NALM6 was purchased from ATCC, (Manassas, VA, USA). These cells were transduced with a luciferase-Zs-Green lentivirus (Addgene, Cambridge, MA, USA) and sorted to 100% purity. Cell lines were cultured in R10 made with RPMI 1640 (Gibco, Gaithersburg, MD, USA), 10% FBS (Millipore Sigma, Ontario, Canada), and 1% Penicillin-Streptomycin-Glutamine (Gibco, Gaithersburg, MD, USA).

Ex Vivo Generated CART Cells

Peripheral blood mononuclear cells (PBMC) were isolated from de-identified donor blood apheresis cones using SepMate tubes (STEMCELL Technologies, Vancouver, Canada). T cells were separated with negative selection magnetic beads using EasySep™ Human T Cell Isolation Kit (STEMCELL Technologies, Vancouver, Canada), and monocytes were positively selected using $CD14^+$ magnetic beads (Miltenyi Biotec, Bergisch Gladbach, Germany). Primary cells were cultured in T Cell Media made with X-Vivo 15 (Lonza, Walkersville, MD, USA) with 10% human serum albumin (Corning Inc., Corning, NY, USA) and 1% Penicillin-Streptomycin-Glutamine (Gibco, Gaithersburg, MD, USA). CD19-directed CART cells were generated through the lentiviral transduction of normal donor T cells as described below. Second generation CAR19 constructs were de novo synthesized (IDT) and cloned into a third generation lentivirus under the control of EF-1α promotor. The CD19-directed single chain variable fragment was derived from the clone FMC63. A second generation 41BB co-stimulated (FMC63-41BBz) CAR construct was synthesized and used for these experiments. Lentiviral particles were generated through the transient transfection of plasmid into 293T virus producing cells in the presence of Lipofectamine 3000 (Invitrogen, Carlsbad, CA, USA), VSV-G, and packaging plasmids (Addgene, Cambridge, MA, USA). T cells isolated from normal donors were stimulated using Cell Therapy Systems Dynabeads CD3/CD28 (Life Technologies, Oslo, Norway) at 1:3 ratio and then transduced with lentivirus particles 24 hours after stimulation at a multiplicity of infection of 3.0. Magnetic bead removal was performed on Day 6, and CART cells were harvested and cryopreserved on Day 8 for future experiments. CART cells were thawed and rested in T cell medium 12 hours prior to their use.

In Vivo Generated CART Cells

To generate CART cells in vivo, mice were treated with (1) the lentivirus producing cells where the lentivirus was capable of expressing the CAR plasmid and then (2) T cells at 5:1 ratio. T cells were activated ex vivo 24 hours prior to injection in mice. Peripheral blood sampling was performed 10 days later to determine the presence of $CAR^+$ cells in the blood, and antitumor burden was monitored serially with bioluminescence imaging as a measure of residual disease.

Example 4: Generating CART Cells In Vivo within Humans Through the Use of Lentivirus Producing Cells The following is performed to generate CART cells in vivo using virus producing cells directly injected into a human, for example, intravenously or intra tumorally. To achieve this, human patients with cancer are first administered a treatment to stimulate their T cells systemically. Then, the human patients are administered virus producing cells that are designed to produce virus (e.g., lentivirus) capable of expressing nucleic acid encoding a CAR (a CAR lentivirus plasmid). The administration can be an intravenous, intratumoral, regional, local, systemic, or subcutaneous administration. Within the human, the virus producing cells are designed to produce the CAR virus in vivo, which in turn transduce T cells in vivo and generate CART cells in vivo. The in vivo generated CART cells can traffic to the tumor site, kill the tumor cells, produce cytokines, and exert their potent antitumor activity. The virus producing cells can serve as a local virus producing factory, producing virus transduced T cells and generating CART cells.

Example 5: Stimulating T Cells In Vivo

Monoclonal antibodies directed to CD3, CD28, 41BB, ICOS, OX40, CD27, CD2, other T cell stimulating molecules, or a combination thereof (e.g., a combination of antibodies such as a combination of anti-CD3 and anti-CD28 antibodies) are used to stimulate T cells in vivo prior to, at the same time as, or after administering virus producing cells capable of producing virus having the ability to express a CAR after that virus infects, for example, a T cell. In some cases, biodegradable beads directed to CD3, CD28, 41BB, ICOS, OX40, CD27, CD2, other T cell stimulating molecules, or a combination thereof (e.g., beads containing a combination of antibodies such as a combination of anti-CD3 and anti-CD28 antibodies) are used to stimulate T cells in vivo prior to, at the same time as, or after administering virus producing cells capable of producing virus having the ability to express a CAR after that virus infects, for example, a T cell. In some cases, nanoparticles carrying antibodies to CD3, CD28, 41BB, ICOS, OX40, CD27, CD2, other T cell stimulating molecules, or a combination thereof (e.g., nanoparticles containing a combination of antibodies such as a combination of anti-CD3 and anti-CD28 antibodies) are used to stimulate T cells in vivo prior to, at the same time as, or after administering virus producing cells capable of producing virus having the ability to express a CAR after that virus infects, for example, a T cell. In some cases, the virus producing cells are engineered to produce viruses (e.g., a lentiviruses) designed to express an anti-CD3 antibody or other T cell stimulating molecule.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for generating T cells expressing a selected antigen receptor in vivo within a mammal, wherein said method comprises administering a viral particle to said mammal, wherein said viral particle comprises (a) nucleic acid encoding said selected antigen receptor and (b) an exogenous polypeptide capable of being encoded by SEQ ID NO:2, wherein said viral particle infects T cells comprising an endogenous T cell receptor within said mammal to form infected T cells, and wherein said infected T cells express said selected antigen receptor and said endogenous T cell receptor.

2. The method of claim 1, wherein said mammal is a human.

3. The method of claim 1, wherein said viral particle is a lentiviral particle.

4. The method of claim 1, wherein said selected antigen receptor is a chimeric antigen receptor.

5. The method of claim 1, wherein said viral particle selected antigen receptor can target one or more cancer cells.

6. The method of claim 5, wherein said one or more cancer cells express a tumor-specific antigen.

7. The method of claim 6, wherein said selected antigen receptor targets said tumor-specific antigen.

8. The method of claim 6, wherein said tumor-specific antigen is CD19.

9. The method of claim 8, wherein said selected antigen receptor targeting said tumor-specific antigen is a CAR targeting CD19.

10. The method of claim 1, wherein said administration is intravenous injection or intratumoral injection.

* * * * *

UNITED STATES PATENT AND TRADEMARK OFFICE
CERTIFICATE OF CORRECTION

Page 1 of 1

PATENT NO. : 12,264,189 B2
APPLICATION NO. : 17/287164
DATED : April 1, 2025
INVENTOR(S) : Saad J. Kenderian and Stephen J. Russell It is certified that error appears in the above-identified patent and that said Letters Patent is hereby corrected as shown below:

In the Claims

In Column 30, Line 32 (Approx.), In Claim 5, after said delete "viral particle".

Signed and Sealed this
Twentieth Day of May, 2025

Coke Morgan Stewart
*Acting Director of the United States Patent and Trademark Office*